United States Patent [19]
Seed et al.

[11] Patent Number: 6,114,148
[45] Date of Patent: *Sep. 5, 2000

[54] HIGH LEVEL EXPRESSION OF PROTEINS

[75] Inventors: Brian Seed, Boston, Mass.; Jurgen Haas, Schriesheim, Germany

[73] Assignee: The General Hospital Corporation, Boston, Mass.

[ * ] Notice: This patent is subject to a terminal disclaimer.

[21] Appl. No.: 08/717,294

[22] Filed: Sep. 20, 1996

(Under 37 CFR 1.47)

[51] Int. Cl.$^7$ .............................. C12N 15/11; C12P 15/40; C12P 19/34
[52] U.S. Cl. ...................... 435/91.1; 435/69.1; 435/69.6; 435/252.3; 435/440; 435/91.4; 435/91.41; 435/325; 435/320.1
[58] Field of Search ............................... 536/23.5, 23.72; 435/69.1, 172.3, 91.5, 252.3, 320.1

[56] References Cited

U.S. PATENT DOCUMENTS

| | | | |
|---|---|---|---|
| 4,652,639 | 3/1987 | Stabinsky | 435/91.52 |
| 5,082,767 | 1/1992 | Hatfield et al. | 435/6 |
| 5,270,171 | 12/1993 | Cercek et al. | 435/29 |
| 5,276,268 | 1/1994 | Strauch et al. | 800/288 |
| 5,405,776 | 4/1995 | Kotewicz et al. | 435/194 |
| 5,464,774 | 11/1995 | Baird et al. | 536/23.51 |
| 5,786,464 | 7/1998 | Seed | 536/23.5 |

FOREIGN PATENT DOCUMENTS

| | | |
|---|---|---|
| 0 335 635 | 10/1989 | European Pat. Off. . |
| 0 345 242 A2 | 12/1989 | European Pat. Off. . |
| WO 96/09378 | 3/1996 | WIPO . |
| WO 96/27675 | 9/1996 | WIPO . |
| WO 97/26333 | 7/1997 | WIPO . |

OTHER PUBLICATIONS

Chiu et al., "Engineered GFP as a Vital Reporter in Plants" *Current Biology* 6:325–330 (1996).
Haas et al., "Codon Usage Limitation in the Expression of HIV–1 Envelope Glycoprotein" *Current Biology* 6:315–324 (1996).
Haseloff et al., "GFP in Plants" *Trends in Genetics* 11:328–329 (1995).
Zolotukhin et al., "A "Humanized" Green Fluorescent Protein cDNA Adapted for High–Level Expression in Mammalian Cells" *Journal of Virology* 70:4646–4654 (1996).
Fortkamp et al., DNA 5:511–517 (1986).
Chou et al., AIDS Research and Human Retroviruses 8:1967–1976 (1992).
Rangwala et al., Gene 122:263–269 (1992).
Scorer et al., Gene 136:111–119 (1993).
Holler et al., Gene 136:323–328 (1993).
Bosch et al., Journal of Virology 68:7566–7569 (1994).
van Hemert et al., Journal of Molecular Evolution 41:132–140 (1995).
Cohen et al. (abstract), in Modern Approaches New Vaccines, 64 (1988).
Hernan et al., Biochemistry 31:8619–8628 (1992).
Williams et al., Nucleic Acids Research 16/22:10453–10467 (1988).
Inouye et al., FEBS Letters 341:277–280 (1994).
Coulombe and Skup, Gene 46:89–95 (1986).
Kamiya et al., Jpn. J. Cancer Res. 80:200–203 (1989).
McCarrey, Nucleic Acids Res. 18:949–955 (1990).
Grantham et al., Nature 319:727–728 (1986).
Kypr et al., Nature 327:20 (1987).
Sharp, Nature 324:114 (1986).
Newgard et al., Proc. Natl. Acad. Sci. USA 83:8132–8136 (1986).
Sharp et al., Nucleic Acids Res. 16:8207–8211 (1988).
Cochrane et al., J. of Virology 65 (10):5305–5314 (1991).
D'Agostino et al., Mol. And Cell. Biol. 12(3):1375–1386 (1992).
Feinberg et al., Cell 46:807–817 (1986).
Hammarskjold et al. J. of Virol. 63(5):1959–1966 (1989).
Nakamura et al., FEBS Letters 289(1):123–125 (1991).
Robinson et al., Nucl. Acids. Res. 12(17):6663–6671 (1984).
Zhang et al., Gene 105(1):61–72 (1991).
Zhang et al., J. of Protein Chem. 12(3):329–335 (1993).
Seetharam et al., "Mistranslation in IGF–1 During Over–Expression of the Protein in *Escherichia Coli* Using a Synthetic Gene Containing Low Frequency Codons," Biochem. Biophys. Res. Comm. 155:518–523 (1988).

*Primary Examiner*—David Guzo
*Assistant Examiner*—Jon Shuman
*Attorney, Agent, or Firm*—Karen L. Elbing

[57] ABSTRACT

The invention features a synthetic gene encoding a protein normally expressed in a mammalian cell wherein at least one non-preferred or less preferred codon in the natural gene encoding the protein has been replaced by a preferred codon encoding the same amino acid.

18 Claims, 18 Drawing Sheets

Syngp120mn

```
   1 CTCGAGATCC ATTGTGCTCT AAAGGAGATA CCCGGCCAGA CACCCTCACC
  51 TGCGGTGCCC AGCTGCCCAG GCTGAGGCAA GAGAAGGCCA GAAACCATGC
 101 CCATGGGGTC TCTGCAACCG CTGGCCACCT TGTACCTGCT GGGGATGCTG
 151 GTCGCTTCCG TGCTAGCCAC CGAGAAGCTG TGGGTGACCG TGTACTACGG
 201 CGTGCCCGTG TGGAAGGAGG CCACCACCAC CCTGTTCTGC GCCAGCGACG
 251 CCAAGGCGTA CGACACCGAG GTGCACAACG TGTGGGCCAC CCAGGCGTGC
 301 GTGCCCACCG ACCCCAACCC CAGGAGGTG GAGCTCGTGA ACGTGACCGA
 351 GAACTTCAAC ATGTGGAAGA ACAACATGGT GGAGCAGATG CATGAGGACA
 401 TCATCAGCCT GTGGGACCAG AGCCTGAAGC CCTGCGTGAA GCTGACCCCC
 451 CTGTGCGTGA CCCTGAACTG CACCGACCTG AGGAACACCA CCAACACCAA
 501 CAACAGCACC GCCAACAACA ACAGCAACAG CGAGGGCACC ATCAAGGGCG
 551 GCGAGATGAA GAACTGCAGC TTCAACATCA CCACCAGCAT CCGCGACAAG
 601 ATGCAGAAGG AGTACGCCCT GCTGTACAAG CTGGATATCG TGAGCATCGA
 651 CAACGACAGC ACCAGCTACC GCCTGATCTC CTGCAACACC AGCGTGATCA
 701 CCCAGGCCTG CCCCAAGATC AGCTTCGAGC CCATCCCCAT CCACTACTGC
 751 GCCCCGCCG GCTTCGCCAT CCTGAAGTGC AACGACAAGA AGTTCAGCGG
 801 CAAGGGCAGC TGCAAGAACG TGAGCACCGT GCAGTGCACC CACGGCATCC
 851 GGCCGGTGGT GAGCACCCAG CTCCTGCTGA ACGGCAGCCT GGCCGAGGAG
 901 GAGGTGGTGA TCCGCAGCGA GAACTTCACC GACAACGCCA AGACCATCAT
 951 CGTGCACCTG AATGAGAGCG TGCAGATCAA CTGCACGCGT CCCAACTACA
1001 ACAAGCGCAA GCGCATCCAC ATCGGCCCCG GCGCGCCTT CTACACCACC
1051 AAGAACATCA TCGGCACCAT CCGCCAGGCC CACTGCAACA TCTCTAGAGC
1101 CAAGTGGAAC GACACCCTGC GCCAGATCGT GAGCAAGCTG AAGGAGCAGT
1151 TCAAGAACAA GACCATCGTG TTCAACCAGA GCAGCGGCGG CGACCCCGAG
1201 ATCGTGATGC ACAGCTTCAA CTGCGGCGGC GAATTCTTCT ACTGCAACAC
1251 CAGCCCCCTG TTCAACAGCA CCTGGAACGG CAACAACACC TGGAACAACA
1301 CCACCGGCAG CAACAACAAT ATTACCCTCC AGTGCAAGAT CAAGCAGATC
1351 ATCAACATGT GGCAGGAGGT GGGCAAGGCC ATGTACGCCC CCCCCATCGA
1401 GGGCCAGATC CGGTGCAGCA GCAACATCAC CGGTCTGCTG CTGACCCGCG
1451 ACGGCGGCAA GGACACCGAC ACCAACGACA CCGAAATCTT CCGCCCCGGC
```

Fig. 1A

```
1501  GGCGGCGACA  TGCGCGACAA  CTGGAGATCT  GAGCTGTACA  AGTACAAGGT
1551  GGTGACGATC  GAGCCCCTGG  GCGTGGCCCC  CACCAAGGCC  AAGCGCCGCG
1601  TGGTGCAGCG  CGAGAAGCGC  TAAAGCGGCC  GC          (SEQ ID NO: 34)
```

Fig. 1B

Syngp160mn

```
   1 ACCGAGAAGC TGTGGGTGAC CGTGTACTAC GGCGTGCCCG TGTGGAAGGA
  51 GGCCACCACC ACCCTGTTCT GCGCCAGCGA CGCCAAGGCG TACGACACCG
 101 AGGTGCACAA CGTGTGGGCC ACCCAGGCGT GCGTGCCCAC CGACCCCAAC
 151 CCCCAGGAGG TGGAGCTCGT GAACGTGACC GAGAACTTCA ACATGTGGAA
 201 GAACAACATG GTGGAGCAGA TGCATGAGGA CATCATCAGC CTGTGGGACC
 251 AGAGCCTGAA GCCCTGCGTG AAGCTGACCC CCCTGTGCGT GACCCTGAAC
 301 TGCACCGACC TGAGGAACAC CACCAACACC AACAACAGCA CCGCCAACAA
 351 CAACAGCAAC AGCGAGGGCA CCATCAAGGG CGGCGAGATG AAGAACTGCA
 401 GCTTCAACAT CACCACCAGC ATCCGCGACA AGATGCAGAA GGAGTACGCC
 451 CTGCTGTACA AGCTGGATAT CGTGAGCATC GACAACGACA GCACCAGCTA
 501 CCGCCTGATC TCCTGCAACA CCAGCGTGAT CACCCAGGCC TGCCCCAAGA
 551 TCAGCTTCGA GCCCATCCCC ATCCACTACT GCGCCCCCGC CGGCTTCGCC
 601 ATCCTGAAGT GCAACGACAA GAAGTTCAGC GGCAAGGGCA GCTGCAAGAA
 651 CGTGAGCACC GTGCAGTGCA CCCACGGCAT CCGGCCGGTG GTGAGCACCC
 701 AGCTCCTGCT GAACGGCAGC CTGGCCGAGG AGGAGGTGGT GATCCGCAGC
 751 GAGAACTTCA CCGACAACGC CAAGACCATC ATCGTGCACC TGAATGAGAG
 801 CGTGCAGATC AACTGCACGC GTCCAACTA CAACAAGCGC AAGCGCATCC
 851 ACATCGGCCC CGGGCGCGCC TTCTACACCA CCAAGAACAT CATCGGCACC
 901 ATCCGCCAGG CCCACTGCAA CATCTCTAGA GCCAAGTGGA ACGACACCCT
 951 GCGCCAGATC GTGAGCAAGC TGAAGGAGCA GTTCAAGAAC AAGACCATCG
1001 TGTTCAACCA GAGCAGCGGC GGCGACCCCG AGATCGTGAT GCACAGCTTC
1051 AACTGCGGCG GCGAATTCTT CTACTGCAAC ACCAGCCCCC TGTTCAACAG
1101 CACCTGGAAC GGCAACAACA CCTGGAACAA CACCACCGGC AGCAACAACA
1151 ATATTACCCT CCAGTGCAAG ATCAAGCAGA TCATCAACAT GTGGCAGGAG
1201 GTGGGCAAGG CCATGTACGC CCCCCCCATC GAGGGCCAGA TCCGGTGCAG
1251 CAGCAACATC ACCGGTCTGC TGCTGACCCG CGACGGCGGC AAGGACACCG
1301 ACACCAACGA CACCGAAATC TTCCGCCCCG GCGGCGGCGA CATGCGCGAC
1351 AACTGGAGAT CTGAGCTGTA CAAGTACAAG GTGGTGACGA TCGAGCCCCT
1401 GGGCGTGGCC CCCACCAAGG CCAAGCGCCG CGTGGTGCAG CGCGAGAAGC
1451 GGGCCGCCAT CGGCGCCCTG TTCCTGGGCT TCCTGGGGGC GGCGGGCAGC
```

Fig. 1C

```
1501 ACCATGGGGG CCGCCAGCGT GACCCTGACC GTGCAGGCCC GCCTGCTCCT
1551 GAGCGGCATC GTGCAGCAGC AGAACAACCT CCTCCGCGCC ATCGAGGCCC
1601 AGCAGCATAT GCTCCAGCTC ACCGTGTGGG GCATCAAGCA GCTCCAGGCC
1651 CGCGTGCTGG CCGTGGAGCG CTACCTGAAG GACCAGCAGC TCCTGGGCTT
1701 CTGGGGCTGC TCCGGCAAGC TGATCTGCAC CACCACGGTA CCCTGGAACG
1751 CCTCCTGGAG CAACAAGAGC CTGGACGACA TCTGGAACAA CATGACCTGG
1801 ATGCAGTGGG AGCGCGAGAT CGATAACTAC ACCAGCCTGA TCTACAGCCT
1851 GCTGGAGAAG AGCCAGACCC AGCAGGAGAA GAACGAGCAG GAGCTGCTGG
1901 AGCTGGACAA GTGGGCGAGC CTGTGGAACT GGTTCGACAT CACCAACTGG
1951 CTGTGGTACA TCAAAATCTT CATCATGATT GTGGGCGGCC TGGTGGGCCT
2001 CCGCATCGTG TTCGCCGTGC TGAGCATCGT GAACCGCGTG CGCCAGGGCT
2051 ACAGCCCCCT GAGCCTCCAG ACCCGGCCCC CCGTGCCGCG CGGGCCCGAC
2101 CGCCCCGAGG GCATCGAGGA GGAGGGCGGC GAGCGCGACC GCGACACCAG
2151 CGGCAGGCTC GTGCACGGCT TCCTGGCGAT CATCTGGGTC GACCTCCGCA
2201 GCCTGTTCCT GTTCAGCTAC CACCACCGCG ACCTGCTGCT GATCGCCGCC
2251 CGCATCGTGG AACTCCTAGG CCGCCGCGGC TGGGAGGTGC TGAAGTACTG
2301 GTGGAACCTC CTCCAGTATT GGAGCCAGGA GCTGAAGTCC AGCGCCGTGA
2351 GCCTGCTGAA CGCCACCGCC ATCGCCGTGG CCGAGGGCAC CGACCGCGTG
2401 ATCGAGGTGC TCCAGAGGGC CGGGAGGGCG ATCCTGCACA TCCCCACCCG
2451 CATCCGCCAG GGGCTCGAGA GGGCGCTGCT G        (SEQ ID NO: 35)
```

Fig. 1D

```
env  atg aat cca gta ata agt ata aca tta tta agt gta atg agt aga gga caa  60
wt   atg aac cca gtg atc agc agc act ctc ctt tca gtc atg tcc cga gga cag
     M   N   P   V   I   S   I   T   L   L   S   V   M   S   R   G   Q env  aga gta ata agt tta aca gca atc tta tta aat caa aat tta aga tgt aga cat 120
wt   agg gtg atc agc agc ctg aca gcc ctt ctt aac cag ctg gac tgc cgt cat
     R   V   I   S   L   T   A   I   L   L   N   Q   N   L   R   C   R   H env  gaa aat aat aca ac

```
  1 GAATTCACGC GTAAGCTTGC CGCCACCATG GTGAGCAAGG GCGAGGAGCT
 51 GTTCACCGGG GTGGTGCCCA TCCTGGTCGA GCTGGACGGC GACGTGAACG
101 GCCACAAGTT CAGCGTGTCC GGCGAGGGCG AGGGCGATGC CACCTACGGC
151 AAGCTGACCC TGAAGTTCAT CTGCACCACC GGCAAGCTGC CCGTGCCCTG
201 GCCCACCCTC GTGACCACCT TCAGCTACGG CGTGCAGTGC TTCAGCCGCT
251 ACCCCGACCA CATGAAGCAG CACGACTTCT TCAAGTCCGC CATGCCCGAA
301 GGCTACGTCC AGGAGCGCAC CATCTTCTTC AAGGACGACG GCAACTACAA
351 GACCCGCGCC GAGGTGAAGT TCGAGGGCGA CACCCTGGTG AACCGCATCG
401 AGCTGAAGGG CATCGACTTC AAGGAGGACG GCAACATCCT GGGGCACAAG
451 CTGGAGTACA ACTACAACAG CCACAACGTC TATATCATGG CCGACAAGCA
501 GAAGAACGGC ATCAAGGTGA ACTTCAAGAT CCGCCACAAC ATCGAGGACG
551 GCAGCGTGCA GCTCGCCGAC CACTACCAGC AGAACACCCC CATCGGCGAC
601 GGCCCCGTGC TGCTGCCCGA CAACCACTAC CTGAGCACCC AGTCCGCCCT
651 GAGCAAAGAC CCCAACGAGA AGCGCGATCA CATGGTCCTG CTGGAGTTCG
701 TGACCGCCGC CGGGATCACT CACGGCATGG ACGAGCTGTA CAAGTAAAGC
751 GGCCGCGGAT CC
```

Fig. 11

```
   1  AAGCTTAAAC CATGCCCATG GGGTCTCTGC AACCGCTGGC CACCTTGTAC
  51  CTGCTGGGGA TGCTGGTCGC TTCCGTGCTA GCCGCCACCA GAAGATACTA
 101  CCTGGGTGCA GTGGAACTGT CATGGGACTA TATGCAAAGT GATCTCGGTG
 151  AGCTGCCTGT GGACGCAAGA TTTCCTCCTA GAGTGCCAAA ATCTTTTCCA
 201  TTCAACACCT CAGTCGTGTA CAAAAAGACT CTGTTTGTAG AATTCACGGA
 251  TCACCTTTTC AACATCGCTA AGCCAAGGCC ACCCTGGATG GGTCTGCTAG
 301  GTCCTACCAT CCAGGCTGAG GTTTATGATA CAGTGGTCAT TACACTTAAG
 351  AACATGGCTT CCCATCCTGT CAGTCTTCAT GCTGTTGGTG TATCCTACTG
 401  GAAAGCTTCT GAGGGAGCTG AATATGATGA TCAGACCAGT CAAAGGGAGA
 451  AAGAAGATGA TAAAGTCTTC CCTGGTGGAA GCCATACATA TGTCTGGCAG
 501  GTCCTGAAAG AGAATGGTCC AATGGCCTCT GACCCACTGT GCCTTACCTA
 551  CTCATATCTT TCTCATGTGG ACCTGGTAAA AGACTTGAAT TCAGGCCTCA
 601  TTGGAGCCCT ACTAGTATGT AGAGAAGGGA GTCTGGCCAA GGAAAAGACA
 651  CAGACCTTGC ACAAATTTAT ACTACTTTTT GCTGTATTTG ATGAAGGGAA
 701  AAGTTGGCAC TCAGAAACAA AGAACTCCTT GATGCAGGAT AGGGATGCTG
 751  CATCTGCTCG GGCCTGGCCT AAAATGCACA CAGTCAATGG TTATGTAAAC
 801  AGGTCTCTGC CAGGTCTGAT TGGATGCCAC AGGAAATCAG TCTATTGGCA
 851  TGTGATTGGA ATGGGCACCA CTCCTGAAGT GCACTCAATA TTCCTCGAAG
 901  GTCACACATT TCTTGTGAGG AACCATCGCC AGGCGTCCTT GGAAATCTCG
 951  CCAATAACTT TCCTTACTGC TCAAACACTC TTGATGGACC TTGGACAGTT
1001  TCTACTGTTT TGTCATATCT CTTCCCACCA ACATGATGGC ATGGAAGCTT
1051  ATGTCAAAGT AGACAGCTGT CCAGAGGAAC CCAACTACG AATGAAAAAT
1101  AATGAAGAAG CGGAAGACTA TGATGATGAT CTTACTGATT CTGAAATGGA
1151  TGTGGTCAGG TTTGATGATG ACAACTCTCC TTCCTTTATC CAAATTCGCT
1201  CAGTTGCCAA GAAGCATCCT AAAACTTGGG TACATTACAT TGCTGCTGAA
1251  GAGGAGGACT GGGACTATGC TCCCTTAGTC CTCGCCCCG ATGACAGAAG
1301  TTATAAAAGT CAATATTTGA CAATGGCCC TCAGCGGATT GGTAGGAAGT
1351  ACAAAAAAGT CCGATTTATG GCATACACAG ATGAAACCTT TAAGACTCGT
1401  GAAGCTATTC AGCATGAATC AGGAATCTTG GGACCTTTAC TTTATGGGGA
1451  AGTTGGAGAC ACACTGTTGA TTATATTTAA GAATCAAGCA AGCAGACCAT
1501  ATAACATCTA CCCTCACGGA ATCACTGATG TCCGTCCTTT GTATTCAAGG
1551  AGATTACCAA AAGGTGTAAA ACATTTGAAG GATTTTCCAA TTCTGCCAGG
1601  AGAAATATTC AAATATAAAT GGACAGTGAC TGTAGAAGAT GGGCCAACTA
1651  AATCAGATCC TCGGTGCCTG ACCCGCTATT ACTCTAGTTT CGTTAATATG
1701  GAGAGAGATC TAGCTTCAGG ACTCATTGGC CCTCTCCTCA TCTGCTACAA
1751  AGAATCTGTA GATCAAAGAG GAAACCAGAT AATGTCAGAC AAGAGGAATG
1801  TCATCCTGTT TTCTGTATTT GATGAGAACC GAAGCTGGTA CCTCACAGAG
1851  AATATACAAC GCTTTCTCCC CAATCCAGCT GGAGTGCAGC TTGAGGATCC
1901  AGAGTTCCAA GCCTCCAACA TCATGCACAG CATCAATGGC TATGTTTTTG
1951  ATAGTTTGCA GTTGTCAGTT TGTTTGCATG AGGTGGCATA CTGGTACATT
2001  CTAAGCATTG GAGCACAGAC TGACTTCCTT TCTGTCTTCT TCTCTGGATA
2051  TACCTTCAAA CACAAAATGG TCTATGAAGA CACACTCACC CTATTCCCAT
2101  TCTCAGGAGA AACTGTCTTC ATGTCGATGG AAAACCCAGG TCTATGGATT
2151  CTGGGGTGCC ACAACTCAGA CTTTCGGAAC AGAGGCATGA CCGCCTTACT
2201  GAAGGTTTCT AGTTGTGACA GAACACTGG TGATTATTAC GAGGACAGTT
2251  ATGAAGATAT TTCAGCATAC TTGCTGAGTA AAAACAATGC CATTGAACCA
2301  AGAAGCTTCT CCCAGAATTC AAGACACCCT AGCACTAGGC AAAAGCAATT
2351  TAATGCCACC CCACCAGTCT TGAAACGCCA TCAACGGGAA ATAACTCGTA
2401  CTACTCTTCA GTCAGATCAA GAGGAAATTG ACTATGATGA TACCATATCA
2451  GTTGAAATGA AGAAGGAAGA TTTTGACATT TATGATGAGG ATGAAAATCA
2501  GAGCCCCCGC AGCTTTCAAA AGAAAACACG ACACTATTTT ATTGCTGCAG
2551  TGGAGAGGCT CTGGGATTAT GGGATGAGTA GCTCCCCACA TGTTCTAAGA
2601  AACAGGGCTC AGAGTGGCAG TGTCCCTCAG TTCAAGAAAG TTGTTTTCCA
2651  GGAATTTACT GATGGCTCCT TTACTCAGCC CTTATACCGT GGAGAACTAA
```

Fig. 12A

```
2701  ATGAACATTT  GGGACTCCTG  GGGCCATATA  TAAGAGCAGA  AGTTGAAGAT
2751  AATATCATGG  TAACTTTCAG  AAATCAGGCC  TCTCGTCCCT  ATTCCTTCTA
2801  TTCTAGCCTT  ATTTCTTATG  AGGAAGATCA  GAGGCAAGGA  GCAGAACCTA
2851  GAAAAAACTT  TGTCAAGCCT  AATGAAACCA  AAACTTACTT  TTGGAAAGTG
2901  CAACATCATA  TGGCACCCAC  TAAAGATGAG  TTTGACTGCA  AAGCCTGGGC
2951  TTATTTCTCT  GATGTTGACC  TGGAAAAAGA  TGTGCACTCA  GGCCTGATTG
3001  GACCCCTTCT  GGTCTGCCAC  ACTAACACAC  TGAACCCTGC  TCATGGAGA
3051  CAAGTGACAG  TACAGGAATT  TGCTCTGTTT  TTCACCATCT  TTGATGAGAC
3101  CAAAAGCTGG  TACTTCACTG  AAAATATGGA  AAGAAACTGC  AGGGCTCCCT
3151  GCAATATCCA  GATGGAAGAT  CCCACTTTTA  AAGAGAATTA  TCGCTTCCAT
3201  GCAATCAATG  CTACATAAT   GGATACACTA  CCTGGCTTAG  TAATGGCTCA
3251  GGATCAAAGG  ATTCGATGGT  ATCTGCTCAG  CATGGGCAGC  AATGAAAACA
3301  TCCATTCTAT  TCATTTCAGT  GGACATGTGT  TCACTGTACG  AAAAAAAGAG
3351  GAGTATAAAA  TGGCACTGTA  CAATCTCTAT  CCAGGTGTTT  TTGAGACAGT
3401  GGAAATGTTA  CCATCCAAAG  CTGGAATTTG  GCGGGTGGAA  TGCCTTATTG
3451  GCGAGCATCT  ACATGCTGGG  ATGAGCACAC  TTTTTCTGGT  GTACAGCAAT
3501  AAGTGTCAGA  CTCCCCTGGG  AATGGCTTCT  GGACACATTA  GAGATTTTCA
3551  GATTACAGCT  TCAGGACAAT  ATGGACAGTG  GGCCCCAAAG  CTGGCCAGAC
3601  TTCATTATTC  CGGATCAATC  AATGCCTGGA  GCACCAAGGA  GCCCTTTTCT
3651  TGGATCAAGG  TGGATCTGTT  GGCACCAATG  ATTATTCACG  GCATCAAGAC
3701  CCAGGGTGCC  CGTCAGAAGT  TCTCCAGCCT  CTACATCTCT  CAGTTTATCA
3751  TCATGTATAG  TCTTGATGGG  AAGAAGTGGC  AGACTTATCG  AGGAAATTCC
3801  ACTGGAACCT  TAATGGTCTT  CTTTGGCAAT  GTGGATTCAT  CTGGGATAAA
3851  ACACAATATT  TTTAACCCTC  CAATTATTGC  TCGATACATC  CGTTTGCACC
3901  CAACTCATTA  TAGCATTCGC  AGCACTCTTC  GCATGGAGTT  GATGGGCTGT
3951  GATTTAAATA  GTTGCAGCAT  GCCATTGGGA  ATGGAGAGTA  AAGCAATATC
4001  AGATGCACAG  ATTACTGCTT  CATCCTACTT  TACCAATATG  TTTGCCACCT
4051  GGTCTCCTTC  AAAAGCTCGA  CTTCACCTCC  AAGGGAGGAG  TAATGCCTGG
4101  AGACCTCAGG  TGAATAATCC  AAAAGAGTGG  CTGCAAGTGG  ACTTCCAGAA
4151  GACAATGAAA  GTCACAGGAG  TAACTACTCA  GGGAGTAAAA  TCTCTGCTTA
4201  CCAGCATGTA  TGTGAAGGAG  TTCCTCATCT  CCAGCAGTCA  AGATGGCCAT
4251  CAGTGGACTC  TCTTTTTTCA  GAATGGCAAA  GTAAAGGTTT  TTCAGGGAAA
4301  TCAAGACTCC  TTCACACCTG  TGGTGAACTC  TCTAGACCCA  CCGTTACTGA
4351  CTCGCTACCT  TCGAATTCAC  CCCCAGAGTT  GGGTGCACCA  GATTGCCCTG
4401  AGGATGGAGG  TTCTGGGCTG  CGAGGCACAG  GACCTCTACT  GAGGGTGGCC
4451  ACTGCAGCAC  CTGCCACTGC  CGTCACCTCT  CCCTCCTCAG  CTCCAGGGCA
4501  GTGTCCCTCC  CTGGCTTGCC  TTCTACCTTT  GTGCTAAATC  CTAGCAGACA
4551  CTGCCTTGAA  GCCTCCTGAA  TTAACTATCA  TCAGTCCTGC  ATTTCTTTGG
4601  TGGGGGGCCA  GGAGGGTGCA  TCCAATTTAA  CTTAACTCTT  ACCGTCGACC
4651  TGCAGGCCCA  ACGCGGCCGC
```

Fig. 12B

```
   1 AAGCTTAAAC CATGCCCATG GGGTCTCTGC AACCGCTGGC CACCTTGTAC
  51 CTGCTGGGGA TGCTGGTCGC TTCCGTGCTA GCCGCCACCC GCCGCTACTA
 101 CCTGGGCGCC GTGGAGCTGT CCTGGGACTA CATGCAGAGC GACCTGGGCG
 151 AGCTCCCCGT GGACGCCCGC TTCCCCCCCC GCGTGCCCAA GAGCTTCCCC
 201 TTCAACACCA GCGTGGTGTA CAAGAAAACC CTGTTCGTGG AGTTCACCGA
 251 CCACCTGTTC AACATTGCCA AGCCGCGCCC CCCTGGATG GGCCTGCTGG
 301 GCCCCACCAT CCAGGCCGAG GTGTACGACA CCGTGGTGAT CACCCTGAAG
 351 AACATGGCCA GCCACCCCGT CAGCCTGCAC GCCGTGGGCG TGAGCTACTG
 401 GAAGGCCAGC GAGGGCGCCG AGTACGACGA CCAGACGTCC CAGCGCGAGA
 451 AGGAGGACGA CAAGGTGTTC CGGGGGGGA GCCACACCTA CGTGTGGCAG
 501 GTGCTTAAGG AGAACGGCCC TATGGCCAGC GACCCCTGT GCCTGACCTA
 551 CAGCTACCTG AGCCACGTGG ACCTGGTGAA GGATCTGAAC AGCGGGCTGA
 601 TCGGCGCCCT GCTGGTGTGT CGCGAGGGCA GCCTGGCCAA GGAGAAAACC
 651 CAGACCCTGC ACAAGTTCAT CCTGCTGTTC GCCGTGTTCG ACGAGGGGAA
 701 GAGCTGGCAC AGCGAGACTA AGAACAGCCT GATGCAGGAC CGCGACGCCG
 751 CCAGCGCCCG CGCCTGGCCC AAGATGCACA CCGTTAACGG CTACGTGAAC
 801 CGCAGCCTGC CCGGCCTGAT CGGCTGCCAC CGCAAGAGCG TGTACTGGCA
 851 CGTCATCGGC ATGGGCACCA CCCCTGAGGT GCACAGCATC TTCCTGGAGG
 901 GCCACACCTT CCTGGTGCGC AACCACCGCC AGGCCAGCCT GGAGATCAGC
 951 CCCATCACCT TCCTGACTGC CCAGACCCTG CTGATGGACC TAGGCCAGTT
1001 CCTGCTGTTC TGCCACATCA GCAGCCACCA GCACGACGGC ATGGAGGCTT
1051 ACGTGAAGGT GGACAGCTGC CCCGAGGAGC CCCAGCTGCG CATGAAGAAC
1101 AACGAGGAGG CCGAGGACTA CGACGACGAC CTGACCGACA GCGAGATGGA
1151 TGTCGTACGC TTCGACGACG ACAACAGCCC CAGCTTCATC CAGATCCGCA
1201 GCGTGGCCAA GAAGCACCCT AAGACCTGGG TGCACTACAT CGCCGCCGAG
1251 GAGGAGGACT GGGACTACGC CCCGCTAGTA CTGGCCCCCG ACGACCGCAG
1301 CTACAAGAGC CAGTACCTGA ACAACGGCCC CAGCGCATCG GCCGCAAGT
1351 ACAAGAAGGT GCGCTTCATG GCCTACACCG ACGAGACTTT CAAGACCCGC
1401 GAGGCCATCC AGCACGAGTC CGGCATCCTC GGCCCCCTGC TGTACGGCGA
1451 GGTGGGCGAC ACCCTGCTGA TCATCTTCAA GAACCAGGCC AGCAGGCCCT
1501 ACAACATCTA CCCCCACGGC ATCACCGACG TGCGCCCCCT GTACAGCCGC
1551 CGCCTGCCCA AGGGCGTGAA GCACCTGAAG GACTTCCCCA TCCTGCCCGG
1601 CGAGATCTTC AAGTACAAGT GGACCGTGAC CGTGGAGGAC GGCCCCACCA
1651 AGAGCGACCC CCGCTGCCTG ACCCGCTACT ACAGCAGCTT CGTGAACATG
1701 GAGCGCGACC TGGCCTCCGG ACTGATCGGC CCCCTGCTGA TCTGCTACAA
1751 GGAGAGCGTG GACCAGCGCG GCAACCAGAT CATGAGCGAC AAGCGCAACG
1801 TGATCCTGTT CAGCGTGTTC GACGAGAACC GCAGCTGGTA TCTGACCGAG
1851 AACATCCAGC GCTTCCTGCC CAACCCCGCT GGCGTGCAGC TGGAAGATCC
1901 CGAGTTCCAG GCCAGCAACA TCATGCACAG CATCAACGGC TACGTGTTCG
1951 ACAGCCTGCA GCTGAGCGTG TGCCTGCATG AGGTGGCCTA CTGGTACATC
2001 CTGAGCATCG GCGCCCAGAC CGACTTCCTG AGCGTGTTCT TCTCCGGGTA
2051 TACCTTCAAG CACAAGATGG TGTACGAGGA CACCCTGACC CTGTTCCCCT
2101 TCTCCGGCGA GACTGTGTTC ATGTCTATGG AGAACCCCGG CCTGTGGATT
2151 CTGGGCTGCC ACAACAGCGA CTTCCGCAAC CGCGGCATGA CTGCCCTGCT
2201 GAAAGTCTCC AGCTGCGACA GAACACCGG CGACTACTAC GAGGACAGCT
2251 ACGAGGACAT CTCCGCCTAC CTGCTGTCCA AGAACAACGC CATCGAGCCC
2301 CGCTCCTTCT CCCAAAACTC CCGCCACCCC AGCACGCGTC AGAAGCAGTT
2351 CAACGCCACC CCCCCCGTGC TGAAGCGCCA CCAGCGCGAG ATCACCCGCA
2401 CCACCCTGCA AAGCGACCAG GAGGAGATCG ACTACGACGA CACCATCAGC
2451 GTGGAGATGA AGAAGGAGGA CTTCGACATC TACGACGAGG ACGAGAACCA
2501 GAGCCCCCGC TCCTTCCAAA AGAAACCCG CCACTACTTC ATCGCCGCCG
2551 TGGAGCGCCT GTGGGACTAC GGCATGAGCA GCAGCCCCCA CGTCCTGCGC
2601 AACCGCGCCC AGAGCGGCAG CGTGCCCCAG TTCAAGAAGG TGGTGTTCCA
2651 GGAGTTCACC GACGGCAGCT TCACCCAGCC CCTGTACCGC GGCGAGCTGA
```

Fig. 13A

```
2701  ACGAGCACCT GGGCCTGCTC GGCCCCTACA TCCGCGCCGA GGTGGAGGAC
2751  AACATCATGG TGACCTTCCG CAACCAAGCC TCCCGGCCCT ACTCCTTCTA
2801  CTCCTCCCTG ATCAGCTACG AGGAGGACCA GCGCCAGGGC GCCGAGCCCC
2851  GCAAGAACTT CGTGAAGCCC AACGAGACTA AGACCTACTT CTGGAAGGTG
2901  CAGCACCACA TGGCCCCCAC CAAGGACGAG TTCGACTGCA AGGCCTGGGC
2951  CTACTTCAGC GACGTGGACC TGGAGAAGGA CGTGCACAGC GGCCTGATCG
3001  GCCCCTGCT GGTGTGCCAC ACCAACACCC TGAACCCCCC CCACGGGAGG
3051  CAGGTGACTG TGCAGGAATT TGCCCTGTTC TTCACCATCT TCGACGAGAC
3101  TAAGAGCTGG TACTTCACCG AGAACATGGA GCGCAACTGC CGCGCCCCT
3151  GCAACATCCA GATGGAAGAT CCCACCTTCA AGGAGAACTA CCGCTTCCAC
3201  GCCATCAACG GCTACATCAT GGACACCCTG CCCGGCCTGG TGATGGCCCA
3251  GGACCAGCGC ATCCGCTGGT ACCTGCTGTC TATGGGCAGC AACGAGAACA
3301  TCCACAGCAT CCACTTCAGC GGCCACGTTT TCACCGTGCG CAAGAAGGAG
3351  GAGTACAAGA TGGCCCTGTA CAACCTGTAC CCCGGCGTGT TCGAGACTGT
3401  GGAGATGCTG CCCAGCAAGG CCGGGATCTG GCGCGTGGAG TGCCTGATCG
3451  GCGAGCACCT GCACGCCGGC ATGAGCACCC TGTTCCTGGT GTACAGCAAC
3501  AAGTGCCAGA CCCCCCTGGG CATGGCCAGC GGCCACATCC GCGACTTCCA
3551  GATCACCGCC AGCGGCCAGT ACGGCCAGTG GGCTCCCAAG CTGGCCCGCC
3601  TGCACTACAG CGGCAGCATC AACGCCTGGT CGACCAAGGA GCCCTTCTCC
3651  TGGATCAAGG TGGACCTGCT GGCCCCCATG ATCATCCACG GCATCAAGAC
3701  CCAGGGCGCC CGCCAGAAGT TCAGCAGCCT GTACATCAGC CAGTTCATCA
3751  TCATGTACTC TCTAGACGGC AAGAAGTGGC AGACCTACCG CGGCAACAGC
3801  ACCGGCACCC TGATGGTGTT CTTCGGCAAC GTGGACAGCA GCGGCATCAA
3851  GCACAACATC TTCAACCCCC CCATCATCGC CCGCTACATC CGCCTGCACC
3901  CCACCCACTA CAGCATCCGC AGCACCCTGC GCATGGAGCT GATGGGCTGC
3951  GACCTGAACA GCTGCAGCAT GCCCCTGGGC ATGGAGAGCA AGGCCATCAG
4001  CGACGCCCAG ATCACCGCCT CCAGCTACTT CACCAACATG TTCGCCACCT
4051  GGAGCCCCAG CAAGGCCCGC CTGCACCTGC AGGGCCGCAG CAACGCCTGG
4101  CGCCCCCAGG TGAACAACCC CAAGGAGTGG CTGCAGGTGG ACTTCCAGAA
4151  AACCATGAAG GTGACTGGCG TGACCACCCA GGGCGTCAAG AGCCTGCTGA
4201  CCAGCATGTA CGTGAAGGAG TTCCTGATCA GCAGCAGCCA GGACGGCCAC
4251  CAGTGGACCC TGTTCTTCCA AAACGGCAAG GTGAAGGTGT TCCAGGGCAA
4301  CCAGGACAGC TTCACACCGG TCGTGAACAG CCTGGACCCC CCCCTGCTGA
4351  CCCGCTACCT GCGCATCCAC CCCCAGAGCT GGGTGCACCA GATCGCCCTG
4401  CGCATGGAGG TGCTGGGCTG CGAGGCCCAG GACCTGTACT GAAGCGGCCG
4451  C
```

Fig. 13B

HIGH LEVEL EXPRESSION OF PROTEINS

FILED OF THE INVENTION

The invention concerns genes and methods for expressing eukaryotic and viral proteins at high levels in eukaryotic cells.

BACKGROUND OF THE INVENTION

Expression of eukaryotic gene products in prokaryotes is sometimes limited by the presence of codons that are infrequently used in *E. coli*. Expression of such genes can be enhanced by systematic substitution of the endogenous codons with codons over represented in highly expressed prokaryotic genes (Robinson et al., Nucleic Acids Res. 12:6663, 1984). It is commonly supposed that rare codons cause pausing of the ribosome, which leads to a failure to complete the nascent polypeptide chain and a uncoupling of transcription and translation. Pausing of the ribosome is thought to lead to exposure of the 3' end of the mRNA to cellular ribonucleases.

SUMMARY OF THE INVENTION

The invention features a synthetic gene encoding a protein normally expressed in a mammalian cell or other eukaryotic cell wherein at least one non-preferred or less preferred codon in the natural gene encoding the protein has been replaced by a preferred codon encoding the same amino acid.

Preferred codons are: Ala (gcc); Arg (cgc); Asn (aac); Asp (gac) Cys (tgc); Gln (cag); Gly (ggc); His (cac); Ile (atc); Leu (ctg); Lys (aag); Pro (ccc); Phe (ttc); Ser (agc); Thr (acc); Tyr (tac); and Val (gtg). Less preferred codons are: Gly (ggg); Ile (att); Leu (ctc); Ser (tcc); Val (gtc); and Arg (agg). All codons which do not fit the description of preferred codons or less preferred codons are non-preferred codons. In general, the degree of preference of a particular codon is indicated by the prevalence of the codon in highly expressed human genes as indicated in Table 1 under the heading "High." For example, "atc" represents 77% of the Ile codons in highly expressed mammalian genes and is the preferred Ile codon; "att" represents 18% of the Ile codons in highly expressed mammalian genes and is the less preferred Ile codon. The sequence "ata" represents only 5% of the Ile codons in highly expressed human genes as is a non-preferred Ile codon. Replacing a codon with another codon that is more prevalent in highly expressed human genes will generally increase expression of the gene in mammalian cells. Accordingly, the invention includes replacing a less preferred codon with a preferred codon as well as replacing a non-preferred codon with a preferred or less preferred codon.

By "protein normally expressed in a mammalian cell" is meant a protein which is expressed in mammalian under natural conditions. The term includes genes in the mammalian genome such as those encoding Factor VIII, Factor IX, interleukins, and other proteins. The term also includes genes which are expressed in a mammalian cell under disease conditions such as oncogenes as well as genes which are encoded by a virus (including a retrovirus) which are expressed in mammalian cells post-infection. By "protein normally expressed in a eukaryotic cell" is meant a protein which is expressed in a eukaryote under natural conditions. The term also includes genes which are expressed in a mammalian cell under disease conditions.

In preferred embodiments, the synthetic gene is capable of expressing the mammalian or eukaryotic protein at a level which is at least 110%, 150%, 200%, 500%, 1,000%, 5,000% or even 10,000% of that expressed by the "natural" (or "native") gene in an in vitro mammalian cell culture system under identical conditions (i.e., same cell type, same culture conditions, same expression vector).

Suitable cell culture systems for measuring expression of the synthetic gene and corresponding natural gene are described below. Other suitable expression systems employing mammalian cells are well known to those skilled in the art and are described in, for example, the standard molecular biology reference works noted below. Vectors suitable for expressing the synthetic and natural genes are described below and in the standard reference works described below. By "expression" is meant protein expression. Expression can be measured using an antibody specific for the protein of interest. Such antibodies and measurement techniques are well known to those skilled in the art. By "natural gene" and "native gene" is meant the gene sequence (including naturally occurring allelic variants) which naturally encodes the protein, i.e., the native or natural coding sequence.

In other preferred embodiments at least 10%, 20%, 30%, 40%, 50%, 60%, 70%, 80%, or 90% of the codons in the natural gene are non-preferred codons.

In other preferred embodiments at least 10%, 20%, 30%, 40%, 50%, 60%, 70%, 80%, or 90% of the non-preferred codons in the natural gene are replaced with preferred codons or less preferred codons.

In other preferred embodiments at least 10%, 20%, 30%, 40%, 50%, 60%, 70%, 80%, or 90% of the non-preferred codons in the natural gene are replaced with preferred codons.

In a preferred embodiment the protein is a retroviral protein. In a more preferred embodiment the protein is a lentiviral protein. In an even more preferred embodiment the protein is an HIV protein. In other preferred embodiments the protein is gag, pol, env, gp120, or gp160. In other preferred embodiments the protein is a human protein. In more preferred embodiments, the protein is human Factor VIII and the protein in B region deleted human Factor VIII. In another preferred embodiment the protein is green flourescent protein.

In various preferred embodiments at least 30%, 40%, 50%, 60%, 70%, 80%, 90%, and 95% of the codons in the synthetic gene are preferred or less preferred codons.

The invention also features an expression vector comprising the synthetic gene.

In another aspect the invention features a cell harboring the synthetic gene. In various preferred embodiments the cell is a prokaryotic cell and the cell is a mammalian cell.

In preferred embodiments the synthetic gene includes fewer than 50, fewer than 40, fewer than 30, fewer than 20, fewer than 10, fewer than 5, or no "cg" sequences.

The invention also features a method for preparing a synthetic gene encoding a protein normally expressed by a mammalian cell or other eukaryotic cell. The method includes identifying non-preferred and less-preferred codons in the natural gene encoding the protein and replacing one or more of the non-preferred and less-preferred codons with a preferred codon encoding the same amino acid as the replaced codon.

Under some circumstances (e.g., to permit introduction of a restriction site) it may be desirable to replace a non-preferred codon with a less preferred codon rather than a preferred codon.

It is not necessary to replace all less preferred or non-preferred codons with preferred codons. Increased expression can be accomplished even with partial replacement of less preferred or non-preferred codons with preferred codons. Under some circumstances it may be desirable to only partially replace non-preferred codons with preferred or less preferred codons in order to obtain an intermediate level of expression.

In other preferred embodiments the invention features vectors (including expression vectors) comprising one or more the synthetic genes.

By "vector" is meant a DNA molecule, derived, e.g., from a plasmid, bacteriophage, or mammalian or insect virus, into which fragments of DNA may be inserted or cloned. A vector will contain one or more unique restriction sites and may be capable of autonomous replication in a defined host or vehicle organism such that the cloned sequence is reproducible. Thus, by "expression vector" is meant any autonomous element capable of directing the synthesis of a protein. Such DNA expression vectors include mammalian plasmids and viruses.

The invention also features synthetic gene fragments which encode a desired portion of the protein. Such synthetic gene fragments are similar to the synthetic genes of the invention except that they encode only a portion of the protein. Such gene fragments preferably encode at least 50, 100, 150, or 500 contiguous amino acids of the protein.

In constructing the synthetic genes of the invention it may be desirable to avoid CpG sequences as these sequences may cause gene silencing. Thus, in a preferred embodiment the coding region of the synthetic gene does not include the sequence "cg."

The codon bias present in the HIV gp120 env gene is also present in the gag and pol genes. Thus, replacement of a portion of the non-preferred and less preferred codons found in these genes with preferred codons should produce a gene capable of higher level expression. A large fraction of the codons in the human genes encoding Factor VIII and Factor IX are non-preferred codons or less preferred codons. Replacement of a portion of these codons with preferred codons should yield genes capable of higher level expression in mammalian cell culture.

The synthetic genes of the invention can be introduced into the cells of a living organism. For example, vectors (viral or non-viral) can be used to introduce a synthetic gene into cells of a living organism for gene therapy.

Conversely, it may be desirable to replace preferred codons in a naturally occurring gene with less-preferred codons as a means of lowering expression.

Standard reference works describing the general principles of recombinant DNA technology include Watson et al., *Molecular Biology of the Gene*, Volumes I and II, the Benjamin/Cummings Publishing Company, Inc., publisher, Menlo Park, Calif. (1987); Darnell et al., *Molecular Cell Biology*, Scientific American Books, Inc., Publisher, New York, N.Y. (1986); Old et al., *Principles of Gene Manipulation: An Introduction to Genetic Engineering*, 2d edition, University of California Press, publisher, Berkeley, Calif. (1981); Maniatis et al., *Molecular Cloning: A Laboratory Manual*, 2nd Ed. Cold Spring Harbor Laboratory, publisher, Cold Spring Harbor, N.Y. (1989); and *Current Protocols in Molecular Biology*, Ausubel et al., Wiley Press, New York, N.Y. (1992).

By "transformed cell" is meant a cell into which (or into an ancestor of which) has been introduced, by means of recombinant DNA techniques, a selected DNA molecule, e.g., a synthetic gene.

By "positioned for expression" is meant that a DNA molecule, e.g., a synthetic gene, is positioned adjacent to a DNA sequence which directs transcription and translation of the sequence (i.e., facilitates the production of the protein encoded by the synthetic gene.

DESCRIPTION OF THE DRAWINGS

FIG. 1 depicts the sequence of the synthetic gp120 (SEQ ID No.:34) and a synthetic gp160 gene (SEQ ID No.:35) in which codons have been replaced by those found in highly expressed human genes.

FIG. 6 is a comparison of the sequence of the wild-type ratTHY-1 gene (wt) (SEQ ID No.:37) and a synthetic ratTHY-1 gene (env) (SEQ ID No.:36) constructed by chemical synthesis and having the most prevalent codons found in the HIV-1 env gene.

FIG. 11 depicts the sequence of a synthetic gene encoding green flourescent proteins (SEQ ID NO:40).

FIG. 12 depicts the sequence of a native human Factor VIII gene lacking the central B domain (amino acids 760–1639, inclusive) (SEQ ID NO:41).

FIG. 13 depicts the sequence of a synthetic human Factor VIII gene lacking the central B domain (amino acids 760–1639, inclusive) (SEQ ID NO:42).

DESCRIPTION OF THE PREFERRED EMBODIMENTS

EXAMPLE 1

Construction of a Synthetic gp120 Gene Having Codons Found in Highly Expressed Human Genes A codon frequency table for the envelope precursor of the LAV subtype of HIV-1 was generated using software developed by the University of Wisconsin Genetics Computer Group. The results of that tabulation are contrasted in Table 1 with the pattern of codon usage by a collection of highly expressed human genes. For any amino acid encoded by degenerate codons, the most favored codon of the highly expressed genes is different from the most favored codon of the HIV envelope precursor. Moreover a simple rule describes the pattern of favored envelope codons wherever it applies: preferred codons maximize the number of adenine residues in the viral RNA. In all cases but one this means that the codon in which the third position is A is the most frequently used. In the special case of serine, three codons equally contribute one A residue to the mRNA; together these three comprise 85% of the serine codons actually used in envelope transcripts. A particularly striking example of the A bias is found in the codon choice for arginine, in which the AGA triplet comprises 88% of the arginine codons. In addition to the preponderance of A residues, a marked preference is seen for uridine among degenerate codons whose third residue must be a pyrimidine. Finally, the inconsistencies among the less frequently used variants can be accounted for by the observation that the dinucleotide CpG is under represented; thus the third position is less likely to be G whenever the second position is C, as in the codons for alanine, proline, serine and threonine; and the CGX triplets for arginine are hardly used at all.

TABLE 1

Codon Frequency in the HIV-1 IIIb env gene and in highly expressed human genes.

| | | | High | Env | | | | High | Env |
|---|---|---|---|---|---|---|---|---|---|
| Ala | | | | | Cys | | | | |
| GC | C | | 53 | 27 | TG | C | | 68 | 16 |
| | T | | 17 | 18 | | T | | 32 | 84 |
| | A | | 13 | 50 | Gln | | | | |
| | G | | 17 | 5 | CA | A | | 12 | 55 |
| Arg | | | | | | G | | 88 | 45 |
| CG | C | | 37 | 0 | Glu | | | | |
| | T | | 7 | 4 | GA | A | | 25 | 67 |
| | A | | 6 | 0 | | G | | 75 | 33 |
| | G | | 21 | 0 | Gly | | | | |
| AG | A | | 10 | 88 | GG | C | | 50 | 6 |
| | G | | 18 | 8 | | T | | 12 | 13 |
| Asn | | | | | | A | | 14 | 53 |
| AA | C | | 78 | 30 | | G | | 24 | 28 |
| | T | | 22 | 70 | His | | | | |
| Asp | | | | | CA | C | | 79 | 25 |
| GA | C | | 75 | 33 | | T | | 21 | 75 |
| | T | | 25 | 67 | Ile | | | | |
| Leu | | | | | AT | C | | 77 | 25 |
| CT | C | | 26 | 10 | | T | | 18 | 31 |
| | T | | 5 | 7 | | A | | 5 | 44 |
| | A | | 3 | 17 | Ser | | | | |
| | G | | 58 | 17 | TC | C | | 28 | 8 |
| TT | A | | 2 | 30 | | T | | 13 | 8 |
| | G | | 6 | 20 | | A | | 5 | 22 |
| Lys | | | | | | G | | 9 | 0 |
| AA | A | | 18 | 68 | AG | C | | 34 | 22 |
| | G | | 82 | 32 | | T | | 10 | 41 |
| Pro | | | | | Thr | | | | |
| CC | C | | 48 | 27 | AC | C | | 57 | 20 |
| | T | | 19 | 14 | | T | | 14 | 22 |
| | A | | 16 | 55 | | A | | 14 | 51 |
| | G | | 17 | 5 | | G | | 15 | 7 |

TABLE 1-continued

Codon Frequency in the HIV-1 IIIb env gene and in highly expressed human genes.

|     |   | High | Env |     |   | High | Env |
|-----|---|------|-----|-----|---|------|-----|
| Phe |   |      |     | Tyr |   |      |     |
| TT  | C | 80   | 26  | TA  | C | 74   | 8   |
|     | T | 20   | 74  |     | T | 26   | 92  |
|     |   |      |     | Val |   |      |     |
|     |   |      |     | GT  | C | 25   | 12  |
|     |   |      |     |     | T | 7    | 9   |
|     |   |      |     |     | A | 5    | 62  |
|     |   |      |     |     | G | 64   | 18  |

Codon frequency was calculated using the GCG program established the University of Wisconsin Genetics Computer Group. Numbers represent the percentage of cases in which the particular codon is used. Codon usage frequencies of envelope genes of other HIV-1 virus isolates are comparable and show a similar bias.

Figure 2:
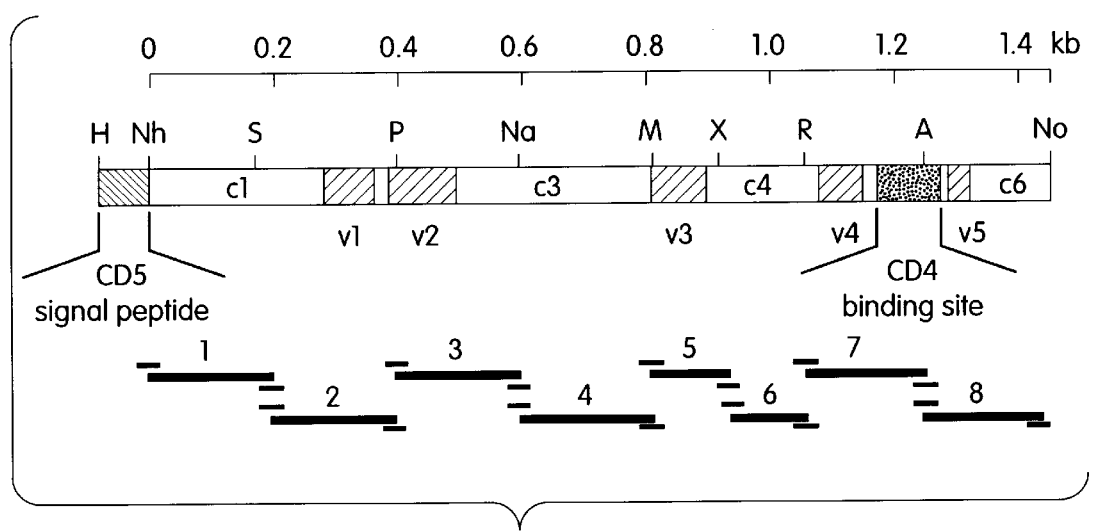
FIG. 2 is a schematic drawing of the synthetic gp120 (HIV-1 MN) gene. The shaded portions marked v1 to v5 indicate hypervariable regions. The filled box indicates the CD4 binding site. A limited number of the unique restriction sites ares shown: H (Hind3), Nh (Nhe1), P (Pst1), Na (Nae1), M (Mlu1), R (EcoR1), A (Age1) and No (Not1). The chemically synthesized DNA fragments which served as PCR templates are shown below the gp120 sequence, along with the locations of the primers used for their amplification.

In order to produce a gp120 gene capable of high level expression in mammalian cells, a synthetic gene encoding the gp120 segment of HIV-1 was constructed (syngp120mn), based on the sequence of the most common North American subtype, HIV-1 MN (Shaw et al., *Science* 226:1165, 1984; Gallo et al., *Nature* 321:119, 1986). In this synthetic gp120 gene nearly all of the native codons have been systematically replaced with codons most frequently used in highly expressed human genes (FIG. 1). This synthetic gene was assembled from chemically synthesized oligonucleotides of 150 to 200 bases in length. If oligonucleotides exceeding 120 to 150 bases are chemically synthesized, the percentage of full-length product can be low, and the vast excess of material consists of shorter oligonucleotides. Since these shorter fragments inhibit cloning and PCR procedures, it can be very difficult to use oligonucleotides exceeding a certain length. In order to use crude synthesis material without prior purification, single-stranded oligonucleotide pools were PCR amplified before cloning. PCR products were purified in agarose gels and used as templates in the next PCR step. Two adjacent fragments could be co-amplified because of overlapping sequences at the end of either fragment. These fragments, which were between 350 and 400 bp in size, were subcloned into a pCDM7-derived plasmid containing the leader sequence of the CD5 surface molecule followed by a Nhe1/Pst1/Mlu1/EcoR1/BamH1 polylinker. Each of the restriction enzymes in this polylinker represents a site that is present at either the 5' or 3' end of the PCR-generated fragments. Thus, by sequential subcloning of each of the 4 long fragments, the whole gp120gene was assembled. For each fragment three to six different clones were subcloned and sequenced prior to assembly. A schematic drawing of the method used to construct the synthetic gp120 is shown in FIG. 2. The sequence of the synthetic gp120 gene (and a synthetic gp160 gene created using the same approach) is presented in FIG. 1.

The mutation rate was considerable. The most commonly found mutations were short (1 nucleotide) and long (up to 30 nucleotides) deletions. In some cases it was necessary to exchange parts with either synthetic adapters or pieces from other subclones without mutation in that particular region. Some deviations from strict adherence to optimized codon usage were made to accommodate the introduction of restriction sites into the resulting gene to facilitate the replacement of various segments (FIG. 2). These unique restriction sites were introduced into the gene at approximately 100 bp intervals. The native HIV leader sequence was exchanged with the highly efficient leader peptide of the human CD5 antigen to facilitate secretion (Aruffo et al., *Cell* 61:1303, 1990) The plasmid used for construction is a derivative of the mammalian expression vector pCDM7 transcribing the inserted gene under the control of a strong human CMV immediate early promoter.

To compare the wild-type and synthetic gp120 coding sequences, the synthetic gp120 coding sequence was inserted into a mammalian expression vector and tested in transient transfection assays. Several different native gp120 genes were used as controls to exclude variations in expression levels between different virus isolates and artifacts induced by distinct leader sequences. The gp120 HIV IIIb construct used as control was generated by PCR using a Sal1/Xho1 HIV-1 HXB2 envelope fragment as template. To exclude PCR induced mutations, a Kpn1/Ear1 fragment containing approximately 1.2 kb of the gene was exchanged with the respective sequence from the proviral clone. The wild-type gp120mn constructs used as controls were cloned by PCR from HIV-1 MN infected C8166 cells (AIDS Repository, Rockville, Md.) and expressed gp120 either with a native envelope or a CD5 leader sequence. Since proviral clones were not available in this case, two clones of each construct were tested to avoid PCR artifacts. To determine the amount of secreted gp120 semi-quantitatively supernatants of 293T cells transiently transfected by calcium phosphate co-precipitation were immunoprecipitated with soluble CD4:immunoglobulin fusion protein and protein A sepharose.

Figure 3:
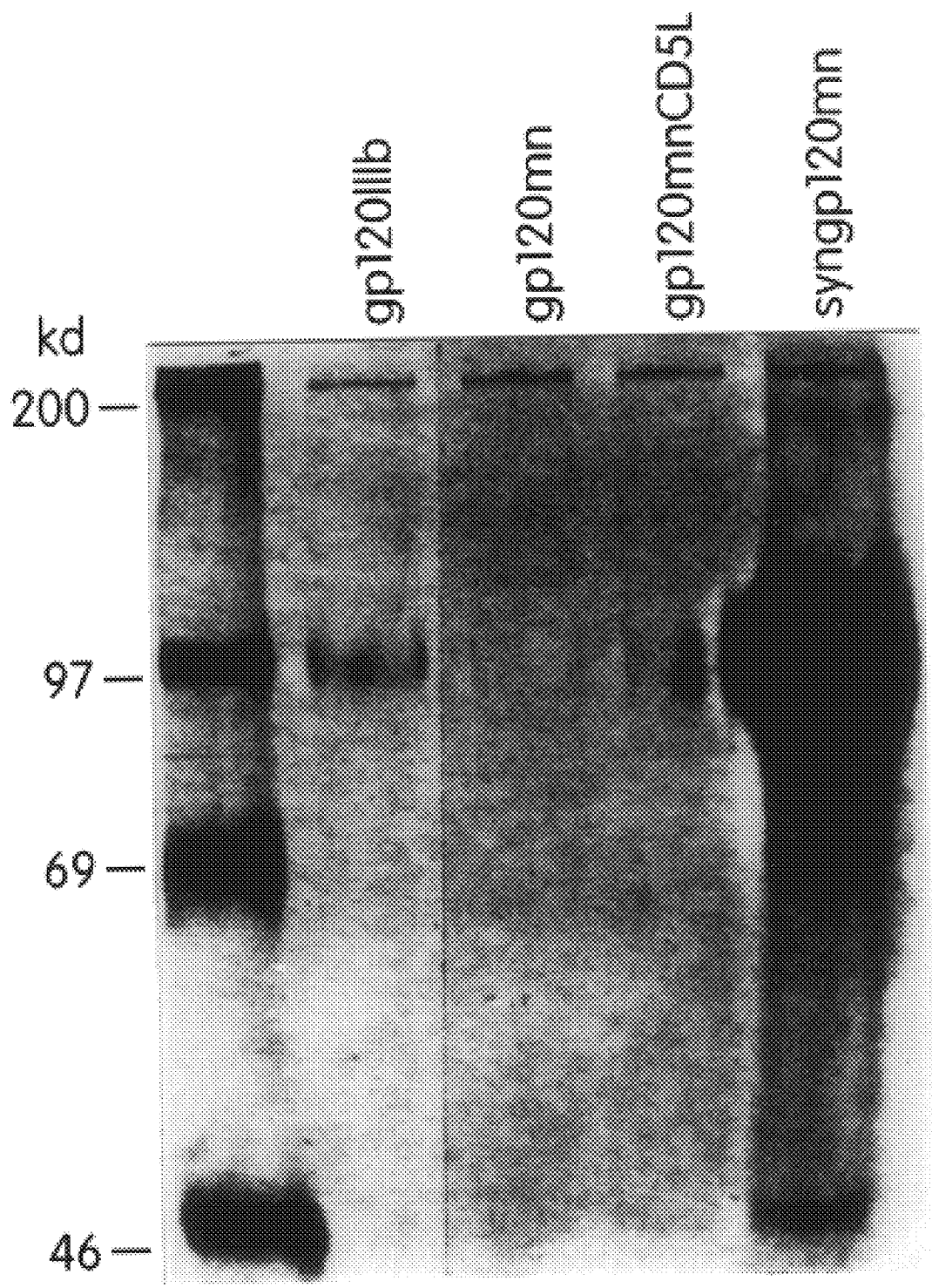
FIG. 3 is a photograph of the results of transient transfection assays used to measure gp120 expression. Gel electrophoresis of immunoprecipitated supernatants of 293T cells transfected with plasmids expressing gp120 encoded by the IIIB isolate of HIV-1 (gp120IIIb), by the MN isolate of HIV-1 (gp120mn), by the MN isolate of HIV-1 modified by substitution of the endogenous leader peptide with that of the CD5 antigen (gp120mnCD5L), or by the chemically synthesized gene encoding the MN variant of HIV-1 with the human CD5Leader (syngp120mn). Supernatants were harvested following a 12 hour labeling period 60 hours post-transfection and immunoprecipitated with CD4:IgG1 fusion protein and protein A sepharose.

The results of this analysis (FIG. 3) show that the synthetic gene product is expressed at a very high level compared to that of the native gp120 controls. The molecular weight of the synthetic gp120 gene was comparable to control proteins (FIG. 3) and appeared to be in the range of 100 to 110 kd. The slightly faster migration can be explained by the fact that in some tumor cell lines, e.g., 293T, glycosylation is either not complete or altered to some extent.

Figure 4:
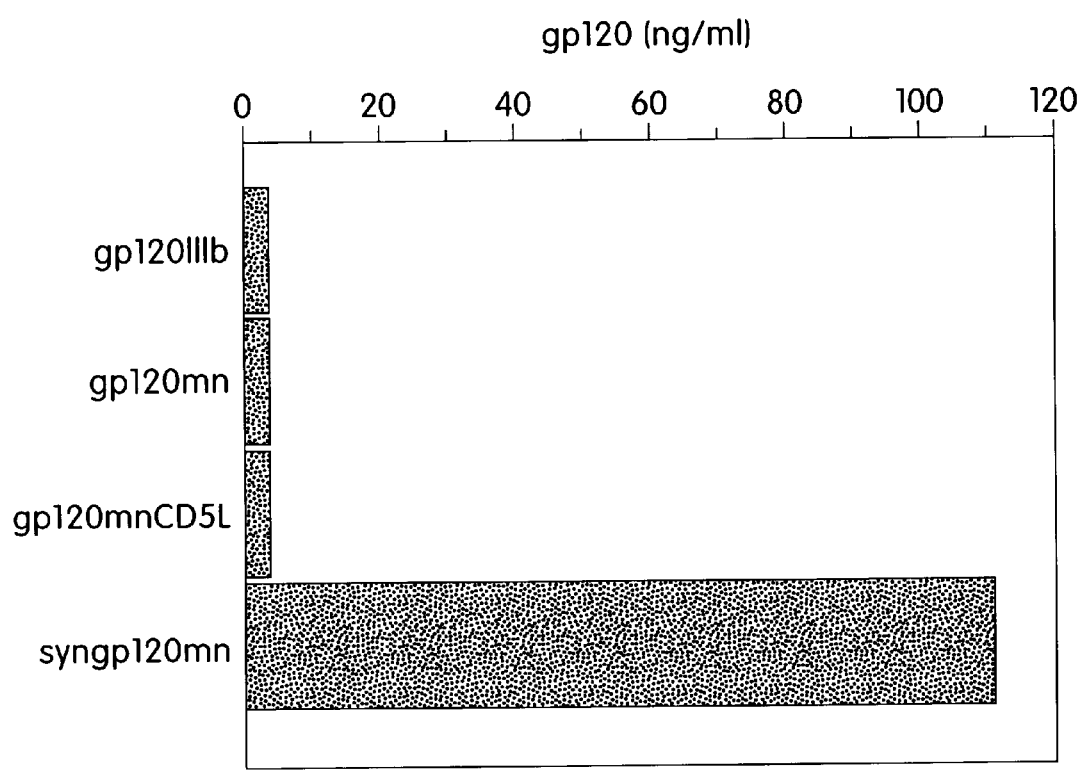
FIG. 4 is a graph depicting the results of ELISA assays used to measure protein levels in supernatants of transiently transfected 293T cells. Supernatants of 293T cells transfected with plasmids expressing gp120 encoded by the IIIB isolate of HIV-1 (gp120 IIIb), by the MN isolate of HIV-1 (gp120mn), by the MN isolate of HIV-1 modified by substitution of the endogenous leader peptide with that of CD5 antigen (gp120mn CD5L), or by the chemically synthesized gene encoding the MN variant of HIV-1 with human CDS leader (syngp120mn) were harvested after 4 days and tested in a gp120/CD4 ELISA. The level of gp120 is expressed in ng/ml.

To compare expression more accurately gp120 protein levels were quantitated using a gp120 ELISA with CD4 in the demobilized phase. This analysis shows (FIG. 4) that ELISA data were comparable to the immunoprecipitation data, with a gp120 concentration of approximately 125 ng/ml for the synthetic gp120 gene, and less than the background cutoff (5 ng/ml) for all the native gp120 genes. Thus, expression of the synthetic gp120 gene appears to be at least one order of magnitude higher than wild-type gp120 genes. In the experiment shown the increase was at least 25 fold.

The Role of Rev in gp120 Expression

Since rev appears to exert its effect at several steps in the expression of a viral transcript, the possible role of non-translational effects in the improved expression of the synthetic gp120 gene was tested. First, to rule out the possibility that negative signals elements conferring either increased mRNA degradation or nucleic retention were eliminated by changing the nucleotide sequence, cytoplasmic mRNA levels were tested. Cytoplasmic RNA was prepared by NP40 lysis of transiently transfected 293T cells and subsequent elimination of the nuclei by centrifugation. Cytoplasmic RNA was subsequently prepared from lysates by multiple phenol extractions and precipitation, spotted on nitrocellulose using a slot blot apparatus, and finally hybridized with an envelope-specific probe.

Briefly, cytoplasmic mRNA 293 cells transfected with CDM&, gp120 IIIB, or syngp120was isolated 36 hours post transfection. Cytoplasmic RNA of Hela cells infected with wild-type vaccinia virus or recombinant virus expressing gp120 IIIb or the synthetic gp120 gene was under the control of the 7.5 promoter was isolated 16 hours post infection. Equal amounts were spotted on nitrocellulose using a slot blot device and hybridized with randomly labeled 1.5 kb gp120IIIb and syngp120 fragments or human beta-actin. RNA expression levels were quantitated by scanning the hybridized membranes with a phospoimager. The procedures used are described in greater detail below.

This experiment demonstrated that there was no significant difference in the mRNA levels of cells transfected with either the native or synthetic gp120 gene. In fact, in some experiments cytoplasmic mRNA level of the synthetic gp120 gene was even lower than that of the native gp120 gene.

These data were confirmed by measuring expression from recombinant vaccinia viruses. Human 293 cells or Hela cells were infected with vaccinia virus expressing wild-type gp120 IIIb or syngp120mn at a multiplicity of infection of at least 10. Supernatants were harvested 24 hours post infection and immunoprecipitated with CD4:immunoglobin fusion protein and protein A sepharose. The procedures used in this experiment are described in greater detail below.

This experiment showed that the increased expression of the synthetic gene was still observed when the endogenous gene product and the synthetic gene product were expressed from vaccinia virus recombinants under the control of the strong mixed early and late 7.5 k promoter. Because vaccinia virus mRNAs are transcribed and translated in the cytoplasm, increased expression of the synthetic envelope gene in this experiment cannot be attributed to improved export from the nucleus. This experiment was repeated in two additional human cell types, the kidney cancer cell line 293 and HeLa cells. As with transfected 293T cells, mRNA levels were similar in 293 cells infected with either recombinant vaccinia virus.

Codon Usage in Lentivirus

Because it appears that codon usage has a significant impact on expression in mammalian cells, the codon frequency in the envelope genes of other retroviruses was examined. This study found no clear pattern of codon preference between retroviruses in general. However, if viruses from the lentivirus genus, to which HIV-1 belongs to, were analyzed separately, codon usage bias almost identical to that of HIV-1 was found. A codon frequency table from the envelope glycoproteins of a variety of (predominantly type C) retroviruses excluding the lentiviruses was prepared, and compared a codon frequency table created from the envelope sequences of four lentiviruses not closely related to HIV-1 (caprine arthritis encephalitis virus, equine infectious anemia virus, feline immunodeficiency virus, and visna virus) (Table 2). The codon usage pattern for lentiviruses is strikingly similar to that of HIV-1, in all cases but one, the preferred codon for HIV-1 is the same as the preferred codon for the other lentiviruses. The exception is proline, which is encoded by CCT in 41% of non-HIV lentiviral envelope residues, and by CCA in 40% of residues, a situation which clearly also reflects a significant preference for the triplet ending in A. The pattern of codon usage by the non-lentiviral envelope proteins does not show a similar predominance of A residues, and is also not as skewed toward third position C and G residues as is the codon usage for the highly expressed human genes. In general non-lentiviral retroviruses appear to exploit the different codons more equally, a pattern they share with less highly expressed human genes.

TABLE 2

Codon frequency in the envelope gene of lentiviruses (lenti) and non-lentiviral retroviruses (other)

|  |  | Other | Lenti |  |  | Other | Lenti |
|---|---|---|---|---|---|---|---|
| Ala |  |  |  | Cys |  |  |  |
| GC | C | 45 | 13 | TG | C | 53 | 21 |
|  | T | 26 | 37 |  | T | 47 | 79 |
|  | A | 20 | 46 | Gln |  |  |  |
|  | G | 9 | 3 | CA | A | 52 | 69 |
| Arg |  |  |  |  | G | 48 | 31 |
| CG | C | 14 | 2 | Glu |  |  |  |
|  | T | 6 | 3 | GA | A | 57 | 68 |
|  | A | 16 | 5 |  | G | 43 | 32 |
|  | G | 17 | 3 | Gly |  |  |  |
| AG | A | 31 | 51 | GG | C | 21 | 8 |
|  | G | 15 | 26 |  | T | 13 | 9 |
| Asn |  |  |  |  | A | 37 | 56 |
| AA | C | 49 | 31 |  | G | 29 | 26 |
|  | T | 51 | 69 | His |  |  |  |
| Asp |  |  |  | CA | C | 51 | 38 |
| GA | C | 55 | 33 |  | T | 49 | 62 |
|  | T | 51 | 69 | Ile |  |  |  |
| Leu |  |  |  | AT | C | 38 | 16 |
| CT | C | 22 | 8 |  | T | 31 | 22 |
|  | T | 14 | 9 |  | A | 31 | 61 |
|  | A | 21 | 16 | Ser |  |  |  |
|  | G | 19 | 11 | TC | C | 38 | 10 |
| TT | A | 15 | 41 |  | T | 17 | 16 |
|  | G | 10 | 16 |  | A | 18 | 24 |
| Lys |  |  |  |  | G | 6 | 5 |
| AA | A | 60 | 63 | AG | C | 13 | 20 |
|  | G | 40 | 37 |  | T | 7 | 25 |
| Pro |  |  |  | Thr |  |  |  |
| CC | C | 42 | 14 | AC | C | 44 | 18 |
|  | T | 30 | 41 |  | T | 27 | 20 |
|  | A | 20 | 40 |  | A | 19 | 55 |
|  | G | 7 | 5 |  | G | 10 | 8 |
| Phe | Tyr |  |  |  |  |  |  |
| TT | C | 52 | 25 | TA | C | 48 | 28 |
|  | T | 48 | 75 |  |  |  |  |
|  |  |  |  |  | T | 52 | 72 |
|  |  |  |  | Val |  |  |  |
|  |  |  |  | GT | C | 36 | 9 |
|  |  |  |  |  | T | 17 | 10 |
|  |  |  |  |  | A | 22 | 54 |
|  |  |  |  |  | G | 25 | 27 |

Codon frequency was calculated using the GCG program established by the University of Wisconsin Genetics Computer Group. Numbers represent the percentage in which a particular codon is used. Codon usage of non-lentiviral retroviruses was compiled from the envelope precursor sequences of bovine leukemia virus feline leukemia virus, human T-cell leukemia virus type I, human T-cell lymphotropic virus type II, the mink cell focus-forming isolate of murine leukemia virus (MuLV), the Rauscher spleen focus-forming isolate, the 10A1 isolate, the 4070A amphotropic isolate and the myeloproliferative leukemia virus isolate, and from rat leukemia virus, simian sarcoma virus, simian T-cell leukemia virus, leukemogenic retrovirus T1223/B and gibbon ape leukemia virus. The codon frequency tables for the non-HIV, non-SIV lentiviruses were compiled from the envelope precursor sequences for caprine arthritis encephalitis virus, equine infectious anemia virus, feline immunodeficiency virus, and visna virus.

In addition to the prevalence of codons containing an A, lentiviral codons adhere to the HIV pattern of strong CpG under representation, so that the third position for alanine, proline, serine and threonine triplets is rarely G. The retroviral envelope triplets show a similar, but less pronounced, under representation of CpG. The most obvious difference between lentiviruses and other retroviruses with respect to CpG prevalence lies in the usage of the CGX variant of arginine triplets, which is reasonably frequently represented among the retroviral envelope coding sequences, but is almost never present among the comparable lentivirus sequences.

Differences in Rev Dependence Between Native and Synthetic gp120

To examine whether regulation by rev is connected to HIV-1 codon usage, the influence of rev on the expression of both native and synthetic gene was investigated. Since regulation by rev requires the rev-binding site RRE in cis, constructs were made in which this binding site was cloned into the 3' untranslated region of both the native and the synthetic gene. These plasmids were co-transfected with rev or a control plasmid in trans into 293T cells, and gp120 expression levels in supernatants were measured semiquantitatively by immunoprecipitation. The procedures used in this experiment are described in greater detail below.

Figure 5A:
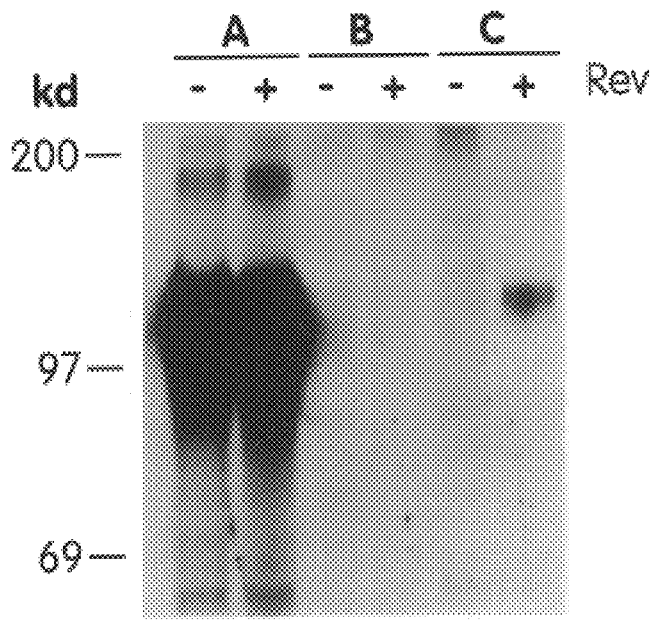
FIG. 5A is a photograph of a gel illustrating the results of a immunoprecipitation assay used to measure expression of the native and synthetic gp120 in the presence of rev in trans and the RRE in cis. In this experiment 293T cells were transiently transfected by calcium phosphate co-precipitation of 10 μg of plasmid expressing: (A) the synthetic gp120MN sequence and RRE in cis, (B) the gp120 portion of HIV-1 IIIB, (C) the gp120 portion of HIV-1 IIIB and RRE in cis, all in the presence or absence of rev expression. The RRE constructs gp120IIIbRRE and syngp120mnRRE were generated using an Eag1/Hpa1RRE fragment cloned by PCR from a HIV-1 HXB2 proviral clone. Each gp120 expression plasmid was cotransfected with 10 μg of either pCMVrev or CDM7 plasmid DNA. Supernatants were harvested 60 hours post transfection, immunoprecipitated with CD4:IgG fusion protein and protein A agarose, and run on a 7% reducing SDS-PAGE. The gel exposure time was extended to allow the induction of gp120IIIbrre by rev to be demonstrated.
Figure 5B:
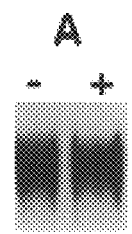
FIG. 5B is a shorter exposure of a similar experiment in which syngp120mnrre was cotransfected with or without pCMVrev.
Figure 5C:
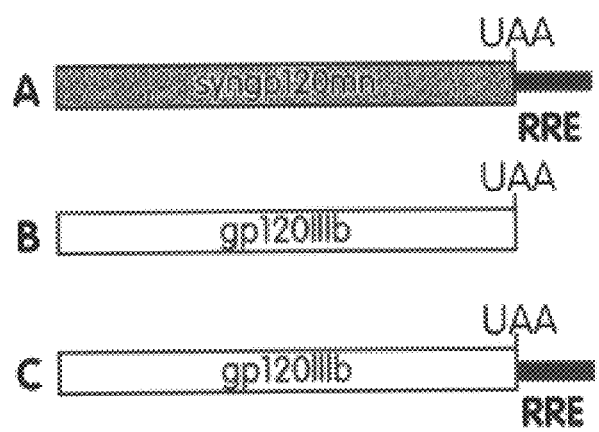
FIG. 5C is a schematic diagram of the constructs used in FIG. 5A.
Figure 7:
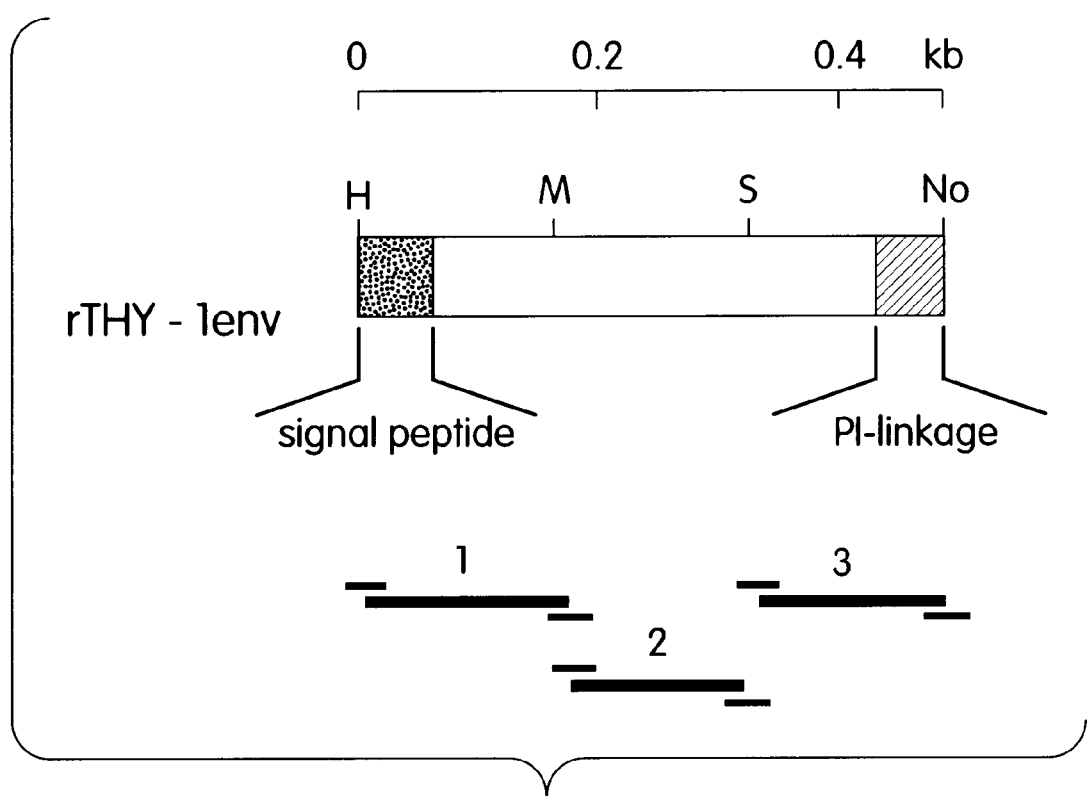
FIG. 7 is a schematic diagram of the synthetic ratTHY-1 gene. The solid black box denotes the signal peptide. The shaded box denotes the sequences in the precursor which direct the attachment of a phophatidyl-inositol glycan anchor. Unique restriction sites used for assembly of the THY-1 constructs are marked H (Hind3), M (Mlu1), S (Sac1) and No (Not1). The position of the synthetic oligonucleotides employed in the construction are shown at the bottom of the figure.
Figure 8:
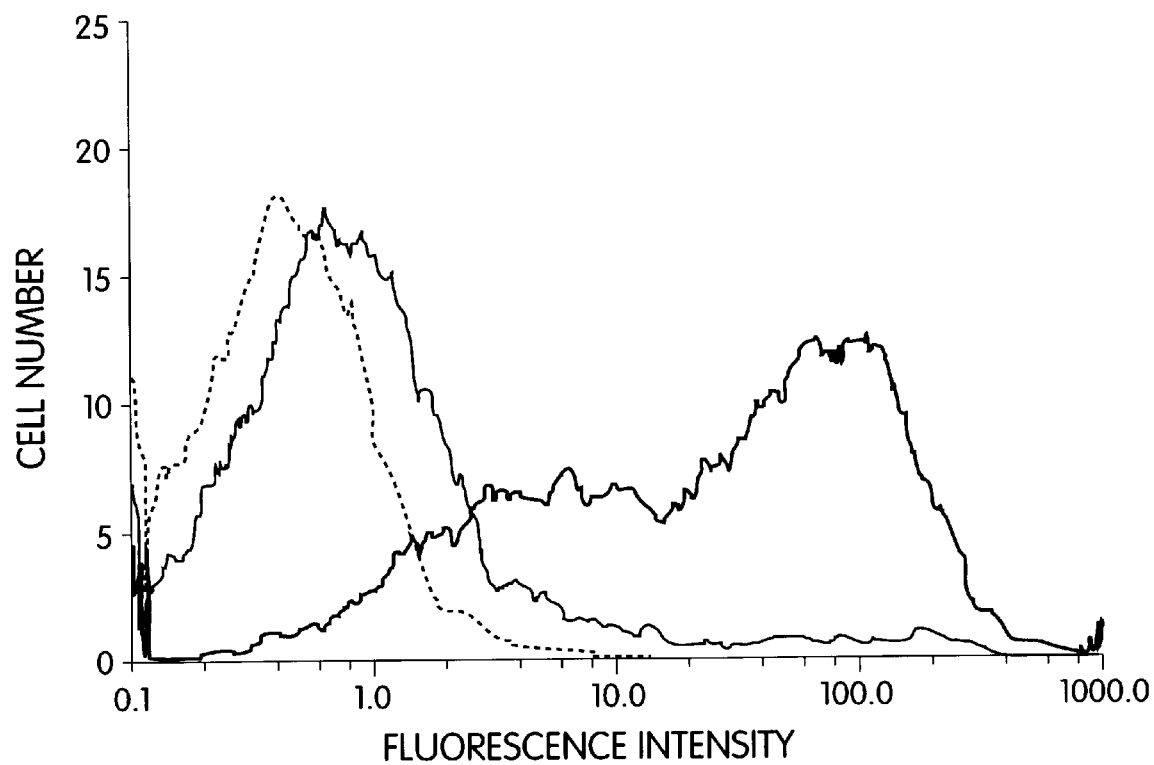
FIG. 8 is a graph depicting the results of flow cytometry analysis. In this experiment 293T cells transiently transfected with either a wild-type ratTHY-1 expression plasmid (thick line), ratTHY-1 with envelope codons expression plasmid (thin line), or vector only (dotted line) by calcium phosphate co-precipitation. Cells were stained with anti-ratTHY-1 monoclonal antibody OX7 followed by a polyclonal FITC-conjugated anti-mouse IgG antibody 3 days after transfection.
Figure 9A:
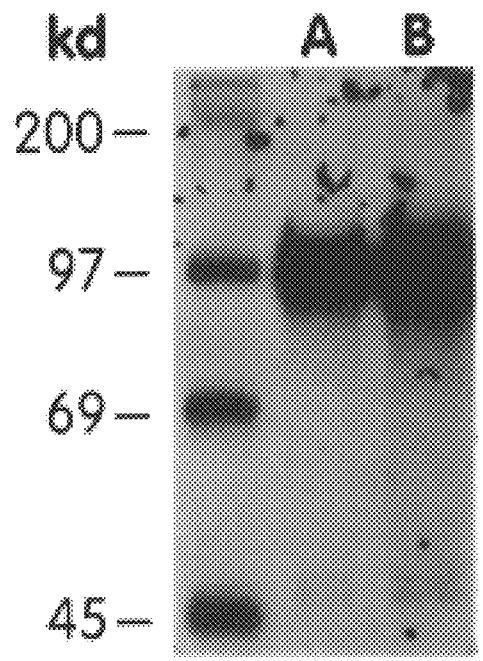
FIG. 9A is a photograph of a gel illustrating the results of immunoprecipitation analysis of supernatants of human 293T cells transfected with either syngp120mn (A) or a construct syngp120mn.rTHY-1env which has the rTHY-1env gene in the 3' untranslated region of the syngp120mn gene (B). The syngp120mn.rTHY-1env construct was generated by inserting a Not1 adapter into the blunted Hind3 site of the rTHY-1env plasmid. Subsequently, a 0.5 kb Not1 fragment containing the rTHY-1env gene was cloned into the Not1 site of the syngp120mn plasmid and tested for correct orientation. Supernatants of $^{35}$S labeled cells were harvested 72 hours post transfection, precipitated with CD4:IgG fusion protein and protein A agarose, and run on a 7% reducing SDS-PAGE.
Figure 9B:
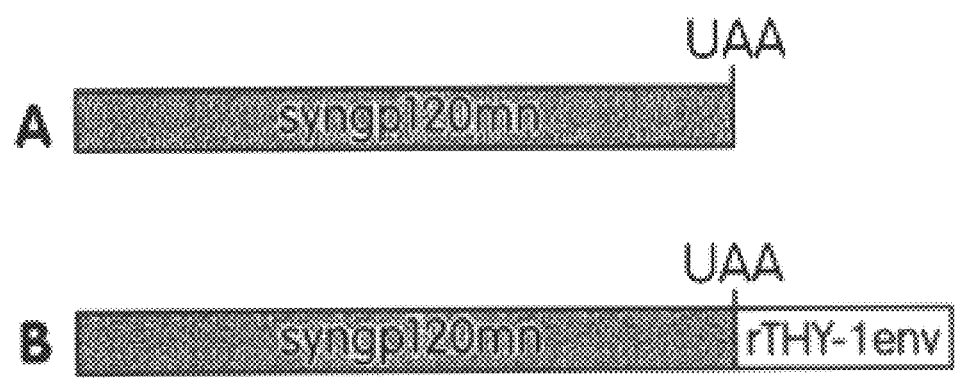
FIG. 9B is a schematic diagram of the constructs used in the experiment depicted in FIG. 9A.

As shown in FIG. 5A and FIG. 5B, rev up regulates the native gp120 gene, but has no effect on the expression of the synthetic gp120gene. Thus, the action of rev is not apparent on a substrate which lacks the coding sequence of endogenous viral envelope sequences.

Expression of a Synthetic ratTHY-1 Gene with HIV Envelope Codons

The above-described experiment suggest that in fact "envelope sequences" have to be present for rev regulation. In order to test this hypothesis, a synthetic version of the gene encoding the small, typically highly expressed cell surface protein, ratTHY-1 antigen, was prepared. The synthetic version of the ratTHY-1 gene was designed to have a codon usage like that of HIV gp120. In designing this synthetic gene AUUUA sequences, which are associated with mRNA instability, were avoided. In addition, two restriction sites were introduced to simplify manipulation of the resulting gene (FIG. 6). This synthetic gene with the HIV envelope codon usage (rTHY-1env) was generated using three 150 to 170 mer oligonucleotides (FIG. 7). In contrast to the syngp120mn gene, PCR products were directly cloned and assembled in pUC12, and subsequently cloned into pCDM7.

Expression levels of native rTHY-1 and rTHY-1 with the HIV envelope codons were quantitated by immunofluorescence of transiently transfected 293T cells. FIG. 8 shows that the expression of the native THY-1 gene is almost two orders of magnitude above the background level of the control transfected cells (pCDM7). In contrast, expression of the synthetic ratTHY-1 is substantially lower than that of the native gene (shown by the shift to of the peak towards a lower channel number).

To prove that no negative sequence elements promoting mRNA degradation were inadvertently introduced, a construct was generated in which the rTHY-1env gene was cloned at the 3' end of the synthetic gp120 gene (FIG. 9B). In this experiment 293T cells were transfected with either the syngp120mn gene or the syngp120/ratTHY-1 env fusion gene (syngp120mn.rTHY-1env). Expression was measured by immunoprecipitation with CD4:IgG fusion protein and protein A agarose. The procedures used in this experiment are described in greater detail below.

Since the synthetic gp120 gene has an UAG stop codon, rTHY-1env is not translated from this transcript. If negative elements conferring enhanced degradation were present in the sequence, gp120 protein levels expressed from this construct should be decreased in comparison to the syngp120mn construct without rTHY-1env. FIG. 9A, shows that the expression of both constructs is similar, indicating that the low expression must be linked to translation.

Rev-dependent Expression of Synthetic ratTHY-1 Gene with Envelope Codons

To explore whether rev is able to regulate expression of a ratTHY-1 gene having env codons, a construct was made with a rev-binding site in the 3' end of the rTHY1env open reading frame. To measure rev-responsiveness of the a ratTHY-1env construct having a 3' RRE, human 293T cells were cotransfected ratTHY-1envrre and either CDM7 or pCMVrev. At 60 hours post transfection cells were detached with 1 mM EDTA in PBS and stained with the OX-7 anti rTHY-1 mouse monoclonal antibody and a secondary FITC-conjugated antibody. Fluorescence intensity was measured using a EPICS XL cytofluorometer. These procedures are described in greater detail below.

In repeated experiments, a slight increase of rTHY-1env expression was detected if rev was cotransfected with the rTHY-1env gene. To further increase the sensitivity of the assay system a construct expressing a secreted version of rTHY-1env was generated. This construct should produce more reliable data because the accumulated amount of secreted protein in the supernatant reflects the result of protein production over an extended period, in contrast to surface expressed protein, which appears to more closely reflect the current production rate. A gene capable of expressing a secreted form was prepared by PCR using forward and reverse primers annealing 3' of the endogenous leader sequence and 5' of the sequence motif required for phosphatidylinositol glycan anchorage respectively. The PCR product was cloned into a plasmid which already contained a CD5 leader sequence, thus generating a construct in which the membrane anchor has been deleted and the leader sequence exchanged by a heterologous (and probably more efficient) leader peptide.

The rev-responsiveness of the secreted form ratTHY-1env was measured by immunoprecipitation of supernatants of human 293T cells cotransfected with a plasmid expressing a secreted form of ratTHY-1env and the RRE sequence in cis (rTHY-1envPI-rre) and either CDM7 or pCMVrev. The rTHY-1envPI-RRE construct was made by PCR using the oligonucleotide: cgcggggctagcgcaaagagtaataagtttaac (SEQ ID NO:38) as a forward primer, the oligonucleotide: cgcggatcccttgtattttgtactaata (SEQ ID NO:39) as reverse primer, and the synthetic rTHY-1env construct as a template. After digestion with Nhe1 and Not1 the PCR fragment was cloned into a plasmid containing CD5 leader and RRE sequences. Supernatants of $^{35}S$ labeled cells were harvested 72 hours post transfection, precipitated with a mouse monoclonal antibody OX7 against rTHY-1 and anti mouse IgG sepharose, and run on a 12% reducing SDS-PAGE.

In this experiment the induction of rTHY-1env by rev was much more prominent and clear-cut than in the above-described experiment and strongly suggests that rev is able to translationally regulate transcripts that are suppressed by low-usage codons.

Rev-independent Expression of a rTHY-1env:immunoglobulin Fusion Protein

To test whether low-usage codons must be present throughout the whole coding sequence or whether a short region is sufficient to confer rev-responsiveness, a rTHY-1env:immunoglobulin fusion protein was generated. In this construct the rTHY-1env gene (without the sequence motif responsible for phosphatidylinositol glycan anchorage) is linked to the human IgG1 hinge, CH2 and CH3 domains. This construct was generated by anchor PCR using primers with Nhe1 and BamHI restriction sites and rTHY-1env as template. The PCR fragment was cloned into a plasmid containing the leader sequence of the CD5 surface molecule and the hinge, CH2 and CH3 parts of human IgG1 immunoglobulin. A Hind3/Eag1 fragment containing the rTHY-1envegl insert was subsequently cloned into a pCDM7-derived plasmid with the RRE sequence.

To measure the response of the rTHY-1env/ immunoglobin fusion gene (rTHY-1enveg1rre) to rev human 293T cells cotransfected with rTHY-1enveg1rre and either pCDM7 or pCMVrev. The rTHY-1enveg1rre construct was made by anchor PCR using forward and reverse primers with Nhe1 and BamH1 restriction sites respectively. The PCR fragment was cloned into a plasmid containing a CD5 leader and human IgG1 hinge, CH2 and CH3 domains. Supernatants of $^{35}$S labeled cells were harvested 72 hours post transfection, precipitated with a mouse monoclonal antibody OX7 against rTHY-1 and anti mouse IgG sepharose, and run on a 12% reducing SDS-PAGE. The procedures used are described in greater detail below.

As with the product of the rTHY-1envPI- gene, this rTHY-1env/immunoglobulin fusion protein is secreted into the supernatant. Thus, this gene should be responsive to rev-induction. However, in contrast to rTHY-1envPI-, cotransfection of rev in trans induced no or only a negligible increase of rTHY-1enveg1 expression.

The expression of rTHY-1:immunoglobulin fusion protein with native rTHY-1 or HIV envelope codons was measured by immunoprecipitation. Briefly, human 293T cells transfected with either rTHY-1enveg1 (env codons) or rTHY-1wteg1 (native codons). The rTHY-1wteg1 construct was generated in manner similar to that used for the rTHY-1enveg1 construct, with the exception that a plasmid containing the native rTHY-1 gene was used as template. Supernatants of $^{35}$S labeled cells were harvested 72 hours post transfection, precipitated with a mouse monoclonal antibody OX7 against rTHY-1 and anti mouse IgG sepharose, and run on a 12% reducing SDS-PAGE. THE procedures used in this experiment are described in greater detail below.

Expression levels of rTHY-1enveg1 were decreased in comparison to a similar construct with wild-type rTHY-1 as the fusion partner, but were still considerably higher than rTHY-1env. Accordingly, both parts of the fusion protein influenced expression levels. The addition of rTHY-1env did not restrict expression to an equal level as seen for rTHY-1env alone. Thus, regulation by rev appears to be ineffective if protein expression is not almost completely suppressed.

Codon Preference in HIV-1 Envelope Genes

Direct comparison between codon usage frequency of HIV envelope and highly expressed human genes reveals a striking difference for all twenty amino acids. One simple measure of the statistical significance of this codon preference is the finding that among the nine amino acids with two fold codon degeneracy, the favored third residue is A or U in all nine. The probability that all nine of two equiprobable choices will be the same is approximately 0.004, and hence by any conventional measure the third residue choice cannot be considered random. Further evidence of a skewed codon preference is found among the more degenerate codons, where a strong selection for triplets bearing adenine can be seen. This contrasts with the pattern for highly expressed genes, which favor codons bearing C, or less commonly G, in the third position of codons with three or more fold degeneracy.

The systematic exchange of native codons with codons of highly expressed human genes dramatically increased expression of gp120. A quantitative analysis by ELISA showed that expression of the synthetic gene was at least 25 fold higher in comparison to native gp120 after transient transfection into human 293 cells. The concentration levels in the ELISA experiment shown were rather low. Since an ELISA was used for quantification which is based on gp120 binding to CD4, only native, non-denatured material was detected. This may explain the apparent low expression. Measurement of cytoplasmic mRNA levels demonstrated that the difference in protein expression is due to translational differences and not mRNA stability.

Retroviruses in general do not show a similar preference towards A and T as found for HIV. But if this family was divided into two subgroups, lentiviruses and non-lentiviral retroviruses, a similar preference to A and, less frequently, T, was detected at the third codon position for lentiviruses. Thus, the availing evidence suggests that lentiviruses retain a characteristic pattern of envelope codons not because of an inherent advantage to the reverse transcription or replication of such residues, but rather for some reason peculiar to the physiology of that class of viruses. The major difference between lentiviruses and non-complex retroviruses are additional regulatory and non-essentially accessory genes in lentiviruses, as already mentioned. Thus, one simple explanation for the restriction of envelope expression might be that an important regulatory mechanism of one of these additional molecules is based on it. In fact, it is known that one of these proteins, rev, which most likely has homologues in all lentiviruses. Thus codon usage in viral mRNA is used to create a class of transcripts which is susceptible to the stimulatory action of rev. This hypothesis was proved using a similar strategy as above, but this time codon usage was changed into the inverse direction. Codon usage of a highly expressed cellular gene was substituted with the most frequently used codons in the HIV envelope. As assumed, expression levels were considerably lower in comparison to the native molecule, almost two orders of magnitude when analyzed by immunofluorescence of the surface expressed molecule. If rev was coexpressed in trans and a RRE element was present in cis only a slight induction was found for the surface molecule. However, if THY-1 was expressed as a secreted molecule, the induction by rev was much more prominent, supporting the above hypothesis. This can probably be explained by accumulation of secreted protein in the supernatant, which considerably amplifies the rev effect. If rev only induces a minor increase for surface molecules in general, induction of HIV envelope by rev cannot have the purpose of an increased surface abundance, but rather of an increased intracellular gp160 level. It is completely unclear at the moment why this should be the case.

To test whether small subtotal elements of a gene are sufficient to restrict expression and render it rev-dependent rTHY1env:immunoglobulin fusion proteins were generated, in which only about one third of the total gene had the envelope codon usage. Expression levels of this construct were on an intermediate level, indicating that the rTHY-1env negative sequence element is not dominant over the immunoglobulin part. This fusion protein was not or only slightly rev-responsive, indicating that only genes almost completely suppressed can be rev-responsive.

Another characteristic feature that was found in the codon frequency tables is a striking under representation of CpG triplets. In a comparative study of codon usage in *E. coli*, yeast, drosophila and primates it was shown that in a high number of analyzed primate genes the 8 least used codons contain all codons with the CpG dinucleotide sequence. Avoidance of codons containing this dinucleotide motif was also found in the sequence of other retroviruses. It seems plausible that the reason for under representation of CpG-bearing triplets has something to do with avoidance of gene silencing by methylation of CpG cytosines. The expected number of CpG dinucleotides for HIV as a whole is about one fifth that expected on the basis of the base composition. This might indicate that the possibility of high expression is restored, and that the gene in fact has to be highly expressed at some point during viral pathogenesis.

The results presented herein clearly indicate that codon preference has a severe effect on protein levels, and suggest that translational elongation is controlling mammalian gene expression. However, other factors may play a role. First, abundance of not maximally loaded mRNA's in eukaryotic cells indicates that initiation is rate limiting for translation in at least some cases, since otherwise all transcripts would be completely covered by ribosomes. Furthermore, if ribosome stalling and subsequent mRNA degradation were the mechanism, suppression by rare codons could most likely not be reversed by any regulatory mechanism like the one presented herein. One possible explanation for the influence of both initiation and elongation on translational activity is that the rate of initiation, or access to ribosomes, is controlled in part by cues distributed throughout the RNA, such that the lentiviral codons predispose the RNA to accumulate in a pool of poorly initiated RNAs. However, this limitation need not be kinetic; for example, the choice of codons could influence the probability that a given translation product, once initiated, is properly completed. Under this mechanism, abundance of less favored codons would incur a significant cumulative probability of failure to complete the nascent polypeptide chain. The sequestered RNA would then be lent an improved rate of initiation by the action of rev. Since adenine residues are abundant in rev-responsive transcripts, it could be that RNA adenine methylation mediates this translational suppression.

Detailed Procedures

The following procedures were used in the above-described experiments.

Sequence Analysis

Sequence analyses employed the software developed by the University of Wisconsin Computer Group.

Plasmid Constructions

Plasmid constructions employed the following methods. Vectors and insert DNA was digested at a concentration of 0.5 μg/10 μl in the appropriate restriction buffer for 1–4 hours (total reaction volume approximately 30 μl). Digested vector was treated with 10% (v/v) of 1 μg/ml calf intestine alkaline phosphatase for 30 min prior to gel electrophoresis. Both vector and insert digests (5 to 10 μl each) were run on a 1.5% low melting agarose gel with TAE buffer. Gel slices containing bands of interest were transferred into a 1.5 ml reaction tube, melted at 65° C. and directly added to the ligation without removal of the agarose. Ligations were typically done in a total volume of 25 μl in 1×Low Buffer 1×Ligation Additions with 200–400 U of ligase, 1 μl of vector, and 4 μl of insert. When necessary, 5' overhanging ends were filled by adding 1/10 volume of 250 μM dNTPs and 2–5 U of Klenow polymerase to heat inactivated or phenol extracted digests and incubating for approximately 20 min at room temperature. When necessary, 3' overhanging ends were filled by adding 1/10 volume of 2.5 mM dNTPs and 5–10 U of T4 DNA polymerase to heat inactivated or phenol extracted digests, followed by incubation at 37° C. for 30 min. The following buffers were used in these reactions: 10×Low buffer (60 mM Tris HCl, pH 7.5, 60 mM $MgCl_2$, 50 mM NaCl, 4 mg/ml BSA, 70 mM β-mercaptoethanol, 0.02% $NaN_3$); 10×Medium buffer (60 mM Tris HCl, pH 7.5, 60 mM $MgCl_2$, 50 mM NaCl, 4 mg/ml BSA, 70 mM β-mercaptoethanol, 0.02% $NaN_3$); 10×High buffer (60 mM Tris HCl, pH 7.5, 60 mM $MgCl_2$, 50 mM NaCl, 4 mg/ml BSA, 70 mM β-mercaptoethanol, 0.02% $NaN_3$); 10×Ligation additions (1 mM ATP, 20 mM DTT, 1 mg/ml BSA, 10 mM spermidine); 50×TAE (2 M Tris acetate, 50 mM EDTA).

Oligonucleotide Synthesis and Purification

Oligonucleotides were produced on a Milligen 8750 synthesizer (Millipore). The columns were eluted with 1 ml of 30% ammonium hydroxide, and the eluted oligonucleotides were deblocked at 55° C. for 6 to 12 hours. After deblockiong, 150 μl of oligonucleotide were precipitated with 10×volume of unsaturated n-butanol in 1.5 ml reaction tubes, followed by centrifugation at 15,000 rpm in a microfuge. The pellet was washed with 70% ethanol and resuspended in 50 μl of $H_2O$. The concentration was determined by measuring the optical density at 260 nm in a dilution of 1:333 (1 $OD_{260}$=30 μg/ml).

The following oligonucleotides were used for construction of the synthetic gp120 gene (all sequences shown in this text are in 5' to 3' direction). oligo 1 forward (Nhe1): cgc ggg cta gcc acc gag aag ctg (SEQ ID NO:1).

oligo 1: acc gag aag ctg tgg gtg acc gtg tac tac ggc gtg ccc gtg tgg aag ag ag gcc acc acc acc ctg ttc tgc gcc agc gac gcc aag gcg tac gac acc gag gtg cac aac gtg tgg gcc acc cag gcg tgc gtg ccc acc gac ccc aac ccc cag gag gtg gag ctc gtg aac gtg acc gag aac ttc aac at (SEQ ID NO:2).

oligo 1 reverse: cca cca tgt tgt tct tcc aca tgt tga agt tct c (SEQ ID NO:3).

oligo 2 forward: gac cga gaa ctt caa cat gtg gaa gaa caa cat (SEQ ID NO:4)

oligo 2: tgg aag aac aac atg gtg gag cag atg cat gag gac atc atc agc ctg tgg gac cag agc ctg aag ccc tgc gtg aag ctg acc cc ctg tgc gtg acc tg aac tgc acc gac ctg agg aac acc acc aac acc aac ac agc acc gcc aac aac aac agc aac agc gag ggc acc atc aag ggc ggc gag atg (SEQ ID NO:5).

oligo 2 reverse (Pst1): gtt gaa gct gca gtt ctt cat ctc gcc gcc ctt (SEQ ID NO:6).

oligo 3 forward (Pst1): gaa gaa ctg cag ctt caa cat cac cac cag c (SEQ ID NO:7).

oligo 3: aac atc acc acc agc atc cgc gac aag atg cag aag gag tac gcc ctg ctg tac aag ctg gat atc gtg agc atc gac aac gac agc acc agc tac cgc ctg atc tcc tgc aac acc agc gtg atc acc cag gcc tgc ccc aag atc agc ttc gag ccc atc ccc atc cac tac tgc gcc ccc gcc ggc ttc gcc (SEQ ID NO:8).

oligo 3 reverse: gaa ctt ctt gtc ggc ggc gaa gcc ggc ggg (SEQ ID NO:9).

oligo 4 forward: gcg ccc ccg ccg gct tcg cca tcc tga agt gca acg aca aga agt tc (SEQ ID NO:10)

oligo 4: gcc gac aag aag ttc agc ggc aag ggc agc tgc aag aac gtg agc acc gtg cag tgc acc cac ggc atc cgg ccg gtg gtg agc acc cag ctc ctg ctg aac ggc agc ctg gcc gag gag gag gtg gtg atc cgc agc gag aac ttc acc gac aac gcc aag acc atc atc gtg cac ctg aat gag agc gtg cag atc (SEQ ID NO:11)

oligo 4 reverse (Mlu1): agt tgg gac gcg tgc agt tga tct gca cgc tct c (SEQ ID NO:12).

oligo 5 forward (Mlu1): gag agc gtg cag atc aac tgc acg cgt ccc (SEQ ID NO:13).

oligo 5: aac tgc acg cgt ccc aac tac aac aag cgc aag cgc atc cac atc ggc ccc ggg cgc gcc ttc tac acc acc aag aac atc atc ggc acc atc ctc cag gcc cac tgc aac atc tct aga (SEQ ID NO:14).

oligo 5 reverse: gtc gtt cca ctt ggc tct aga gat gtt gca (SEQ ID NO:15).

oligo 6 forward: gca aca tct cta gag cca agt gga acg ac (SEQ ID NO:16).

oligo 6: gcc aag tgg aac gac acc ctg cgc cag atc gtg agc aag ctg aag gag cag ttc aag aac aag acc atc gtg ttc ac cag agc agc ggc ggc gac ccc gag atc gtg atg cac agc ttc aac tgc ggc ggc (SEQ ID NO:17).

oligo 6 reverse (EcoR1): gca gta gaa gaa ttc gcc gcc gca gtt ga (SEQ ID NO:18).

oligo 7 forward (EcoR1): tca act gcg gcg gcg aat tct tct act gc (SEQ ID NO:19).

oligo 7: ggc gaa ttc ttc tac tgc aac acc agc ccc ctg ttc aac agc acc tgg aac ggc aac aac acc tgg aac aac acc acc ggc agc aac aac aat att acc ctc cag tgc aag atc aag cag atc atc aac atg tgg cag gag gtg ggc aag gcc atg tac gcc ccc ccc atc gag ggc cag atc cgg tgc agc agc (SEQ ID NO:20).

oligo 7 reverse: gca gac cgg tga tgt tgc tgc tgc acc gga tct ggc cct c (SEQ ID NO:21).

oligo 8 forward: cga ggg cca gat ccg gtg cag cag caa cat cac cgg tct g (SEQ ID NO:22).

oligo 8: aac atc acc ggt ctg ctg ctg acc cgc gac ggc ggc aag gac acc gac acc aac gac acc gaa atc ttc cgc ccc ggc ggc ggc gac atg cgc gac aac tgg aga tct gag ctg tac aag tac aag gtg gtg acg atc gag ccc ctg ggc gtg gcc ccc acc aag gcc aag cgc cgc gtg gtg cag cgc gag aag cgc (SEQ ID NO:23).

oligo 8 reverse (Not1): cgc ggg cgg ccg ctt tag cgc ttc tcg cgc tgc acc ac (SEQ ID NO:24).

The following oligonucleotides were used for the construction of the ratTHY-1env gene.

oligo 1 forward (BamH1/Hind3): cgc ggg gga tcc aag ctt acc atg att cca gta ata agt (SEQ ID NO:25).

oligo 1: atg aat cca gta ata agt ata aca tta tta tta agt gta tta caa atg agt aga gga caa aga gta ata agt tta aca gca tct tta gta aat caa aat ttg aga tta gat tgt aga cat gaa aat aat aca aat ttg cca ata caa cat gaa ttt tca tta acg (SEQ ID NO:26).

oligo 1 reverse (EcoR1/Mlu1): cgc ggg gaa ttc acg cgt taa tga aaa ttc atg ttg (SEQ ID NO:27).

oligo 2 forward (BamH1/Mlu1): cgc gga tcc acg cgt gaa aaa aaa aaa cat (SEQ ID NO:28).

oligo 2: cgt gaa aaa aaa aaa cat gta tta agt gga aca tta gga gta cca gaa cat aca tat aga agt aga gta aat ttg ttt agt gat aga ttc ata aaa gta tta aca tta gca aat ttt aca aca aaa gat gaa gga gat tat atg tgt gag (SEQ ID NO:29).

oligo 2 reverse (EcoR1/Sac1): cgc gaa ttc gag ctc aca cat ata atc tcc (SEQ ID NO:30).

oligo 3 forward (BamH1/Sac1): cgc gga tcc gag ctc aga gta agt gga caa (SEQ ID NO:31).

oligo 3: ctc aga gta agt gga caa aat cca aca gta agt aat aaa aca ata aat gta ata aga gat aaa tta gta aaa tgt ga gga ata agt tta tta gta caa aat aca agt tgg tta tta tta tta tta agt tta agt ttt tta caa gca aca gat ttt ata agt tta tga (SEQ ID NO:32).

oligo 3 reverse (EcoR1/Not1 ): cgc gaa ttc gcg gcc gct tca taa act tat aaa atc (SEQ ID NO:33).

Polymerase Chain Reaction

Short, overlapping 15 to 25 mer oligonucleotides annealing at both ends were used to amplify the long oligonuclotides by polymerase chain reaction (PCR). Typical PCR conditions were: 35 cycles, 55° C. annealing temperature, 0.2 sec extension time. PCR products were gel purified, phenol extracted, and used in a subsequent PCR to generate longer fragments consisting of two adjacent small fragments. These longer fragments were cloned into a CDM7-derived plasmid containing a leader sequence of the CD5 surface molecule followed by a Nhe1/Pst1/Mlu1/EcoR1/BamH1 polylinker.

The following solutions were used in these reactions: 10×PCR buffer (500 mM KCl, 100 mM Tris HCl, pH 7.5, 8 mM MgCl$_2$, 2 mM each dNTP). The final buffer was complemented with 10% DMSO to increase fidelity of the Taq polymerase.

Small scale DNA Preparation

Transformed bacteria were grown in 3 ml LB cultures for more than 6 hours or overnight. Approximately 1.5 ml of each culture was poured into 1.5 ml microfuge tubes, spun for 20 seconds to pellet cells and resuspended in 200 µl of solution I. Subsequently 400 µl of solution II and 300 µl of solution III were added. The microfuge tubes were capped, mixed and spun for >30 sec. Supernatants were transferred into fresh tubes and phenol extracted once. DNA was precipitated by filling the tubes with isopropanol, mixing, and spinning in a microfuge for >2 min. The pellets were rinsed in 70% ethanol and resuspended in 50 µl dH20 containing 10 µl of RNAse A. The following media and solutions were used in these procedures: LB medium (1.0% NaCl, 0.5% yeast extract, 1.0% trypton); solution I (10 mM EDTA pH 8.0); solution II (0.2 M NaOH, 1.0% SDS); solution III (2.5 M KOAc, 2.5 M glacial aceatic acid); phenol (pH adjusted to 6.0, overlaid with TE); TE (10 mM Tris HCl, pH 7.5, 1 mM EDTA pH 8.0).

Large Scale DNA Preparation

One liter cultures of transformed bacteria were grown 24 to 36 hours (MC1061p3 transformed with pCDM derivatives) or 12 to 16 hours (MC1061 transformed with pUC derivatives) at 37° C. in either M9 bacterial medium (pCDM derivatives) or LB (pUC derivatives). Bacteria were spun down in 1 liter bottles using a Beckman J6 centrifuge at 4,200 rpm for 20 min. The pellet was resuspended in 40 ml of solution I. Subsequently, 80 ml of solution II and 40 ml of solution III were added and the bottles were shaken semivigorously until lumps of 2 to 3 mm size developed. The bottle was spun at 4,200 rpm for 5 min and the supernatant was poured through cheesecloth into a 250 ml bottle.

Isopropanol was added to the top and the bottle was spun at 4,200 rpm for 10 min. The pellet was resuspended in 4.1 ml of solution I and added to 4.5 g of cesium chloride, 0.3 ml of 10 mg/ml ethidium bromide, and 0.1 ml of 1% Triton X100 solution. The tubes were spun in a Beckman J2 high speed centrifuge at 10,000 rpm for 5 min. The supernatant was transferred into Beckman Quick Seal ultracentrifuge tubes, which were then sealed and spun in a Beckman ultracentrifuge using a NVT90 fixed angle rotor at 80,000 rpm for >2.5 hours. The band was extracted by visible light using a 1 ml syringe and 20 gauge needle. An equal volume of dH$_2$O was added to the extracted material. DNA was extracted once with n-butanol saturated with 1 M sodium chloride, followed by addition of an equal volume of 10 M ammonium acetate/1 mM EDTA. The material was poured into a 13 ml snap tube which was tehn filled to the top with absolute ethanol, mixed, and spun in a Beckman J2 centrifuge at 10,000 rpm for 10 min. The pellet was rinsed with 70% ethanol and resuspended in 0.5 to 1 ml of H$_2$O. The DNA concentration was determined by measuring the optical density at 260 nm in a dilution of 1:200 (1 OD$_{260}$=50 µg/ml).

The following media and buffers were used in these procedures: M9 bacterial medium (10 g M9 salts, 10 g casamino acids (hydrolyzed), 10 ml M9 additions, 7.5 µg/ml tetracycline (500 µl of a 15 mg/ml stock solution), 12.5 µg/ml ampicillin (125 µl of a 10 mg/ml stock solution); M9 additions (10 mM CaCl$_2$, 100 mM MgSO$_4$, 200, g/ml thiamine, 70% glycerol); LB medium (1.0% NaCl, 0.5% yeast extract, 1.0% trypton); Solution I (10 mM EDTA pH 8.0); Solution II (0.2 M NaOH 1.0% SDS); Solution III (2.5 M KOAc 2.5 M HOAc)

Sequencing

Synthetic genes were sequenced by the Sanger dideoxynucleotide method. In brief, 20 to 50 µg double-stranded plasmid DNA were denatured in 0.5 M NaOH for 5 min. Subsequently the DNA was precipitated with 1/10 volume of sodium acetate (pH 5.2) and 2 volumes of ethanol and centrifuged for 5 min. The pellet was washed with 70% ethanol and resuspended at a concentration of 1 µg/µl . The annealing reaction was carried out with 4 µg of template DNA and 40 ng of primer in 1×annealing buffer in a final volume of 10 μl. The reaction was heated to 65° C. and slowly cooled to 37° C.

In a separate tube 1 μl of 0.1 M DTT, 2 μl of labeling mix, 0.75 μl of dH$_2$O, 1 μl of [$^{35}$S] DATP (10 μCi), and 0.25 μl of Sequenase™ (12 U/μl) were added for each reaction. Five μl of this mix were added to each annealed primer-template tube and incubated for 5 min at room temperature. For each labeling reaction 2.5 μl of each of the 4 termination mixes were added on a Terasaki plate and prewarmed at 37° C. At the end of the incubation period 3.5 μl of labeling reaction were added to each of the 4 termination mixes. After 5 min, 4 μl of stop solution were added to each reaction and the Terasaki plate was incubated at 80° C. for 10 min in an oven. The sequencing reactions were run on 5% denaturing polyacrylamide gel. An acrylamide solution was prepared by adding 200 ml of 10×TBE buffer and 957 ml of dH$_2$O to 100 g of acrylamide:bisacrylamide (29:1). 5% polyacrylamide 46% urea and 1×TBE gel was prepared by combining 38 ml of acrylamide solution and 28 g urea. Polymerization was initiated by the addition of 400 μl of 10% ammonium peroxodisulfate and 60 μl of TEMED. Gels were poured using silanized glass plates and sharktooth combs and run in 1×TBE buffer at 60 to 100 W for 2 to 4 hours (depending on the region to be read). Gels were transferred to Whatman blotting paper, dried at 80° C. for about 1 hour, and exposed to x-ray film at room temperature. Typically exposure time was 12 hours. The following solutions were used in these procedures: 5×Annealing buffer (200 mM Tris HCl, pH 7.5, 100 mM MgCl$_2$, 250 mM NaCl); Labelling Mix (7.5 μM each dCTP, dGTP, and dTTP); Termination Mixes (80 μM each DNTP, 50 mM NaCl, 8 μM ddNTP (one each)); Stop solution (95% formamide, 20 mM EDTA, 0.05% bromphenol blue, 0.05% xylencyanol); 5×TBE (0.9 M Tris borate, 20 mM EDTA); Polyacrylamide solution (96.7 g polyacrylamide, 3.3 g bisacrylamide, 200 ml 1×TBE, 957 ml dH$_2$O).

RNA Isolation

Cytoplasmic RNA was isolated from calcium phosphate transfected 293T cells 36 hours post transfection and from vaccinia infected Hela cells 16 hours post infection essentially as described by Gilman. (Gilman Preparation of cytoplasmic RNA from tissue culture cells. In *Current Protocols in Molecular Biology*, Ausubel et al., eds., Wiley & Sons, New York, 1992). Briefly, cells were lysed in 400 μl lysis buffer, nuclei were spun out, and SDS and proteinase K were added to 0.2% and 0.2 mg/ml respectively. The cytoplasmic extracts were incubated at 37° C. for 20 min, phenol/chloroform extracted twice, and precipitated. The RNA was dissolved in 100 μl buffer I and incubated at 37° C. for 20 min. The reaction was stopped by adding 25 μl stop buffer and precipitated again.

The following solutions were used in this procedure: Lysis Buffer (TRUSTEE containing with 50 mM Tris pH 8.0, 100 mM NaCl, 5 mM MgCl$_2$, 0.5% NP40); Buffer I (TRUSTEE buffer with 10 mM MgCl$_2$, 1 mM DTT, 0.5 U/μl placental RNAse inhibitor, 0.1 U/μl RNAse free DNAse I); Stop buffer (50 mM EDTA 1.5 M NaOAc 1.0% SDS).

Slot Blot Analysis

For slot blot analysis 10 μg of cytoplasmic RNA was dissolved in 50 μl dH$_2$O to which 150 μl of 10×SSC/18% formaldehyde were added. The solubilized RNA was then incubated at 65° C. for 15 min and spotted onto with a slot blot apparatus. Radioactively labeled probes of 1.5 kb gp120IIIb and syngp120mn fragments were used for hybridization. Each of the two fragments was random labeled in a 50 μl reaction with 10 μl of 5×oligo-labeling buffer, 8 μl of 2.5 mg/ml BSA, 4 μl of [$^{32}$P]-dCTP (20 uCi/μl; 6000 Ci/mmol), and 5 U of Klenow fragment. After 1 to 3 hours incubation at 37° C. 100 μl of TRUSTEE were added and unincorporated [$^{32}$P]-dCTP was eliminated using G50 spin column. Activity was measured in a Beckman beta-counter, and equal specific activities were used for hybridization. Membranes were pre-hybridized for 2 hours and hybridized for 12 to 24 hours at 42° C. with 0.5×10$^6$ cpm probe per ml hybridization fluid. The membrane was washed twice (5 min) with washing buffer I at room temperature, for one hour in washing buffer II at 65° C., and then exposed to x-ray film. Similar results were obtained using a 1.1 kb Not1 /Sfi1 fragment of pCDM7 containing the 3 untranslated region. Control hybridizations were done in parallel with a random-labeled human beta-actin probe. RNA expression was quantitated by scanning the hybridized nitrocellulose membranes with a Magnetic Dynamics phosphorimager.

The following solutions were used in this procedure: 5×Oligo-labeling buffer (250 mM Tris HCl, pH 8.0, 25 mM MgCl$_2$, 5 mM β-mercaptoethanol, 2 mM DATP, 2 mM dGTP, mM dTTP, 1 M Hepes pH 6.6, 1 mg/ml hexanucleotides [dNTP]6); Hybridization Solution (0.05 M sodium phosphate, 250 mM NaCl, 7% SDS, 1 mM EDTA, 5% dextrane sulfate, 50% formamide, 100 μg/ml denatured salmon sperm DNA); Washing buffer I (2×SSC, 0.1% SDS); Washing buffer II (0.5×SSC, 0.1% SDS); 20×SSC (3 M NaCl, 0.3 M Na$_3$citrate, pH adjusted to 7.0).

Vaccinia Recombination

Vaccinia recombination used a modification of the of the method described by Romeo and Seed (Romeo and Seed, *Cell*, 64: 1037, 1991). Briefly, CV1 cells at 70 to 90% confluency were infected with 1 to 3 μl of a wild-type vaccinia stock WR (2×10$^8$ pfu/ml) for 1 hour in culture medium without calf serum. After 24 hours, the cells were transfected by calcium phosphate with 25 μg TKG plasmid DNA per dish. After an additional 24 to 48 hours the cells were scraped off the plate, spun down, and resuspended in a volume of 1 ml. After 3 freeze/thaw cycles trypsin was added to 0.05 mg/ml and lysates were incubated for 20 min. A dilution series of 10, 1 and 0.1 μl of this lysate was used to infect small dishes (6 cm) of CV1 cells, that had been pretreated with 12.5 μg/ml mycophenolic acid, 0.25 mg/ml xanthin and 1.36 mg/ml hypoxanthine for 6 hours.

Infected cells were cultured for 2 to 3 days, and subsequently stained with the monoclonal antibody NEA9301 against gp120 and an alkaline phosphatase conjugated secondary antibody. Cells were incubated with 0.33 mg/ml NBT and 0.16 mg/ml BCIP in AP-buffer and finally overlaid with 1% agarose in PBS. Positive plaques were picked and resuspended in 100 μl Tris pH 9.0. The plaque purification was repeated once. To produce high titer stocks the infection was slowly scaled up. Finally, one large plate of Hela cells was infected with half of the virus of the previous round. Infected cells were detached in 3 ml of PBS, lysed with a Dounce homogenizer and cleared from larger debris by centrifugation. VPE-8 recombinant vaccinia stocks were kindly provided by the AIDS repository, Rockville, Md., and express HIV-1 IIIB gp120 under the 7.5 mixed early/late promoter (Earl et al., *J. Virol.*, 65:31, 1991). In all experiments with recombinant vaccina cells were infected at a multiplicity of infection of at least 10.

The following solution was used in this procedure: AP buffer (100 mM Tris HCl, pH 9.5, 100 mM NaCl, 5 mM MgCl$_2$)

Cell Culture

The monkey kidney carcinoma cell lines CV1 and Cos7, the human kidney carcinoma cell line 293T, and the human cervix carcinoma cell line Hela were obtained from the American Tissue Typing Collection and were maintained in supplemented IMDM. They were kept on 10 cm tissue culture plates and typically split 1:5 to 1:20 every 3 to 4 days. The following medium was used in this procedure: Supplemented IMDM (90% Iscove's modified Dulbecco Medium, 10% calf serum, iron-complemented, heat inactivated 30 min 56° C., 0.3 mg/ml L-glutamine, 25 82 g/ml gentamycin 0.5 mM β-mercaptoethanol (pH adjusted with 5 M NaOH, 0.5 ml)).

Transfection

Calcium phosphate transfection of 293T cells was performed by slowly adding and under vortexing 10 μg plasmid DNA in 250 μl 0.25 M $CaCl_2$ to the same volume of 2×HEBS buffer while vortexing. After incubation for 10 to 30 min at room temperature the DNA precipitate was added to a small dish of 50 to 70% confluent cells. In cotransfection experiments with rev, cells were transfected with 10 μg gp120IIIb, gp120IIIbrre, syngp120mnrre or rTHY-1enveg1rre and 10 μg of pCMVrev or CDM7 plasmid DNA.

The following solutions were used in this procedure: 2×HEBS buffer (280 mM NaCl, 10 mM KCl, 1.5 mM sterile filtered); 0.25 mM $CaCl_2$ (autoclaved).

Immunoprecipitation

After 48 to 60 hours medium was exchanged and cells were incubated for additional 12 hours in Cys/Met-free medium containing 200 μCi of $^{35}$S-translabel. Supernatants were harvested and spun for 15 min at 3000 rpm to remove debris. After addition of protease inhibitors leupeptin, aprotinin and PMSF to 2.5 μg/ml, 50 μg/ml, 100 μg/ml respectively, 1 ml of supernatant was incubated with either 10 μl of packed protein A sepharose alone (rTHY-1enveg1rre) or with protein A sepharose and 3 μg of a purified CD4/immunoglobulin fusion protein (kindly provided by Behring) (all gp120 constructs) at 4° C. for 12 hours on a rotator. Subsequently the protein A beads were washed 5 times for 5 to 15 min each time. After the final wash 10 μl of loading buffer containing was added, samples were boiled for 3 min and applied on 7% (all gp120 constructs) or 10% (rTHY-1enveg1rre) SDS polyacrylamide gels (TRIS pH 8.8 buffer in the resolving, TRIS pH 6.8 buffer in the stacking gel, TRIS-glycin running buffer, Maniatis et al., supra 1989). Gels were fixed in 10% acetic acid and 10% methanol, incubated with Amplify for 20 min, dried and exposed for 12 hours.

The following buffers and solutions were used in this procedure: Wash buffer (100 mM Tris, pH 7.5, 150 mM NaCl, 5 mM $CaCl_2$, 1% NP-40); 5×Running Buffer (125 mM Tris, 1.25 M Glycin, 0.5% SDS); Loading buffer (10% glycerol, 4% SDS, 4% β-mercaptoethanol, 0.02% bromphenol blue).

Immunofluorescence 293T cells were transfected by calcium phosphate coprecipitation and analyzed for surface THY-1 expression after 3 days. After detachment with 1 mM EDTA/PBS, cells were stained with the monoclonal antibody OX-7 in a dilution of 1:250 at 4° C. for 20 min, washed with PBS and subsequently incubated with a 1:500 dilution of a FITC-conjugated goat anti-mouse immunoglobulin antiserum. Cells were washed again, resuspended in 0.5 ml of a fixing solution, and analyzed on a EPICS XL cytofluorometer (Coulter).

The following solutions were used in this procedure: PBS (137 mM NaCl, 2.7 mM KCl, 4.3 mM $Na_2HPO_4$, 1.4 mM $KH_2PO_4$, pH adjusted to 7.4); Fixing solution (2% formaldehyde in PBS).

ELISA

The concentration of gp120 in culture supernatants was determined using CD4-coated ELISA plates and goat anti-gp120 antisera in the soluble phase. Supernatants of 293T cells transfected by calcium phosphate were harvested after 4 days, spun at 3000 rpm for 10 min to remove debris and incubated for 12 hours at 4° C. on the plates. After 6 washes with PBS 100 μl of goat anti-gp120 antisera diluted 1:200 were added for 2 hours. The plates were washed again and incubated for 2 hours with a peroxidase-conjugated rabbit anti-goat IgG antiserum 1:1000. Subsequently the plates were washed and incubated for 30 min with 100 μl of substrate solution containing 2 mg/ml o-phenylenediamine in sodium citrate buffer. The reaction was finally stopped with 100 μl of 4 M sulfuric acid. Plates were read at 490 nm with a Coulter microplate reader. Purified recombinant gp120IIIb was used as a control. The following buffers and solutions were used in this procedure: Wash buffer (0.1% NP40 in PBS); Substrate solution (2 mg/ml o-phenylenediamine in sodium citrate buffer).

EXAMPLE 2

A Synthetic Green Fluorescent Protein Gene

The efficacy of codon replacement for gp120 suggests that replacing non-preferred codons with less preferred codons or preferred codons (and replacing less preferred codons with preferred codons) will increase expression in mammalian cells of other proteins, e.g., other eukaryotic proteins.

The green fluorescent protein (GFP) of the jellyfish Aequorea victoria (Ward, *Photochem. Photobiol.* 4:1, 1979; Prasher et al., *Gene* 111:229, 1992; Cody et al., *Biochem.* 32:1212, 1993) has attracted attention recently for its possible utility as a marker or reporter for transfection and lineage studies (Chalfie et al., *Science* 263:802, 1994).

Figure 10:
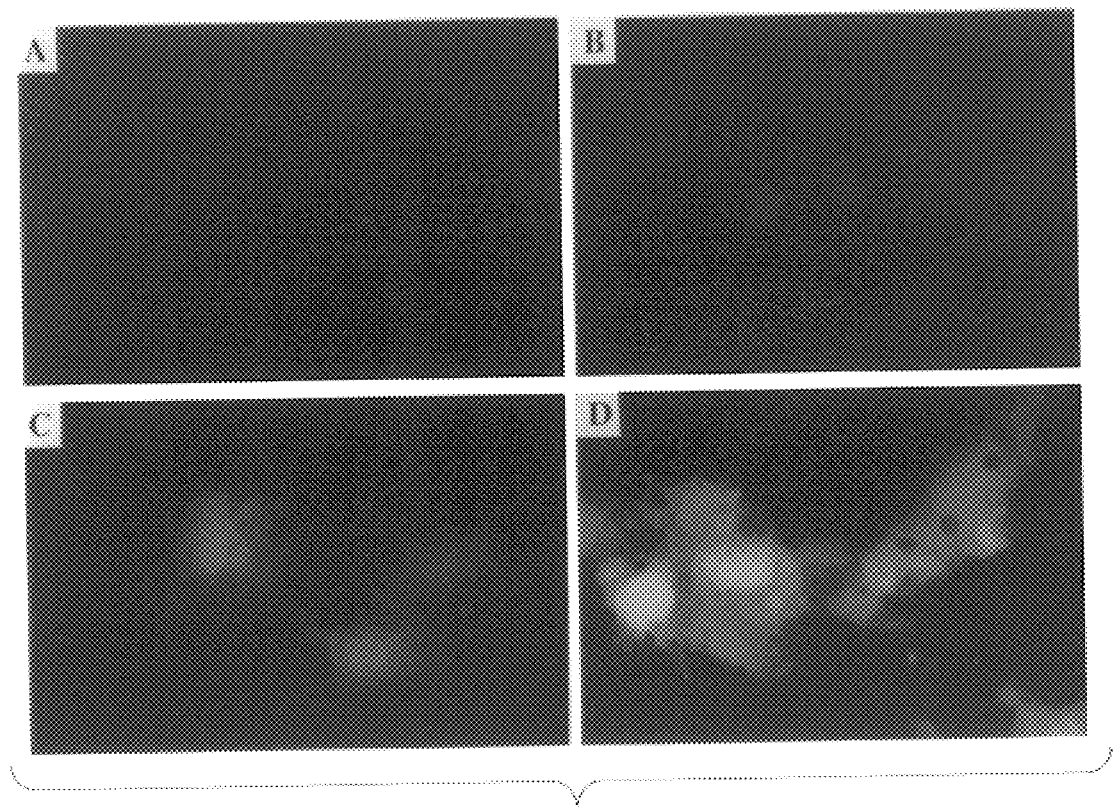
FIG. 10A is a photograph of COS cells transfected with vector only showing no GFP fluorescence.
FIG. 10B is a photograph of COS cells transfected with a CDM7 expression plasmid encoding native GFP engineered to include a consensus translational initiation sequence.
FIG. 10C is a photograph of COS cells transfected with an expression plasmid having the same flanking sequences and initiation consensus as in FIG. 10B, but bearing a codon optimized gene sequence.
FIG. 10D is a photograph of COS cells transfected with an expression plasmid as in FIG. 10C, but bearing a Thr at residue 65 in place of Ser.

Examination of a codon usage table constructed from the native coding sequence of GFP showed that the GFP codons favored either A or U in the third position. The bias in this case favors A less than does the bias of gp120, but is substantial. A synthetic gene was created in which the natural GFP sequence was re-engineered in much the same manner as for gp120 (FIG. 11; SEQ ID NO:40). In addition, the translation initiation sequence of GFP was replaced with sequences corresponding to the translational initiation consensus. The expression of the resulting protein was contrasted with that of the wild type sequence, similarly engineered to bear an optimized translational initiation consensus (FIG. 10B and FIG. 10C). In addition, the effect of inclusion of the mutation Ser 65→Thr, reported to improve excitation efficiency of GFP at 490 nm and hence preferred for fluorescence microscopy (Heim et al., *Nature* 373:663, 1995), was examined (FIG. 10D). Codon engineering conferred a significant increase in expression efficiency (an concomitant percentage of cells apparently positive for transfection), and the combination of the Ser 65→Thr mutation and codon optimization resulted in a DNA segment encoding a highly visible mammalian marker protein (FIG. 10D).

The above-described synthetic green fluorescent protein coding sequence was assembled in a similar manner as for gp120 from six fragments of approximately 120 bp each, using a strategy for assembly that relied on the ability of the restriction enzymes BsaI and BbsI to cleave outside of their recognition sequence. Long oligonucleotides were synthesized which contained portions of the coding sequence for GFP embedded in flanking sequences encoding EcoRI and BsaI at one end, and BamHI and BbsI at the other end. Thus, each oligonucleotide has the configuration EcoRI/BsaI/GFP fragment/BbsI/BamHI. The restriction site ends generated by the BsaI and BbsI sites were designed to yield compatible ends that could be used to join adjacent GFP fragments. Each of the compatible ends were designed to be unique and non-selfcomplementary. The crude synthetic DNA segments were amplified by PCR, inserted between EcoRI and BamHI in pUC9, and sequenced. Subsequently the intact coding sequence was assembled in a six fragment ligation, using insert fragments prepared with BsaI and BbsI. Two of six plasmids resulting from the ligation bore an insert of correct size, and one contained the desired full length sequence. Mutation of Ser65 to Thr was accomplished by standard PCR based mutagenesis, using a primer that overlapped a unique BssSI site in the synthetic GFP.

Codon Optimization as a Strategy for Improved Expression in Mammalian Cells

The data presented here suggest that coding sequence re-engineering may have general utility for the improvement of expression of mammalian and non-mammalian eukaryotic genes in mammalian cells. The results obtained here with three unrelated proteins: HIV gp120, the rat cell surface antigen Thy-1 and green fluorescent protein from Aequorea victoria, and human Factor VIII (see below) suggest that codon optimization may prove to be a fruitful strategy for improving the expression in mammalian cells of a wide variety of eukaryotic genes.

EXAMPLE III

Design of a Codon-Optimized Gene Expressing Human Factor VIII Lacking the Central B Domain A synthetic gene was designed that encodes mature human Factor VIII lacking amino acid residues 760 to 1639, inclusive (residues 779 to 1658, inclusive, of the precursor). The synthetic gene was created by choosing codons corresponding to those favored by highly expressed human genes. Some deviation from strict adherence to the favored residue pattern was made to allow unique restriction enzyme cleavage sites to be introduced throughout the gene to facilitate future manipulations. For preparation of the synthetic gene the sequence was then divided into 28 segments of 150 basepairs, and a 29th segment of 161 basepairs.

The a synthetic gene expressing human Factor VIII lacking the central B domain was constructed as follows. Twenty-nine pairs of template oligonucleotides (see below) were synthesized. The 5' template oligos were 105 bases long and the 3' oligos were 104 bases long (except for the last 3' oligo, which was 125 residues long). The template oligos were designed so that each annealing pair composed of one 5' oligo and one 3' oligo, created a 19 basepair double-stranded regions.

To facilitate the PCR and subsequent manipulations, the 5' ends of the oligo pairs were designed to be invariant over the first 18 residues, allowing a common pair of PCR primers to be used for amplification, and allowing the same PCR conditions to be used for all pairs. The first 18 residues of each 5' member of the template pair were cgc gaa ttc gga aga ccc (SEQ ID NO:110) and the first 18 residues of each 3' member of the template pair were: ggg gat cct cac gtc tca (SEQ ID NO:43).

Pairs of oligos were annealed and then extended and amplified by PCR in a reaction mixture as follows: templates were annealed at 200 µg/ml each in PCR buffer (10 mM Tris-HCl, 1.5 mM MgCl$_2$, 50 mM KCl, 100 µg/ml gelatin, pH 8.3). The PCR reactions contained 2 ng of the annealed template oligos, 0.5 µg of each of the two 18-mer primers (described below), 200 µM of each of the deoxynucleoside triphosphates, 10% by volume of DMSO and PCR buffer as supplied by Boehringer Mannheim Biochemicals, in a final volume of 50 µl. After the addition of Taq polymerase (2.5 units, 0.5 µl; Boehringer Mannheim Biochemicals) amplifications were conducted on a Perkin-Elmer Thermal Cycler for 25 cycles (94° C. for 30 sec, 55° C. for 30 sec, and 72° C. for 30 sec). The final cycle was followed by a 10 minute extension at 72° C.

The amplified fragments were digested with EcoRI and BamHI (cleaving at the 5' and 3' ends of the fragments respectively) and ligated to a pUC9 derivative cut with EcoRI and BamHI.

Individual clones were sequenced and a collection of plasmids corresponding to the entire desired sequence was identified. The clones were then assembled by multifragment ligation taking advantage of restriction sites at the 3' ends of the PCR primers, immediately adjacent to the amplified sequence. The 5' PCR primer contained a BbsI site, and the 3' PCR primer contained a BsmBI site, positioned so that cleavage by the respective enzymes preceded the first nucleotide of the amplified portion and left a 4 base 5' overhang created by the first 4 bases of the amplified portion. Simultaneous digestion with BbsI and BsmBI thus liberated the amplified portion with unique 4 base 5' overhangs at each end which contained none of the primer sequences. In general these overhangs were not self-complementary, allowing multifragment ligation reactions to produce the desired product with high efficiency. The unique portion of the first 28 amplified oligonucleotide pairs was thereby 154 basepairs, and after digestion each gave rise to a 150 bp fragment with unique ends. The first and last fragments were not manipulated in this manner, however, since they had other restriction sites designed into them to facilitate insertion of the assembled sequence into an appropriate mammalian expression vector. The actual assembly process proceded as follows.

Assembly of the Synthetic Factor VIII Gene

Step 1: 29 Fragments Assembled to Form 10 Fragments.

The 29 pairs of oligonucleotides, which formed segments 1 to 29 when base-paired, are described below.

Plasmids carrying segments 1, 5, 9, 12, 16, 20, 24 and 27 were digested with EcoR1 and BsmBI and the 170 bp fragments were isolated; plasmids bearing segments 2, 3, 6, 7, 10, 13, 17, 18, 21, 25, and 28 were digested with BbsI and BsmBI and the 170 bp fragments were isolated; and plasmids bearing segments 4, 8, 11, 14, 19, 22, 26 and 29 were digested with EcoRI and BbsI and the 2440 bp vector fragment was isolated. Fragments bearing segments 1, 2, 3 and 4 were then ligated to generate segment "A"; fragments bearing segments 5, 6, 7 and 8 were ligated to generate segment "B"; fragments bearing segments 9, 10 and 11 were ligated to generate segment "C"; fragments bearing segments 12, 13, and 14 were ligated to generate segment "D"; fragments bearing segments 16, 17, 18 and 19 were ligated to generate segment "F"; fragments bearing segments 20, 21 and 22 were ligated to generate segment "G"; fragments bearing segments 24, 25 and 26 were ligated to generate segment "I"; and fragments bearing segments 27, 28 and 29 were ligated to generate segment "J".

Step 2: Assembly of the 10 Resulting Fragments from Step 1 to Three Fragments.

Plasmids carrying the segments "A", "D" and "G" were digested with EcoRI and BsmBI, plasmids carrying the segments B, 15, 23, and I were digested with BbsI and BsmBI, and plasmids carrying the segments C, F, and J were digested with EcoRI and BbsI. Fragments bearing segments A, B, and C were ligated to generate segment "K"; fragments bearing segments D, 15, and F were ligated to generate segment "O"; and fragments bearing segments G, 23, I, and J were ligated to generate segment "P".

Step 3: Assembly of the Final Three Pieces.

The plasmid bearing segment K was digested with EcoRI and BsmBI, the plasmid bearing segment O was digested with BbsI and BsmBI, and the plasid bearing segment P was digested with EcoRI and BbsI. The three resulting fragments were ligated to generate segments.

Step 4: Insertion of the Synthetic Gene in a Mammalian Expression Vector.

The plasmid bearing segment S was digested with NheI and NotI and inserted between NheI and EagI sites of plasmid CD5lNEg1to generate plasmid cd5lsf8b-.

Sequencing and Correction of the Synthetic Factor VIII Gene

After assembly of the synthetic gene it was discovered that there were two undesired residues encoded in the sequence. One was an Arg residue at 749, which is present in the GenBank sequence entry originating from Genentech but is not in the sequence reported by Genentech in the literature. The other was an Ala residue at 146, which should have been Pro. This mutation arose at an unidentified step subsequent to the sequencing of the 29 constituent fragments. The Pro749Arg mutation was corrected by incorporating the desired change in a PCR primer (ctg ctt ctg acg cgt gct ggg gtg gcg gga gtt; SEQ ID NO:44) that included the MluI site at position 2335 of the sequence below (sequence of HindIII to NotI segment) and amplifying between that primer and a primer (ctg ctg aaa gtc tcc agc tgc; SEQ ID NO:44) 5' to the SgrAI site at 2225. The SgrAI to MluI fragment was then inserted into the expression vector at the cognate sites in the vector, and the resulting correct sequence change verified by sequencing. The Pro146Ala mutation was corrected by incorporating the desired sequence change in an oligonucleotide (ggc agg tgc tta agg aga acg gcc cta tgg cca; SEQ ID NO:46) bearing the AflII site at residue 504, and amplifying the fragment resulting from PCR reaction between that oligo and the primer having sequence cgt tgt tct tca tac gcg tct ggg gct cct cgg ggc (SEQ ID NO:109), cutting the resulting PCR fragment with AflII and AvrII at (residue 989), inserting the corrected fragment into the expression vector and confirming the construction by sequencing.

Construction of a Matched Native Gene Expressing Human Factor VIII Lacking the Central B Domain A matched Factor VIII B domain deletion expression plasmid having the native codon sequence was constructed by introducing NheI at the 5' end of the mature coding sequence using primer cgc caa ggg cta gcc gcc acc aga aga tac tac ctg ggt (SEQ ID NO:47), amplifying between that primer and the primer att cgt agt tgg ggt tcc tct gga cag (corresponding to residues 1067 to 1093 of the sequence shown below), cutting with NheI and AflII (residue 345 in the sequence shown below) and inserting the resulting fragment into an appropriately cleaved plasmid bearing native Factor VIII. The B domain deletion was created by overlap PCR using ctg tat ttg atg aga acc g, (corresponding to residues 1813 to 1831 below) and caa gac tgg tgg ggt ggc att aaa ttg ctt t (SEQ ID NO:48) (2342 to 2372 on complement below) for the 5' end of the overlap, and aat gcc acc cca cca gtc ttg aaa cgc ca (SEQ ID NO:49) (2352 to 2380 on sequence below) and cat ctg gat att gca ggg ag (SEQ ID NO:50) (3145 to 3164). The products of the two individual PCR reactions were then mixed and reamplified by use of the outermost primers, the resulting fragment cleaved by Asp718 (KpnI isoschizomer, 1837 on sequence below) and PflMI (3100 on sequence below), and inserted into the appropriately cleaved expression plasmid bearing native Factor VIII.

The complete sequence (SEQ ID NO:41) of the native human factor VIII gene deleted for the central B region is presented in FIG. 12. The complete sequence (SEQ ID NO:42) of the synthetic Factor VIII gene deleted for the central B region is presented in FIG. 13.

Preparation and Assay of Expression Plasmids

Two independent plasmid isolates of the native, and four independent isolates of the synthetic Factor VIII expression plasmid were separately propagated in bacteria and their DNA prepared by CsCl buoyant density centrifugation followed by phenol extraction. Analysis of the supernatants of COS cells transfected with the plasmids showed that the synthetic gene gave rise to approximately four times as much Factor VIII as did the native gene.

COS cells were then transfected with 5 μg of each factor VIII construct per 6 cm dish using the DEAE-dextran method. At 72 hours post-transfection, 4 ml of fresh medium containing 10% calf serum was added to each plated. A sample of media was taken from each plate 12 hr later. Samples were tested by ELISA using mouse anti-human factor VIII light chain monoclonal antibody and peroxidase-conjugated goat anti-human factor VIII polyclonal antibody. Purified human plasma factor VIII was used as a standard. Cells transfected with the synthetic Factor VIII gene construct expressed 138±20.2 ng/ml (equivalent ng/ml non-deleted Factor VIII) of Factor VIII (n=4) while the cells transfected with the native Factor VIII gene expressed 33.5±0.7 ng/ml (equivalent ng/ml non-deleted Factor VIII) of Factor VIII (n=2).

The following template oligonucleotides were used for construction of the synthetic Factor VIII gene.

```
                    r1 bbs   1 for (gcta)
cgc gaa ttc gga aga ccc gct agc cgc cac      1 r1
ccg ccg cta cta cct ggg cgc cgt gga gct
gtc ctg gga cta cat gca gag cga cct ggg
cga gct ccc cgt gga (SEQ ID NO:51)

ggg gat cct cac gtc tca ggt ttt ctt gta      1 bam
cac cac gct ggt gtt gaa ggg gaa gct ctt
ggg cac gcg ggg ggg gaa gcg ggc gtc cac
ggg gag ctc gcc ca  (SEQ ID NO:52)

r1 bbs   2 for (aacc)
cgc gaa ttc gga aga ccc aac cct gtt cgt      2 r1
gga gtt cac cga cca cct gtt caa cat tgc
caa gcc gcg ccc ccc ctg gat ggg cct gct
ggg ccc cac cat cca (SEQ ID NO:53)

ggg gat cct cac gtc tca gtg cag gct gac      2 bam
ggg gtg gct ggc cat gtt ctt cag ggt gat
cac cac ggt gtc gta cac ctc ggc ctg gat
ggt ggg gcc cag ca  (SEQ ID NO:54)

r1 bbs   3 for (gcac)
cgc gaa ttc gga aga ccc gca cgc cgt ggg      3 r1
cgt gag cta ctg gaa ggc cag cga ggg cgc
cga gta cga cga cca gac gtc cca gcg cga
gaa gga gga cga caa (SEQ ID NO:55)

ggg gat cct cac gtc tca gct ggc cat agg      3 bam
gcc gtt ctc ctt aag cac ctg cca cac gta
ggt gtg gct ccc ccc cgg gaa cac ctt gtc
gtc ctc ctt ctc gc  (SEQ ID NO:56)

r1 bbs   4 for (cagc)
cgc gaa ttc gga aga ccc cag cga ccc cct      4 r1
gtg cct gac cta cag cta cct gag cca cgt
gga cct ggt gaa gga tct gaa cag cgg gct
gat cgg cgc cct gct (SEQ ID NO:57)

ggg gat cct cac gtc tca gaa cag cag gat      4 bam
gaa ctt gtg cag ggt ctg ggt ttt ctc ctt
ggc cag gct gcc ctc gcg aca cac cag cag
ggc gcc gat cag cc  (SEQ ID NO:58)

r1 bbs   5 for (gttc)
cgc gaa ttc gga aga ccc gtt cgc cgt gtt      5 r1
cga cga ggg gaa gag ctg gca cag cga gac
taa gaa cag cct gat gca gga ccg cga cgc
cgc cag cgc ccg cgc (SEQ ID NO:59)

ggg gat cct cac gtc tca gtg gca gcc gat      5 bam
cag gcc ggg cag gct gcg gtt cac gta gcc
```

```
                          -continued
gtt aac ggt gtg cat ctt ggg cca ggc gcg
ggc gct ggc ggc gt  (SEQ ID NO:60)

r1 bbs  6 for (ccac)
cgc gaa ttc gga aga ccc cca ccg caa gag     6 r1
cgt gta ctg gca cgt cat cgg cat ggg cac
cac ccc tga ggt gca cag cat ctt cct gga
ggg cca cac ctt cct  (SEQ ID NO:61)

ggg gat cct cac gtc tca cag ggt ctg ggc     6 bam
agt cag gaa ggt gat ggg gct gat ctc cag
gct ggc ctg gcg gtg gtt gcg cac cag gaa
ggt gtg gcc ctc ca  (SEQ ID NO:62)

r1 bbs  7 for (cctg)
cgc gaa ttc gga aga ccc cct gct gat gga     7 r1
cct agg cca gtt cct gct gtt ctg cca cat
cag cag cca cca gca cga cgg cat gga ggc
tta cgt gaa ggt gga  (SEQ ID NO:63)

ggg gat cct cac gtc tca gtc gtc gtc gta     7 bam
gtc ctc ggc ctc ctc gtt gtt ctt cat gcg
cag ctg ggg ctc ctc ggg gca gct gtc cac
ctt cac gta agc ct  (SEQ ID NO:64)

r1 bbs  8 for (cgac)
cgc gaa ttc gga aga ccc cga cct gac cga     8 r1
cag cga gat gga tgt cgt acg ctt cga cga
cga cag ccc cag ctt cat cca gat ccg
cag cgt ggc caa gaa  (SEQ ID NO:65)

ggg gat cct cac gtc tca tac tag cgg ggc     8 bam
gta gtc cca gtc ctc ctc ggc ggc gat
gta gtg cac cca ggt ctt agg gtg ctt ctt
ggc cac gct gcg ga  (SEQ ID NO:66)

r1 bbs  9 for (agta)
cgc gaa ttc gga aga ccc agt act ggc ccc     9 r1
cga cga ccg cag cta caa gag cca gta cct
gaa caa cgg ccc cca gcg cat cgg ccg caa
gta caa gaa ggt gcg  (SEQ ID NO:67)

ggg gat cct cac gtc tca gag gat gcc gga     9 bam
ctc gtg ctg gat ggc ctc gcg ggt ctt gaa
agt ctc gtc ggt gta ggc cat gaa gcg cac
ctt ctt gta ctt gc  (SEQ ID NO:68)

r1 bbs 10 for (cctc)
cgc gaa ttc gga aga ccc cct cgg ccc cct    10 r1
gct gta cgg cga ggt ggg cga cac cct ggt
gat cat ctt caa gaa cca ggc cag cag gcc
cta caa cat cta ccc  (SEQ ID NO:69)

ggg gat cct cac gtc tca ctt cag gtg ctt    10 bam
cac gcc ctt ggg cag gcg gcg gct gta cag
ggg gcg cac gtc ggt gat gcc gtg ggg gta
gat gtt gta ggg cc  (SEQ ID NO:70)

r1 bbs 11 for (gaag)
cgc gaa ttc gga aga ccc gaa gga ctt ccc    11 r1
cat cct gcc cgg cga gat ctt caa gta caa
gtg gac cgt gac cgt gga gga cgg ccc cac
caa gag cga ccc ccg  (SEQ ID NO:71)

ggg gat cct cac gtc tca gcc gat cag tcc    11 bam
gga ggc cag gtc gcg ctc cat gtt cac gaa
gct gct gta gta gcg ggt cag gca gcg ggg
gtc gct ctt ggt gg  (SEQ ID NO:72)

r1 bbs 12 for (cggc)
cgc gaa ttc gga aga ccc cgg ccc cct gct    12 r1
gat ctg cta caa gga gag cgt gga cca gcg
cgg caa cca gat cat gag cga caa gca caa
cgt gat cct gtt cag  (SEQ ID NO:73)

ggg gat cct cac gtc tca agc ggg gtt ggg    12 bam
cag gaa gcg ctg gat gtt ctc ggt cag ata
cca gct gcg gtt ctc gtc gaa cac gct gaa
cag gat cac gtt gc  (SEQ ID NO:74)

-continued
                r1 bbs 13 for (cgct)
cgc gaa ttc gga aga ccc cgc tgg cgt gca    13 r1
gct gga aga tcc cga gtt cca ggc cag caa
cat cat gca cag cat caa cgg cta cgt gtt
cga cag cct gca gct  (SEQ ID NO:75)

ggg gat cct cac gtc tca cag gaa gtc ggt    13 bam
ctg ggc ccg gat gct cag gat gta cca gta
ggc cac ctc atg cag gca cac gct cag ctg
cag gct gtc gaa ca  (SEQ ID NO:76)

r1 bbs 14 for (cctg)
cgc gaa ttc gga aga ccc cct gag cgt gtt    14 r1
ctt ctc cgg gta tac ctt caa gca caa gat
ggt gta cga gga cac cct gac cct gtt ccc
ctt ctc cgg cga gac  (SEQ ID NO:77)

ggg gat cct cac gtc tca gtt gcg gaa gtc    14 bam
gct gtt gtg gca gcc cag aat cca cag gcc
ggg gtt ctc cat aga cat gaa cac agt ctc
gcc gga gaa ggg ga  (SEQ ID NO:78)

r1 bbs 15 for (caac)
cgc gaa ttc gga aga ccc caa ccg cgg cat    15 r1
gac tgc cct gct gaa agt cac ctg cga
caa cac cgg cga cta cta cga gga cag
cta cga gga cat ctc  (SEQ ID NO:79)

ggg gat cct cac gtc tca gcg gtg gcg gga    15 bam
gtt ttg gga gaa gga gcg ggg ctc gat ggc
gtt gtt ctt gga cag cag gta ggc gga gat
gtc ctc gta gct gt  (SEQ ID NO:80)

r1 bbs 16 fgr (ccgc)
cgc gaa ttc gga aga ccc ccg cag cac gcg    16 r1
tca gaa gca gtt caa cgc cac ccc ccc cgt
gct gaa gcg cca cca gcg cga gat cac ccg
cac cac cct gca aag  (SEQ ID NO:81)

ggg gat cct cac gtc tca gat gtc gaa gtc    16 bam
ctc ctt cat ctc cac gct gat ggt gtc
gtc gta gtc gat ctc ctc ctg gtc gct ttg
cag ggt ggt gcg gg  (SEQ ID NO:82)

r1 bbs 17 for (catc)
cgc gaa ttc gga aga ccc cat cta cga cga    17 r1
gga cga gaa cca gag ccc ccg ctc ctt cca
aaa gaa aac ccg cca cta ctt cat cgc cgc
cgt gga gcg cct gtg  (SEQ ID NO:83)

ggg gat cct cac gtc tca ctg ggg cac gct    17 bam
gcc gct ctg ggc gcg gtt gcg cag gac gtg
ggg gct gct gct cat gcc gta gtc cca cag
gcg ctc cac ggc gg  (SEQ ID NO:84)

r1 bbs 18 for (ccag)
cgc gaa ttc gga aga ccc cca gtt caa gaa    18 r1
ggt ggt tcc aga gtt cac cga cgg cag
ctt cac cca gcc cct gta ccg cgg cga gct
gaa cga gca cct ggg  (SEQ ID NO:85)

ggg gat cct cac gtc tca ggc ttg gtt gcg    18 bam
gaa ggt cac cat gat gtt gtc ctc cac ctc
ggc gcg gat gta ggg gcc gag cag gcc cag
gtg ctc gtt cag ct  (SEQ ID NO:86)

r1 bbs 19 for (agcc)
cgc gaa ttc gga aga ccc agc ctc ccg gcc    19 r1
cta ctc ctt cta tcc ctc cct gat cag cta
cga gga gga cca gcg cca ggg cgc cga gcc
ccg caa gaa ctt cgt  (SEQ ID NO:87)

ggg gat cct cac gtc tca ctc gtc ctt ggt    19 bam
ggg ggc cat gtg gtg ctg cac ctt cca gaa
gta ggt ctt agt ctc gtt ggg ctt cac gaa
gtt ctt gcg ggg ct  (SEQ ID NO:88)

r1 bbs 20 for (cgag)
cgc gaa ttc gga aga ccc cga gtt cga ctg    20 r1
caa ggc ctg ggc cta ctt cag cga cgt gga
```

```
cct gga gaa gga cgt gca cag cgg cct gat
cgg ccc cct gct ggt (SEQ ID NO:89)

ggg gat cct cac gtc tca gaa cag ggc aaa         20 bam
ttc ctg cac agt cac ctg cct ccc gtg ggg
ggg gtt cag ggt gtt ggt gtg gca cac cag
cag ggg gcc gat ca (SEQ ID NO:90)

r1 bbs 21 for (gttc)
cgc gaa ttc gga aga ccc gtt ctt cac cat         21 r1
ctt cga cga gac taa gag ctg gta ctt cac
cga gaa cat gga gcc caa ctg ccg cgc ccc
ctg caa cat cca gat (SEQ ID NO:91)

ggg gat cct cac gtc tca cag ggt gtc cat         21 bam
gat gta gcc gtt gat ggc gtg gca gcg gta
gtt ctc ctt gaa ggt ggg atc ttc cat ctg
gat gtt gca ggg gg (SEQ ID NO:92)

r1 bbs 22 for (cctg)
cgc gaa ttc gga aga ccc cct gcc cgg cct         22 r1
ggt gat ggc cca gga cca gcg cat ccg ctg
gta cct gct gtc tat ggg cag caa cga gaa
cat cca cag cat cca (SEQ ID NO:93)

ggg gat cct cac gtc tca gta cag gtt gta         22 bam
cag ggc cat ctt gta ctc ctc ctt ctt gcg
cac ggt gaa aac gtg gcc gct gaa gtg gat
gct gtg gat gtt ct (SEQ ID NO:94)

r1 bbs 23 for (gtac)
cgc gaa ttc gga aga ccc gta ccc cgg cgt         23 r1
gtt cga gac tgt gga gat gct gcc cag caa
ggc cgg gat ctg gcg cgt gga gtg cct gat
cgg cga gca cct gca (SEQ ID NO:95)

ggg gat cct cac gtc tca gct ggc cat gcc         23 bam
cag ggg ggt ctg gca ctt gtt gct gta cac
cag gaa cag ggt gct cat gcc ggc gtg cag
gtg ctc gcc gat ca (SEQ ID NO:96)

r1 bbs 24 for (cagc)
cgc gaa ttc gga aga ccc cag cgg cca cat         24 r1
ccg cga ctt cca gat cac cgc cag cgg cca
gta cgg cca gtg ggc tcc caa gct ggc cg
cct gca cta cag cgg (SEQ ID NO:97)

ggg gat cct cac gtc tca cat ggg ggc cag         24 bam
cag gtc cac ctt gat cca gga gaa ggg ctc
ctt ggt cga cca ggc gtt gat gct gcc gct
gta gtg cag gcg gg (SEQ ID NO:98)

r1 bbs 25 for (catg)
cgc gaa ttc gga aga ccc cat gat cat cca         25 r1
cgg cat caa gac cca ggg cgc ccg cca gaa
gtt cag cag cct gta cat cag cca gtt cat
cat cat gta ctc tct (SEQ ID NO:99)

ggg gat cct cac gtc tca gtt gcc gaa gaa         25 bam
cac cat cag ggt gcc ggt gct gtt gcc gcg
gta ggt ctg cca ctt ctt gcc gtc tag aga
gta cat gat gat ga (SEQ ID NO:100)

r1 bbs 26 for (caac)
cgc gaa ttc gga aga ccc caa cgt gga cag         26 r1
cag cgg cat caa gca caa cat ctt caa ccc
ccc cat ccc ccg cta cat ccg cct gca
ccc cac cca cta cag (SEQ ID NO:101)

ggg gat cct cac gtc tca gcc cag ggg cat         26 bam
gct gca gct gtt cag gtc gca gcc cag
ctc cat gcg cag ggt gct gcg gat gct gta
gtg ggt ggg gtg ca (SEQ ID NO:102)

r1 bbs 27 for (gggc)
cgc gaa ttc gga aga ccc ggg cat gga gag         27 r1
caa ggc cat cag cga cgc cca gat cac cgc
ctc cag cta ctt cac caa cat gtt cgc cac
ctg gag ccc cag caa (SEQ ID NO:103)

ggg gat cct cac gtc tca cca ctc ctt ggg         27 bam
gtt gtt cac ctg ggg gcg cca ggc gtt gct
gcg gcc ctg cag gtg cag gcg ggc ctt gct
ggg gct cca ggt gg (SEQ ID NO:104)

r1 bbs 28 for (gtgg)
cgc gaa ttc gga aga ccc gtg gct gca ggt         28 r1
gga ctt cca gaa aac cat gaa ggt gac tgg
cgt gac cac cga ggg cgt caa gag cct gct
gac cag cat gta cgt (SEQ ID NO:105)

ggg gat cct cac gtc tca ctt gcc gtt ttg         28 bam
gaa gaa cag ggt cca ctg gtg gcc gtc ctg
gct gct gct gat cag gaa ctc ctt cac gta
cat gct ggt cag ca (SEQ ID NO:106)

r1 bbs 29 for (caag)
cgc gaa ttc gga aga ccc caa ggt gaa ggt         29 r1
gtt cca ggg caa cca gga cag ctt cac acc
ggt cgt gaa cag cct gga ccc ccc cct gct
gac ccg cta cct gcg (SEQ ID NO:107)

ggg gat cct cac gtc tca gcg gcc gct tca         29 bam
gta cag gtc ctg gct ctc gca gcc cag cac
ctc cat gcg cag ggc gat ctg gtg cac cca
gct ctg ggg gtg gat gcg cag gta gcg ggt
cag ca (SEQ ID NO:108)
```

The codon usage for the native and synthetic genes described above are presented in Tables 3 and 4, respectively.

TABLE 3

Codon Frequency of the Synthetic Factor VIII B Domain Deleted Gene

| AA  | Codon | Number | /1000 | Fraction |
|-----|-------|--------|-------|----------|
| Gly | GGG   | 7.00   | 4.82  | 0.09     |
| Gly | GGA   | 1.00   | 0.69  | 0.01     |
| Gly | GGT   | 0.00   | 0.00  | 0.00     |
| Gly | GGC   | 74.00  | 50.93 | 0.90     |
| Glu | GAG   | 81.00  | 55.75 | 6.96     |
| Glu | GAA   | 3.00   | 2.06  | 0.04     |
| Asp | GAT   | 4.00   | 2.75  | 0.05     |
| Asp | GAC   | 78.00  | 53.68 | 0.95     |
| Val | GTG   | 77.00  | 52.99 | 0.88     |
| Val | GTA   | 2.00   | 1.38  | 0.02     |
| Val | GTT   | 2.00   | 1.38  | 0.02     |
| Val | GTC   | 7.00   | 4.82  | 0.08     |
| Ala | GCG   | 0.00   | 0.00  | 0.00     |
| Ala | GCA   | 0.00   | 0.00  | 0.00     |
| Ala | GCT   | 3.00   | 2.06  | 0.04     |
| Ala | GCC   | 67.00  | 46.11 | 0.96     |
| Arg | AGG   | 2.00   | 1.38  | 0.03     |
| Arg | AGA   | 0.00   | 0.00  | 0.00     |
| Ser | AGT   | 0.00   | 0.00  | 0.00     |
| Ser | AGC   | 97.00  | 66.76 | 0.81     |
| Lys | AAG   | 75.00  | 51.62 | 0.94     |
| Lys | AAA   | 5.00   | 3.44  | 0.06     |
| Asn | AAT   | 0.00   | 0.00  | 0.00     |
| Asn | AAC   | 63.00  | 43.36 | 1.00     |
| Met | ATG   | 43.00  | 29.59 | 1.00     |
| Ile | ATA   | 0.00   | 0.00  | 0.00     |
| Ile | ATT   | 2.00   | 1.38  | 0.03     |
| Ile | ATC   | 72.00  | 49.55 | 0.97     |
| Thr | ACG   | 2.00   | 1.38  | 0.02     |
| Thr | ACA   | 1.00   | 0.69  | 0.01     |
| Thr | ACT   | 10.00  | 6.88  | 0.12     |
| Thr | ACC   | 70.00  | 48.18 | 0.84     |

TABLE 3-continued

Codon Frequency of the Synthetic
Factor VIII B Domain Deleted Gene

| AA | Codon | Number | /1000 | Fraction |
|---|---|---|---|---|
| Trp | TGG | 28.00 | 19.27 | 1.00 |
| End | TGA | 1.00 | 0.69 | 1.00 |
| Cys | TGT | 1.00 | 0.69 | 0.05 |
| Cys | TGC | 18.00 | 12.39 | 0.95 |
| End | TAG | 0.00 | 0.00 | 0.00 |
| End | TAA | 0.00 | 0.00 | 0.00 |
| Tyr | TAT | 2.00 | 1.38 | 0.03 |
| Tyr | TAC | 66.00 | 45.42 | 0.97 |
| Leu | TTG | 0.00 | 0.00 | 0.00 |
| Leu | TTA | 0.00 | 0.00 | 0.00 |
| Phe | TTT | 1.00 | 0.69 | 0.01 |
| Phe | TTC | 76.00 | 52.31 | 0.99 |
| Ser | TCG | 1.00 | 0.69 | 0.01 |
| Ser | TCA | 0.00 | 0.00 | 0.00 |
| Ser | TCT | 3.00 | 2.06 | 0.03 |
| Ser | TCC | 19.00 | 13.08 | 0.16 |
| Arg | CGG | 1.00 | 0.69 | 0.01 |
| Arg | CGA | 0.00 | 0.00 | 0.00 |
| Arg | CGT | 1.00 | 0.69 | 0.01 |
| Arg | CGC | 69.00 | 47.49 | 0.95 |
| Gln | CAG | 62.00 | 42.67 | 0.93 |
| Gln | CAA | 5.00 | 3.44 | 0.07 |
| His | CAT | 1.00 | 0.69 | 0.02 |
| His | CAC | 50.00 | 34.41 | 0.98 |
| Leu | CTG | 118.00 | 81.21 | 0.94 |
| Leu | CTA | 3.00 | 2.06 | 0.02 |
| Leu | CTT | 1.00 | 0.69 | 0.01 |
| Leu | CTC | 3.00 | 2.06 | 0.02 |
| Pro | CCG | 4.00 | 2.75 | 0.05 |
| Pro | CCA | 0.00 | 0.00 | 0.00 |
| Pro | CCT | 3.00 | 2.06 | 0.04 |
| Pro | CCC | 68.00 | 46.80 | 0.91 |

TABLE 4

Codon Frequency Table of the Native
Factor VIII B Domain Deleted Gene

| AA | Codon | Number | /1000 | Fraction |
|---|---|---|---|---|
| Gly | GGG | 12.00 | 8.26 | 0.15 |
| Gly | GGA | 34.00 | 23.40 | 0.41 |
| Gly | GGT | 16.00 | 11.01 | 0.20 |
| Gly | GGC | 20.00 | 13.76 | 0.24 |
| Glu | GAG | 33.00 | 22.71 | 0.39 |
| Glu | GAA | 51.00 | 35.10 | 0.61 |
| Asp | GAT | 55.00 | 37.85 | 0.67 |
| Asp | GAC | 27.00 | 18.58 | 0.33 |
| Val | GTG | 29.00 | 19.96 | 0.33 |
| Val | GTA | 19.00 | 13.08 | 0.22 |
| Val | GTT | 17.00 | 11.70 | 0.19 |
| Val | GTC | 23.00 | 15.83 | 0.26 |
| Ala | GCG | 2.00 | 1.38 | 0.03 |
| Ala | GCA | 18.00 | 12.39 | 0.25 |
| Ala | GCT | 31.00 | 21.34 | 0.44 |
| Ala | GCC | 20.00 | 13.76 | 0.28 |
| Arg | AGG | 18.00 | 12.39 | 0.25 |
| Arg | AGA | 22.00 | 15.14 | 0.30 |
| Ser | AGT | 22.00 | 15.14 | 0.18 |
| Ser | AGC | 24.00 | 16.52 | 0.20 |

TABLE 4-continued

Codon Frequency Table of the Native
Factor VIII B Domain Deleted Gene

| AA | Codon | Number | /1000 | Fraction |
|---|---|---|---|---|
| Lys | AAG | 32.00 | 22.02 | 0.40 |
| Lys | AAA | 48.00 | 33.04 | 0.60 |
| Asn | AAT | 38.00 | 26.15 | 0.60 |
| Asn | AAC | 25.00 | 17.21 | 0.40 |
| Met | ATG | 43.00 | 29.59 | 1.00 |
| Ile | ATA | 13.00 | 8.95 | 0.18 |
| Ile | ATT | 36.00 | 24.78 | 0.49 |
| Ile | ATC | 25.00 | 17.21 | 0.34 |
| Thr | ACG | 1.00 | 0.69 | 0.01 |
| Thr | ACA | 23.00 | 15.83 | 0.28 |
| Thr | ACT | 36.00 | 24.78 | 0.43 |
| Thr | ACC | 23.00 | 15.83 | 0.28 |
| Trp | TGG | 28.00 | 19.27 | 1.00 |
| End | TGA | 1.00 | 0.69 | 1.00 |
| Cys | TGT | 7.00 | 4.82 | 0.37 |
| Cys | TGC | 12.00 | 8.26 | 0.63 |
| End | TAG | 0.00 | 0.00 | 0.00 |
| End | TAA | 0.00 | 0.00 | 0.00 |
| Tyr | TAT | 41.00 | 28.22 | 0.60 |
| Tyr | TAC | 27.00 | 18.58 | 0.40 |
| Leu | TTG | 20.00 | 13.76 | 0.16 |
| Leu | TTA | 10.00 | 6.88 | 0.08 |
| Phe | TTT | 45.00 | 30.97 | 0.58 |
| Phe | TTC | 32.00 | 22.02 | 0.42 |
| Ser | TCG | 2.00 | 1.38 | 0.02 |
| Ser | TCA | 27.00 | 18.58 | 0.22 |
| Ser | TCT | 27.00 | 18.58 | 0.22 |
| Ser | TCC | 18.00 | 12.39 | 0.15 |
| Arg | CGG | 6.00 | 4.13 | 0.08 |
| Arg | CGA | 10.00 | 6.88 | 0.14 |
| Arg | CGT | 7.00 | 4.82 | 0.10 |
| Arg | CGC | 10.00 | 6.88 | 0.14 |
| Gln | CAG | 42.00 | 28.91 | 0.63 |
| Gln | CAA | 25.00 | 17.21 | 0.37 |
| His | CAT | 28.00 | 19.27 | 0.55 |
| His | CAC | 23.00 | 15.83 | 0.45 |
| Leu | CTG | 36.00 | 24.78 | 0.29 |
| Leu | CTA | 15.00 | 10.32 | 0.12 |
| Leu | CTT | 24.00 | 16.52 | 0.19 |
| Leu | CTC | 20.00 | 13.76 | 0.16 |
| Pro | CCG | 1.00 | 0.69 | 0.01 |
| Pro | CCA | 32.00 | 22.02 | 0.43 |
| Pro | CCT | 26.00 | 17.89 | 0.35 |
| Pro | CCC | 15.00 | 10.32 | 0.20 |

Use

The synthetic genes of the invention are useful for expressing the a protein normally expressed in mammalian cells in cell culture (e.g. for commercial production of human proteins such as hGH, TPA, Factor VIII, and Factor IX). The synthetic genes of the invention are also useful for gene therapy. For example, a synthetic gene encoding a selected protein can be introduced in to a cell which can express the protein to create a cell which can be administered to a patient in need of the protein. Such cell-based gene therapy techniques are well known to those skilled in the art, see, e.g., Anderson, et al., U.S. Pat. No. 5,399,349; Mulligan and Wilson, U.S. Pat. No. 5,460,959.

SEQUENCE LISTING (1) GENERAL INFORMATION:

(iii) NUMBER OF SEQUENCES: 110

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: Other (xi) SEQUENCE DESCRIPTION: SEQ ID NO:1:

```
CGCGGGCTAG CCACCGAGAA GCTG                                          24
```

(2) INFORMATION FOR SEQ ID NO:2:

(i) SEQUENCE CHARACTERISTICS:
      (A) LENGTH: 195 base pairs
      (B) TYPE: nucleic acid
      (C) STRANDEDNESS: single
      (D) TOPOLOGY: linear (ii) MOLECULE TYPE: Other (xi) SEQUENCE DESCRIPTION: SEQ ID NO:2:

```
ACCGAGAAGC TGTGGGTGAC CGTGTACTAC GGCGTGCCCG TGTGGAAGAG AGGCCACCAC    60

CACCCTGTTC TGCGCCAGCG ACGCCAAGGC GTACGACACC GAGGTGCACA ACGTGTGGGC   120

CACCCAGGCG TGCGTGCCCA CCGACCCCAA CCCCCAGGAG GTGGAGCTCG TGAACGTGAC   180

CGAGAACTTC AACAT                                                   195
```

(2) INFORMATION FOR SEQ ID NO:3:

(i) SEQUENCE CHARACTERISTICS:
      (A) LENGTH: 34 base pairs
      (B) TYPE: nucleic acid
      (C) STRANDEDNESS: single
      (D) TOPOLOGY: linear (ii) MOLECULE TYPE: Other (xi) SEQUENCE DESCRIPTION: SEQ ID NO:3:

```
CCACCATGTT GTTCTTCCAC ATGTTGAAGT TCTC                                34
```

(2) INFORMATION FOR SEQ ID NO:4:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: Other (xi) SEQUENCE DESCRIPTION: SEQ ID NO:4:

```
GACCGAGAAC TTCAACATGT GGAAGAACAA CAT                                 33
```

(2) INFORMATION FOR SEQ ID NO:5:

(i) SEQUENCE CHARACTERISTICS:
      (A) LENGTH: 192 base pairs
      (B) TYPE: nucleic acid (C) STRANDEDNESS: single
            (D) TOPOLOGY: linear (ii) MOLECULE TYPE: Other (xi) SEQUENCE DESCRIPTION: SEQ ID NO:5:

TGGAAGAACA ACATGGTGGA GCAGATGCAT GAGGACATCA TCAGCCTGTG GGACCAGAGC      60

CTGAAGCCCT GCGTGAAGCT GACCCCCTGT GCGTGACCTG AACTGCACCG ACCTGAGGAA     120

CACCACCAAC ACCAACACAG CACCGCCAAC AACAACAGCA ACAGCGAGGG CACCATCAAG     180

GGCGGCGAGA TG                                                        192

(2) INFORMATION FOR SEQ ID NO:6:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:6:

GTTGAAGCTG CAGTTCTTCA TCTCGCCGCC CTT                                   33

(2) INFORMATION FOR SEQ ID NO:7:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:7:

GAAGAACTGC AGCTTCAACA TCACCACCAG C                                     31

(2) INFORMATION FOR SEQ ID NO:8:

(i) SEQUENCE CHARACTERISTICS:
            (A) LENGTH: 195 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:8:

AACATCACCA CCAGCATCCG CGACAAGATG CAGAAGGAGT ACGCCCTGCT GTACAAGCTG      60

GATATCGTGA GCATCGACAA CGACAGCACC AGCTACCGCC TGATCTCCTG CAACACCAGC     120

GTGATCACCC AGGCCTGCCC CAAGATCAGC TTCGAGCCCA TCCCCATCCA CTACTGCGCC     180

CCCGCCGGCT TCGCC                                                     195

(2) INFORMATION FOR SEQ ID NO:9:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:9:

```
GAACTTCTTG TCGGCGGCGA AGCCGGCGGG                                        30

(2) INFORMATION FOR SEQ ID NO:10:

(i) SEQUENCE CHARACTERISTICS:
         (A) LENGTH: 47 base pairs
         (B) TYPE: nucleic acid
         (C) STRANDEDNESS: single
         (D) TOPOLOGY: linear (ii) MOLECULE TYPE: Other (xi) SEQUENCE DESCRIPTION: SEQ ID NO:10:

GCGCCCCCGC CGGCTTCGCC ATCCTGAAGT GCAACGACAA GAAGTTC                     47

(2) INFORMATION FOR SEQ ID NO:11:

(i) SEQUENCE CHARACTERISTICS:
         (A) LENGTH: 198 base pairs
         (B) TYPE: nucleic acid
         (C) STRANDEDNESS: single
         (D) TOPOLOGY: linear (ii) MOLECULE TYPE: Other (xi) SEQUENCE DESCRIPTION: SEQ ID NO:11:

GCCGACAAGA AGTTCAGCGG CAAGGGCAGC TGCAAGAACG TGAGCACCGT GCAGTGCACC       60

CACGGCATCC GGCCGGTGGT GAGCACCCAG CTCCTGCTGA ACGGCAGCCT GGCCGAGGAG      120

GAGGTGGTGA TCCGCAGCGA GAACTTCACC GACAACGCCA AGACCATCAT CGTGCACCTG      180

AATGAGAGCG TGCAGATC                                                    198

(2) INFORMATION FOR SEQ ID NO:12:

(i) SEQUENCE CHARACTERISTICS:
         (A) LENGTH: 34 base pairs
         (B) TYPE: nucleic acid
         (C) STRANDEDNESS: single
         (D) TOPOLOGY: linear (ii) MOLECULE TYPE: Other (xi) SEQUENCE DESCRIPTION: SEQ ID NO:12:

AGTTGGGACG CGTGCAGTTG ATCTGCACGC TCTC                                   34

(2) INFORMATION FOR SEQ ID NO:13:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: Other (xi) SEQUENCE DESCRIPTION: SEQ ID NO:13:

GAGAGCGTGC AGATCAACTG CACGCGTCCC                                        30

(2) INFORMATION FOR SEQ ID NO:14:

(i) SEQUENCE CHARACTERISTICS:
         (A) LENGTH: 120 base pairs
         (B) TYPE: nucleic acid
         (C) STRANDEDNESS: single
         (D) TOPOLOGY: linear (ii) MOLECULE TYPE: Other
```

(xi) SEQUENCE DESCRIPTION: SEQ ID NO:14:

AACTGCACGC GTCCCAACTA CAACAAGCGC AAGCGCATCC ACATCGGCCC CGGGCGCGCC     60

TTCTACACCA CCAAGAACAT CATCGGCACC ATCCTCCAGG CCCACTGCAA CATCTCTAGA    120

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:15:

GTCGTTCCAC TTGGCTCTAG AGATGTTGCA                                      30

(2) INFORMATION FOR SEQ ID NO:16:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:16:

GCAACATCTC TAGAGCCAAG TGGAACGAC                                       29

(2) INFORMATION FOR SEQ ID NO:17:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:17:

GCCAAGTGGA ACGACACCCT GCGCCAGATC GTGAGCAAGC TGAAGGAGCA GTTCAAGAAC     60

AAGACCATCG TGTTCACCAG AGCAGCGGCG GCGACCCCGA GATCGTGATG CACAGCTTCA    120

ACTGCGGCGG C                                                         131

(2) INFORMATION FOR SEQ ID NO:18:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:18:

GCAGTAGAAG AATTCGCCGC CGCAGTTGA                                       29

(2) INFORMATION FOR SEQ ID NO:19:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:19:

TCAACTGCGG CGGCGAATTC TTCTACTGC                                          29

(2) INFORMATION FOR SEQ ID NO:20:

(i) SEQUENCE CHARACTERISTICS:
            (A) LENGTH: 195 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:20:

GGCGAATTCT TCTACTGCAA CACCAGCCCC CTGTTCAACA GCACCTGGAA CGGCAACAAC        60

ACCTGGAACA CACCACCGG CAGCAACAAC AATATTACCC TCCAGTGCAA GATCAAGCAG        120

ATCATCAACA TGTGGCAGGA GGTGGGCAAG GCCATGTACG CCCCCCCCAT CGAGGGCCAG        180

ATCCGGTGCA GCAGC                                                         195

(2) INFORMATION FOR SEQ ID NO:21:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:21:

GCAGACCGGT GATGTTGCTG CTGCACCGGA TCTGGCCCTC                              40

(2) INFORMATION FOR SEQ ID NO:22:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:22:

CGAGGGCCAG ATCCGGTGCA GCAGCAACAT CACCGGTCTG                              40

(2) INFORMATION FOR SEQ ID NO:23:

(i) SEQUENCE CHARACTERISTICS:
            (A) LENGTH: 198 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:23:

AACATCACCG GTCTGCTGCT GACCCGCGAC GGCGGCAAGG ACACCGACAC CAACGACACC        60

GAAATCTTCC GCCCCGGCGG CGGCGACATG CGCGACAACT GGAGATCTGA GCTGTACAAG        120

TACAAGGTGG TGACGATCGA GCCCCTGGGC GTGGCCCCCA CCAAGGCCAA GCGCCGCGTG        180

GTGCAGCGCG AGAAGCGC                                                      198

(2) INFORMATION FOR SEQ ID NO:24:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:24:

```
CGCGGGCGGC CGCTTTAGCG CTTCTCGCGC TGCACCAC                         38
```

(2) INFORMATION FOR SEQ ID NO:25:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:25:

```
CGCGGGGAT CCAAGCTTAC CATGATTCCA GTAATAAGT                         39
```

(2) INFORMATION FOR SEQ ID NO:26:

(i) SEQUENCE CHARACTERISTICS:
        (A) LENGTH: 165 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:26:

```
ATGAATCCAG TAATAAGTAT AACATTATTA TTAAGTGTAT TACAAATGAG TAGAGGACAA   60

AGAGTAATAA GTTTAACAGC ATCTTTAGTA AATCAAAATT TGAGATTAGA TTGTAGACAT  120

GAAAATAATA CAAATTTGCC AATACAACAT GAATTTTCAT TAACG                  165
```

(2) INFORMATION FOR SEQ ID NO:27:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:27:

```
CGCGGGGAAT TCACGCGTTA ATGAAAATTC ATGTTG                           36
```

(2) INFORMATION FOR SEQ ID NO:28:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:28:

```
CGCGGATCCA CGCGTGAAAA AAAAAAACAT                                  30
```

(2) INFORMATION FOR SEQ ID NO:29:

(i) SEQUENCE CHARACTERISTICS:
        (A) LENGTH: 150 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:29:

CGTGAAAAAA AAAAACATGT ATTAAGTGGA ACATTAGGAG TACCAGAACA TACATATAGA    60

AGTAGAGTAA ATTTGTTTAG TGATAGATTC ATAAAAGTAT TAACATTAGC AAATTTTACA   120

ACAAAAGATG AAGGAGATTA TATGTGTGAG                                    150

(2) INFORMATION FOR SEQ ID NO:30:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:30:

CGCGAATTCG AGCTCACACA TATAATCTCC                                     30

(2) INFORMATION FOR SEQ ID NO:31:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:31:

CGCGGATCCG AGCTCAGAGT AAGTGGACAA                                     30

(2) INFORMATION FOR SEQ ID NO:32:

(i) SEQUENCE CHARACTERISTICS:
        (A) LENGTH: 170 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:32:

CTCAGAGTAA GTGGACAAAA TCCAACAAGT AGTAATAAAA CAATAAATGT AATAAGAGAT    60

AAATTAGTAA AATGTGAGGA ATAAGTTTAT TAGTACAAAA TACAAGTTGG TTATTATTAT   120

TATTATTAAG TTTAAGTTTT TTACAAGCAA CAGATTTTAT AAGTTTATGA              170

(2) INFORMATION FOR SEQ ID NO:33:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:33:

CGCGAATTCG CGGCCGCTTC ATAAACTTAT AAAATC        36

(2) INFORMATION FOR SEQ ID NO:34:

(i) SEQUENCE CHARACTERISTICS:
        (A) LENGTH: 1632 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:34:

```
CTCGAGATCC ATTGTGCTCT AAAGGAGATA CCCGGCCAGA CACCCTCACC TGCGGTGCCC        60
AGCTGCCCAG GCTGAGGCAA GAGAAGGCCA GAAACCATGC CCATGGGGTC TCTGCAACCG       120
CTGGCCACCT TGTACCTGCT GGGGATGCTG GTCGCTTCCG TGCTAGCCAC CGAGAAGCTG       180
TGGGTGACCG TGTACTACGG CGTGCCCGTG TGGAAGGAGG CCACCACCAC CCTGTTCTGC       240
GCCAGCGACG CCAAGGCGTA CGACACCGAG GTGCACAACG TGTGGGCCAC CCAGGCGTGC       300
GTGCCCACCG ACCCCAACCC CCAGGAGGTG GAGCTCGTGA ACGTGACCGA GAACTTCAAC       360
ATGTGGAAGA ACAACATGGT GGAGCAGATG CATGAGGACA TCATCAGCCT GTGGGACCAG       420
AGCCTGAAGC CCTGCGTGAA GCTGACCCCC CTGTGCGTGA CCCTGAACTG CACCGACCTG       480
AGGAACACCA CCAACACCAA CAACAGCACC GCCAACAACA ACAGCAACAG CGAGGGCACC       540
ATCAAGGGCG GCGAGATGAA CAACTGCAGC TTCAACATCA CCACCAGCAT CCGCGACAAG       600
ATGCAGAAGG AGTACGCCCT GCTGTACAAG CTGGATATCG TGAGCATCGA CAACGACAGC       660
ACCAGCTACC GCCTGATCTC CTGCAACACC AGCGTGATCA CCCAGGCCTG GCCCAAGATC       720
AGCTTCGAGC CCATCCCCAT CCACTACTGC GCCCCCGCCG GCTTCGCCAT CCTGAAGTGC       780
AACGACAAGA AGTTCAGCGG CAAGGGCAGC TGCAAGAACG TGAGCACCGT GCAGTGCACC       840
CACGGCATCC GGCCGGTGGT GAGCACCCAG CTCCTGCTGA ACGGCAGCCT GGCCGAGGAG       900
GAGGTGGTGA TCCGCAGCGA GAACTTCACC GACAACGCCA AGACCATCAT CGTGCACCTG       960
AATGAGAGCG TGCAGATCAA CTGCACGCGT CCCAACTACA ACAAGCGCAA GCGCATCCAC      1020
ATCGGCCCCG GGCGCGCCTT CTACACCACC AAGAACATCA TCGGCACCAT CCGCCAGGCC      1080
CACTGCAACA TCTCTAGAGC CAAGTGGAAC GACACCCTGC GCCAGATCGT GAGCAAGCTG      1140
AAGGAGCAGT TCAAGAACAA GACCATCGTG TTCAACCAGA GCAGCGGCGG CGACCCCGAG      1200
ATCGTGATGC ACAGCTTCAA CTGCGGCGGC GAATTCTTCT ACTGCAACAC CAGCCCCCTG      1260
TTCAACAGCA CCTGGAACGG CAACAACACC TGGAACAACA CCACCGGCAG CAACAACAAT      1320
ATTACCCTCC AGTGCAAGAT CAAGCAGATC ATCAACATGT GGCAGGAGGT GGGCAAGGCC      1380
ATGTACGCCC CCCCCATCGA GGGCCAGATC CGGTGCAGCA GCAACATCAC CGGTCTGCTG      1440
CTGACCCGCG ACGGCGGCAA GGACACCGAC ACCAACGACA CCGAAATCTT CCGCCCCGGC      1500
GGCGGCGACA TGCGCGACAA CTGGAGATCT GAGCTGTACA AGTACAAGGT GGTGACGATC      1560
GAGCCCCTGG GCGTGGCCCC CACCAAGGCC AAGCGCCGCG TGGTGCAGCG CGAGAAGCGC      1620
TAAAGCGGCC GC                                                          1632
```

(2) INFORMATION FOR SEQ ID NO:35:

(i) SEQUENCE CHARACTERISTICS:
        (A) LENGTH: 2481 base pairs
        (B) TYPE: nucleic acid
        (C) STRANDEDNESS: double (D) TOPOLOGY: linear (ii) MOLECULE TYPE: cDNA (xi) SEQUENCE DESCRIPTION: SEQ ID NO:35:

| | | | | |
|---|---|---|---|---|
| ACCGAGAAGC | TGTGGGTGAC | CGTGTACTAC | GGCGTGCCCG | TGTGGAAGGA GGCCACCACC | 60 |
| ACCCTGTTCT | GCGCCAGCGA | CGCCAAGGCG | TACGACACCG | AGGTGCACAA CGTGTGGGCC | 120 |
| ACCCAGGCGT | GCGTGCCCAC | CGACCCCAAC | CCCCAGGAGG | TGGAGCTCGT GAACGTGACC | 180 |
| GAGAACTTCA | ACATGTGGAA | GAACAACATG | CTGGAGCAGA | TGCATGAGGA CATCATCAGC | 240 |
| CTGTGGGACC | AGAGCCTGAA | GCCCTGCGTG | AAGCTGACCC | CCCTGTGCGT GACCCTGAAC | 300 |
| TGCACCGACC | TGAGGAACAC | CACCAACACC | AACAACAGCA | CCGCCAACAA CAACAGCAAC | 360 |
| AGCGAGGGCA | CCATCAAGGG | CGGCGAGATG | AAGAACTGCA | GCTTCAACAT CACCACCAGC | 420 |
| ATCCGCGACA | AGATGCAGAA | GGAGTACGCC | CTGCTGTACA | AGCTGGATAT CGTGAGCATC | 480 |
| CACAACGACA | GCACCAGCTA | CCGCCTGATC | TCCTGCAACA | CCAGCGTGAT CACCCAGGCC | 540 |
| TGCCCCAAGA | TCAGCTTCGA | GCCCATCCCC | ATCCACTACT | GCGCCCCCGC CGGCTTCGCC | 600 |
| ATCCTGAAGT | GCAACGACAA | GAAGTTCAGC | GGCAAGGGCA | GCTGCAAGAA CGTGACCACC | 660 |
| GTGCAGTGCA | CCCACGGCAT | CCGGCCGGTG | GTGAGCACCC | AGCTCCTGCT GAACGGCAGC | 720 |
| CTGGCCGAGG | AGGAGGTGGT | GATCCGCAGC | GAGAACTTCA | CCGACAACGC CAAGACCATC | 780 |
| ATCGTGCACC | TGAATGAGAG | CGTGCAGATC | AACTGCACGC | GTCCCAACTA CAACAAGCGC | 840 |
| AAGCGCATCC | ACATCGGCCC | CGGGCGCGCC | TTCTACACCA | CCAAGAACAT CATCGGCACC | 900 |
| ATCCGCCAGG | CCCACTGCAA | CATCTCTAGA | GCCAAGTGGA | ACGACACCCT GCGCCAGATC | 960 |
| GTGAGCAAGC | TGAAGGAGCA | GTTCAAGAAC | AAGACCATCG | TGTTCAACCA GAGCAGCGGC | 1020 |
| GGCGACCCCG | AGATCGTGAT | GCACAGCTTC | AACTGCGGCG | GCGAATTCTT CTACTGCAAC | 1080 |
| ACCAGCCCCC | TGTTCAACAG | CACCTGGAAC | GGCAACAACA | CCTGGAACAA CACCACCGGC | 1140 |
| AGCAACAACA | ATATTACCCT | CCAGTGCAAG | ATCAAGCAGA | TCATCAACAT GTGGCAGGAG | 1200 |
| GTGGGCAAGG | CCATGTACGC | CCCCCCCATC | GAGGGCCAGA | TCCGGTGCAG CAGCAACATC | 1260 |
| ACCGGTCTGC | TGCTGACCCG | CGACGGCGGC | AAGGACACCG | ACACCAACGA CACCGAAATC | 1320 |
| TTCCGCCCCG | GCGGCGGCGA | CATGCGCGAC | AACTGGAGAT | CTGAGCTGTA CAAGTACAAG | 1380 |
| GTGGTGACGA | TCGAGCCCCT | GGGCGTGGCC | CCCACCAAGG | CCAAGCGCCG CGTGGTGCAG | 1440 |
| CGCGAGAAGC | GGGCCGCCAT | CGGCGCCCTG | TTCCTGGGCT | TCCTGGGGGC GGCGGGCAGC | 1500 |
| ACCATGGGGG | CCGCCAGCGT | GACCCTGACC | GTGCAGGCCC | GCCTGCTCCT GAGCGGCATC | 1560 |
| GTGCAGCAGC | AGAACAACCT | CCTCCGCGCC | ATCGAGGCCC | AGCAGCATAT GCTCCAGCTC | 1620 |
| ACCGTGTGGG | GCATCAAGCA | GCTCCAGGCC | CGCGTGCTGG | CCGTGGAGCG CTACCTGAAG | 1680 |
| GACCAGCAGC | TCCTGGGCTT | CTGGGGCTGC | TCCGGCAAGC | TGATCTGCAC CACCACGGTA | 1740 |
| CCCTGGAACG | CCTCCTGGAG | CAACAAGAGC | CTGGACGACA | TCTGGAACAA CATGACCTGG | 1800 |
| ATGCAGTGGG | AGCGCGAGAT | CGATAACTAC | ACCAGCCTGA | TCTACAGCCT GCTGGAGAAG | 1860 |
| AGCCAGACCC | AGCAGGAGAA | GAACGAGCAG | GAGCTGCTGG | AGCTGGACAA CTGGGCGAGC | 1920 |
| CTGTGGAACT | GGTTCGACAT | CACCAACTGG | CTGTGGTACA | TCAAAATCTT CATCATGATT | 1980 |
| GTGGGCGGCC | TGGTGGGCCT | CCGCATCGTG | TTCGCCGTGC | TGAGCATCGT GAACCGCGTG | 2040 |
| CGCCAGGGCT | ACAGCCCCCT | GAGCCTCCAG | ACCCGGCCCC | CCGTGCCGCG CGGGCCCGAC | 2100 |
| CGCCCCGAGG | GCATCGAGGA | GGAGGGCGGC | GAGCGCGACC | GCGACACCAG CGGCAGGCTC | 2160 |
| GTGCACGGCT | TCCTGGCGAT | CATCTGGGTC | GACCTCCGCA | GCCTGTTCCT GTTCAGCTAC | 2220 |

```
CACCACCGCG ACCTGCTGCT GATCGCCGCC CGCATCGTGG AACTCCTAGG CCGCCGCGGC    2280

TGGGAGGTGC TGAAGTACTG GTGGAACCTC CTCCAGTATT GGAGCCAGGA GCTGAAGTCC    2340

AGCGCCGTGA GCCTGCTGAA CGCCACCGCC ATCGCCGTGG CCGAGGGCAC CGACCGCGTG    2400

ATCGAGGTGC TCCAGAGGGC CGGGAGGGCG ATCCTGCACA TCCCCACCCG CATCCGCCAG    2460

GGGCTCGAGA GGGCGCTGCT G                                              2481
```

(2) INFORMATION FOR SEQ ID NO:36:

(i) SEQUENCE CHARACTERISTICS:
        (A) LENGTH: 486 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:36:

```
ATGAATCCAG TAATAAGTAT AACATTATTA TTAAGTGTAT TACAAATGAG TAGAGGACAA      60

AGAGTAATAA GTTTAACAGC ATGTTTAGTA AATCAAAATT TGAGATTAGA TTGTAGACAT     120

GAAAATAATA CACCTTTGCC AATACAACAT GAATTTTCAT TAACGCGTGA AAAAAAAAAA     180

CATGTATTAA GTGGAACATT AGGAGTACCA GAACATACAT ATAGAAGTAG AGTAAATTTG     240

TTTAGTGATA GATTCATAAA AGTATTAACA TTAGCAAATT TTACAACAAA AGATGAAGGA     300

GATTATATGT GTGAGCTCAG AGTAAGTGGA CAAAATCCAA CAAGTAGTAA TAAAACAATA     360

AATGTAATAA GAGATAAATT AGTAAAATGT GGAGGAATAA GTTTATTAGT ACAAAATACA     420

AGTTGGTTAT TATTATTATT ATTAAGTTTA AGTTTTTTAC AAGCAACAGA TTTTATAAGT     480

TTATGA                                                                486
```

(2) INFORMATION FOR SEQ ID NO:37:

(i) SEQUENCE CHARACTERISTICS:
        (A) LENGTH: 485 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:37:

```
ATGAACCCAG TCATCAGCAT CACTCTCCTG CTTTCAGTCT TGCAGATGTC CCGAGGACAG      60

AGGGTGATCA GCCTGACAGC CTGCCTGGTG AACAGAACCT TCGACTGGAC TGCCGTCATG     120

AGAATAACAC CAACTTGCCC ATCCAGCATG AGTTCAGCCT GACCCGAGAG AAGAAGAAGC     180

ACGTGCTGTC AGGCACCCTG GGGGTTCCCG AGCACACTTA CCGCTCCCGC GTCAACCTTT     240

TCAGTGACCG CTTTATCAAG GTCCTTACTC TAGCCAACTT GACCACCAAG GATGAGGGCG     300

ACTACATGTG TGAACTTCGA GTCTCGGGCC AGAATCCCAC AAGCTCCAAT AAAACTATCA     360

ATGTGATCAG AGACAAGCTG GTCAAGTGTG GTGGCATAAG CCTGCTGGTT CAAAACACTT     420

CCTGGCTGCT GCTGCTCCTG CTTTCCCTCT CCTTCCTCCA AGCCACGGAC TTCATTTCTC     480

TGTGA                                                                 485
```

(2) INFORMATION FOR SEQ ID NO:38:

(i) SEQUENCE CHARACTERISTICS:
        (A) LENGTH: 33 base pairs
        (B) TYPE: nucleic acid (C) STRANDEDNESS: single
        (D) TOPOLOGY: linear (ii) MOLECULE TYPE: Other (xi) SEQUENCE DESCRIPTION: SEQ ID NO:38:

CGCGGGGCTA GCGCAAAGAG TAATAAGTTT AAC                                    33

(2) INFORMATION FOR SEQ ID NO:39:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:39:

CGCGGATCCC TTGTATTTTG TACTAATA                                          28

(2) INFORMATION FOR SEQ ID NO:40:

(i) SEQUENCE CHARACTERISTICS:
        (A) LENGTH: 762 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:40:

GAATTCACGC GTAAGCTTGC CGCCACCATG GTGAGCAAGG GCGAGGAGCT GTTCACCGGG        60

GTGGTGCCCA TCCTGGTCGA GCTGGACGGC GACGTGAACG GCCACAAGTT CAGCGTGTCC       120

GGCGAGGGCG AGGGCGATGC CACCTACGGC AAGCTGACCC TGAAGTTCAT CTGCACCACC       180

GGCAAGCTGC CCGTGCCCTG GCCCACCCTC GTGACCACCT TCAGCTACGG CGTGCAGTGC       240

TTCAGCCGCT ACCCCGACCA CATGAAGCAG CACGACTTCT TCAAGTCCGC CATGCCCGAA       300

GGCTACGTCC AGGAGCGCAC CATCTTCTTC AAGGACGACG GCAACTACAA GACCCGCGCC       360

GAGGTGAAGT TCGAGGGCGA CACCCTGGTG AACCGCATCG AGCTGAAGGG CATCGACTTC       420

AAGGAGGACG GCAACATCCT GGGGCACAAG CTGGAGTACA ACTACAACAG CCACAACGTC       480

TATATCATGG CCGACAAGCA GAAGAACGGC ATCAAGGTGA ACTTCAAGAT CCGCCACAAC       540

ATCGAGGACG GCAGCGTGCA GCTCGCCGAC CACTACCAGC AGAACACCCC CATCGGCGAC       600

GGCCCCGTGC TGCTGCCCGA CAACCACTAC CTGAGCACCC AGTCCGCCCT GAGCAAAGAC       660

CCCAACGAGA AGCGCGATCA CATGGTCCTG CTGGAGTTCG TGACCGCCGC CGGGATCACT       720

CACGGCATGG ACGAGCTGTA CAAGTAAAGC GGCCGCGGAT CC                         762

(2) INFORMATION FOR SEQ ID NO:41:

(i) SEQUENCE CHARACTERISTICS:
        (A) LENGTH: 4670 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:41:

AAGCTTAAAC CATGCCCATG GGGTCTCTGC AACCGCTGGC CACCTTGTAC CTGCTGGGGA        60

TGCTGGTCGC TTCCGTGCTA GCCGCCACCA GAAGATACTA CCTGGGTGCA GTGGAACTGT       120

-continued

| | |
|---|---|
| CATGGGACTA TATGCAAAGT GATCTCGGTG AGCTGCCTGT GGACGCAAGA TTTCCTCCTA | 180 |
| GAGTGCCAAA ATCTTTTCCA TTCAACACCT CAGTCGTGTA CAAAAAGACT CTGTTTGTAG | 240 |
| AATTCACGGA TCACCTTTTC AACATCGCTA AGCCAAGGCC ACCCTGGATG GGTCTGCTAG | 300 |
| GTCCTACCAT CCAGGCTGAG GTTTATGATA CAGTGGTCAT TACACTTAAG AACATGGCTT | 360 |
| CCCATCCTGT CAGTCTTCAT GCTGTTGGTG TATCCTACTG GAAAGCTTCT GAGGGAGCTG | 420 |
| AATATGATGA TCAGACCAGT CAAAGGGAGA AGAAGATGA TAAAGTCTTC CCTGGTGGAA | 480 |
| GCCATACATA TGTCTGGCAG GTCCTGAAAG AGAATGGTCC AATGGCCTCT GACCCACTGT | 540 |
| GCCTTACCTA CTCATATCTT TCTCATGTGG ACCTGGTAAA AGACTTGAAT TCAGGCCTCA | 600 |
| TTGGAGCCCT ACTAGTATGT AGAGAAGGGA GTCTGGCCAA GGAAAAGACA CAGACCTTGC | 660 |
| ACAAATTTAT ACTACTTTTT GCTGTATTTG ATGAAGGGAA AGTTGGCAC TCAGAAACAA | 720 |
| AGAACTCCTT GATGCAGGAT AGGGATGCTG CATCTGCTCG GGCCTGGCCT AAAATGCACA | 780 |
| CAGTCAATGG TTATGTAAAC AGGTCTCTGC CAGGTCTGAT TGGATGCCAC AGGAAATCAG | 840 |
| TCTATTGGCA TGTGATTGGA ATGGGCACCA CTCCTGAAGT GCACTCAATA TTCCTCGAAG | 900 |
| GTCACACATT TCTTGTGAGG AACCATCGCC AGGCGTCCTT GGAAATCTCG CCAATAACTT | 960 |
| TCCTTACTGC TCAAACACTC TTGATGGACC TTGGACAGTT TCTACTGTTT TGTCATATCT | 1020 |
| CTTCCCACCA ACATGATGGC ATGGAAGCTT ATGTCAAAGT AGACAGCTGT CCAGAGGAAC | 1080 |
| CCCAACTACG AATGAAAAAT AATGAAGAAG CGGAAGACTA TGATGATGAT CTTACTGATT | 1140 |
| CTGAAATGGA TGTGGTCAGG TTTGATGATG ACAACTCTCC TTCCTTTATC CAAATTCGCT | 1200 |
| CAGTTGCCAA GAAGCATCCT AAAACTTGGG TACATTACAT TGCTGCTGAA GAGGAGGACT | 1260 |
| GGGACTATGC TCCCTTAGTC CTCGCCCCCG ATGACAGAAG TTATAAAAGT CAATATTTGA | 1320 |
| ACAATGGCCC TCAGCGGATT GGTAGGAAGT ACAAAAAAGT CCGATTTATG GCATACACAG | 1380 |
| ATGAAACCTT TAAGACTCGT GAAGCTATTC AGCATGAATC AGGAATCTTG GGACCTTTAC | 1440 |
| TTTATGGGGA AGTTGGAGAC ACACTGTTGA TTATATTTAA GAATCAAGCA AGCAGACCAT | 1500 |
| ATAACATCTA CCCTCACGGA ATCACTGATG TCCGTCCTTT GTATTCAAGG AGATTACCAA | 1560 |
| AAGGTGTAAA ACATTTGAAG GATTTTCCAA TTCTGCCAGG AGAAATATTC AAATATAAAT | 1620 |
| GGACAGTGAC TGTAGAAGAT GGGCCAACTA AATCAGATCC TCGGTGCCTG ACCCGCTATT | 1680 |
| ACTCTAGTTT CGTTAATATG GAGAGAGATC TAGCTTCAGG ACTCATTGGC CCTCTCCTCA | 1740 |
| TCTGCTACAA AGAATCTGTA GATCAAAGAG GAAACCAGAT AATGTCAGAC AAGAGGAATG | 1800 |
| TCATCCTGTT TTCTGTATTT GATGAGAACC GAAGCTGGTA CCTCACAGAG AATATACAAC | 1860 |
| GCTTTCTCCC CAATCCAGCT GGAGTGCAGC TTGAGGATCC AGAGTTCCAA GCCTCCAACA | 1920 |
| TCATGCACAG CATCAATGGC TATGTTTTTG ATAGTTTGCA GTTGTCAGTT TGTTTGCATG | 1980 |
| AGGTGGCATA CTGGTACATT CTAAGCATTG GAGCACAGAC TGACTTCCTT TCTGTCTTCT | 2040 |
| TCTCTGGATA TACCTTCAAA CACAAAATGG TCTATGAAGA CACACTCACC CTATTCCCAT | 2100 |
| TCTCAGGAGA AACTGTCTTC ATGTCGATGG AAAACCCAGG TCTATGGATT CTGGGGTGCC | 2160 |
| ACAACTCAGA CTTTCGGAAC AGAGGCATGA CCGCCTTACT GAAGGTTTCT AGTTGTGACA | 2220 |
| AGAACACTGG TGATTATTAC GAGGACAGTT ATGAAGATAT TTCAGCATAC TTGCTGAGTA | 2280 |
| AAAACAATGC CATTGAACCA AGAAGCTTCT CCCAGAATTC AAGACACCCT AGCACTAGGC | 2340 |
| AAAAGCAATT TAATGCCACC CCACCAGTCT TGAAACGCCA TCAACGGGAA ATAACTCGTA | 2400 |
| CTACTCTTCA GTCAGATCAA GAGGAAATTG ACTATGATGA TACCATATCA GTTGAAATGA | 2460 |

-continued

```
AGAAGGAAGA TTTTGACATT TATGATGAGG ATGAAAATCA GAGCCCCCGC AGCTTTCAAA    2520

AGAAAACACG ACACTATTTT ATTGCTGCAG TGGAGAGGCT CTGGGATTAT GGGATGAGTA    2580

GCTCCCCACA TGTTCTAAGA AACAGGGCTC AGAGTGGCAG TGTCCCTCAG TTCAAGAAAG    2640

TTGTTTTCCA GGAATTTACT GATGGCTCCT TTACTCAGCC CTTATACCGT GGAGAACTAA    2700

ATGAACATTT GGGACTCCTG GGGCCATATA TAAGAGCAGA AGTTGAAGAT AATATCATGG    2760

TAACTTTCAG AAATCAGGCC TCTCGTCCCT ATTCCTTCTA TTCTAGCCTT ATTTCTTATG    2820

AGGAAGATCA GAGGCAAGGA GCAGAACCTA GAAAAAACTT TGTCAAGCCT AATGAAACCA    2880

AAACTTACTT TTGGAAAGTG CAACATCATA TGGCACCCAC TAAAGATGAG TTTGACTGCA    2940

AAGCCTGGGC TTATTTCTCT GATGTTGACC TGGAAAAAGA TGTGCACTCA GGCCTGATTG    3000

GACCCCTTCT GGTCTGCCAC ACTAACACAC TGAACCCTGC TCATGGGAGA CAAGTGACAG    3060

TACAGGAATT TGCTCTGTTT TTCACCATCT TTGATGAGAC CAAAAGCTGG TACTTCACTG    3120

AAAATATGGA AAGAAACTGC AGGGCTCCCT GCAATATCCA GATGGAAGAT CCCACTTTTA    3180

AAGAGAATTA TCGCTTCCAT GCAATCAATG GCTACATAAT GGATACACTA CCTGGCTTAG    3240

TAATGGCTCA GGATCAAAGG ATTCGATGGT ATCTGCTCAG CATGGGCAGC AATGAAAACA    3300

TCCATTCTAT TCATTTCAGT GGACATGTGT TCACTGTACG AAAAAAAGAG GAGTATAAAA    3360

TGGCACTGTA CAATCTCTAT CCAGGTGTTT TTGAGACAGT GGAAATGTTA CCATCCAAAG    3420

CTGGAATTTG GCGGGTGGAA TGCCTTATTG GCGAGCATCT ACATGCTGGG ATGAGCACAC    3480

TTTTTCTGGT GTACAGCAAT AAGTGTCAGA CTCCCCTGGG AATGGCTTCT GGACACATTA    3540

GAGATTTTCA GATTACAGCT TCAGGACAAT ATGGACAGTG GGCCCCAAAG CTGGCCAGAC    3600

TTCATTATTC CGGATCAATC AATGCCTGGA GCACCAAGGA GCCCTTTTCT TGGATCAAGG    3660

TGGATCTGTT GGCACCAATG ATTATTCACG GCATCAAGAC CCAGGGTGCC CGTCAGAAGT    3720

TCTCCAGCCT CTACATCTCT CAGTTTATCA TCATGTATAG TCTTGATGGG AAGAAGTGGC    3780

AGACTTATCG AGGAAATTCC ACTGGAACCT TAATGGTCTT CTTTGGCAAT GTGGATTCAT    3840

CTGGGATAAA ACACAATATT TTTAACCCTC CAATTATTGC TCGATACATC CGTTTGCACC    3900

CAACTCATTA TAGCATTCGC AGCACTCTTC GCATGGAGTT GATGGGCTGT GATTTAAATA    3960

GTTGCAGCAT GCCATTGGGA ATGGAGAGTA AAGCAATATC AGATGCACAG ATTACTGCTT    4020

CATCCTACTT TACCAATATG TTTGCCACCT GGTCTCCTTC AAAAGCTCGA CTTCACCTCC    4080

AAGGGAGGAG TAATGCCTGG AGACCTCAGG TGAATAATCC AAAAGAGTGG CTGCAAGTGG    4140

ACTTCCAGAA GACAATGAAA GTCACAGGAG TAACTACTCA GGGAGTAAAA TCTCTGCTTA    4200

CCAGCATGTA TGTGAAGGAG TTCCTCATCT CCAGCAGTCA AGATGGCCAT CAGTGGACTC    4260

TCTTTTTTCA GAATGGCAAA GTAAAGGTTT TCAGGGAAA TCAAGACTCC TTCACACCTG    4320

TGGTGAACTC TCTAGACCCA CCGTTACTGA CTCGCTACCT TCGAATTCAC CCCCAGAGTT    4380

GGGTGCACCA GATTGCCCTG AGGATGGAGG TTCTGGGCTG CGAGGCACAG GACCTCTACT    4440

GAGGGTGGCC ACTGCAGCAC CTGCCACTGC CGTCACCTCT CCCTCCTCAG CTCCAGGGCA    4500

GTGTCCCTCC CTGGCTTGCC TTCTACCTTT GTGCTAAATC CTAGCAGACA CTGCCTTGAA    4560

GCCTCCTGAA TTAACTATCA TCAGTCCTGC ATTTCTTTGG TGGGGGGCCA GGAGGGTGCA    4620

TCCAATTTAA CTTAACTCTT ACCGTCGACC TGCAGGCCCA ACGCGGCCGC              4670
```

(2) INFORMATION FOR SEQ ID NO:42:

(i) SEQUENCE CHARACTERISTICS:
        (A) LENGTH: 4451 base pairs (B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO:42:

| | | | | | |
|---|---|---|---|---|---|
| AAGCTTAAAC | CATGCCCATG | GGGTCTCTGC | AACCGCTGGC | CACCTTGTAC | CTGCTGGGGA | 60
| TGCTGGTCGC | TTCCGTGCTA | GCCGCCACCC | GCCGCTACTA | CCTGGGCGCC | GTGGAGCTGT | 120
| CCTGGGACTA | CATGCAGAGC | GACCTGGGCG | AGCTCCCCGT | GGACGCCCGC | TTCCCCCCCC | 180
| GCGTGCCCAA | GAGCTTCCCC | TTCAACACCA | GCGTGGTGTA | CAAGAAAACC | CTGTTCGTGG | 240
| AGTTCACCGA | CCACCTGTTC | AACATTGCCA | AGCCGCGCCC | CCCCTGGATG | GGCCTGCTGG | 300
| GCCCCACCAT | CCAGGCCGAG | GTGTACGACA | CCGTGGTGAT | CACCCTGAAG | AACATGGCCA | 360
| GCCACCCCGT | CAGCCTGCAC | GCCGTGGGCG | TGAGCTACTG | GAAGGCCAGC | GAGGGCGCCG | 420
| AGTACGACGA | CCAGACGTCC | CAGCGCGAGA | AGGAGGACGA | CAAGGTGTTC | CCGGGGGGA | 480
| GCCACACCTA | CGTGTGGCAG | GTGCTTAAGG | AGAACGGCCC | TATGGCCAGC | GACCCCCTGT | 540
| GCCTGACCTA | CAGCTACCTG | AGCCACGTGG | ACCTGGTGAA | GGATCTGAAC | AGCGGGCTGA | 600
| TCGGCGCCCT | GCTGGTGTGT | CGCGAGGGCA | GCCTGGCCAA | GGAGAAAACC | CAGACCCTGC | 660
| ACAAGTTCAT | CCTGCTGTTC | GCCGTGTTCG | ACGAGGGGAA | GAGCTGGCAC | AGCGAGACTA | 720
| AGAACAGCCT | GATGCAGGAC | CGCGACGCCG | CCAGCGCCCG | CGCCTGGCCC | AAGATGCACA | 780
| CCGTTAACGG | CTACGTGAAC | CGCAGCCTGC | CCGGCCTGAT | CGGCTGCCAC | CGCAAGAGCG | 840
| TGTACTGGCA | CGTCATCGGC | ATGGGCACCA | CCCCTGAGGT | GCACAGCATC | TTCCTGGAGG | 900
| GCCACACCTT | CCTGGTGCGC | AACCACCGCC | AGGCCAGCCT | GGAGATCAGC | CCCATCACCT | 960
| TCCTGACTGC | CCAGACCCTG | CTGATGGACC | TAGGCCAGTT | CCTGCTGTTC | TGCCACATCA | 1020
| GCAGCCACCA | GCACGACGGC | ATGGAGGCTT | ACGTGAAGGT | GGACAGCTGC | CCCGAGGAGC | 1080
| CCCAGCTGCG | CATGAAGAAC | AACGAGGAGG | CCGAGGACTA | CGACGACGAC | CTGACCGACA | 1140
| GCGAGATGGA | TGTCGTACGC | TTCGACGACG | ACAACAGCCC | CAGCTTCATC | CAGATCCGCA | 1200
| GCGTGGCCAA | GAAGCACCCT | AAGACCTGGG | TGCACTACAT | CGCCGCCGAG | GAGGAGGACT | 1260
| GGGACTACGC | CCCGCTAGTA | CTGGCCCCCG | ACGACCGCAG | CTACAAGAGC | CAGTACCTGA | 1320
| ACAACGGCCC | CCAGCGCATC | GGCCGCAAGT | ACAAGAAGGT | GCGCTTCATG | GCCTACACCG | 1380
| ACGAGACTTT | CAAGACCCGC | GAGGCCATCC | AGCACGAGTC | CGGCATCCTC | GGCCCCCTGC | 1440
| TGTACGGCGA | GGTGGGCGAC | ACCCTGCTGA | TCATCTTCAA | GAACCAGGCC | AGCAGGCCCT | 1500
| ACAACATCTA | CCCCCACGGC | ATCACCGACG | TGCGCCCCCT | GTACAGCCGC | CGCCTGCCCA | 1560
| AGGGCGTGAA | GCACCTGAAG | GACTTCCCCA | TCCTGCCCGG | CGAGATCTTC | AAGTACAAGT | 1620
| GGACCGTGAC | CGTGGAGGAC | GGCCCCACCA | AGAGCGACCC | CCGCTGCCTG | ACCCGCTACT | 1680
| ACAGCAGCTT | CGTGAACATG | GAGCGCGACC | TGGCCTCCGG | ACTGATCGGC | CCCCTGCTGA | 1740
| TCTGCTACAA | GGAGAGCGTG | GACCAGCGCG | GCAACCAGAT | CATGAGCGAC | AAGCGCAACG | 1800
| TGATCCTGTT | CAGCGTGTTC | GACGAGAACC | GCAGCTGGTA | TCTGACCGAG | AACATCCAGC | 1860
| GCTTCCTGCC | CAACCCCGCT | GGCGTGCAGC | TGGAAGATCC | CGAGTTCCAG | GCCAGCAACA | 1920
| TCATGCACAG | CATCAACGGC | TACGTGTTCG | ACAGCCTGCA | GCTGAGCGTG | TGCCTGCATG | 1980
| AGGTGGCCTA | CTGGTACATC | CTGAGCATCG | GCGCCCAGAC | CGACTTCCTG | AGCGTGTTCT | 2040
| TCTCCGGGTA | TACCTTCAAG | CACAAGATGG | TGTACGAGGA | CACCCTGACC | CTGTTCCCCT | 2100
| TCTCCGGCGA | GACTGTGTTC | ATGTCTATGG | AGAACCCCGG | CCTGTGGATT | CTGGGCTGCC | 2160

-continued

```
ACAACAGCGA CTTCCGCAAC CGCGGCATGA CTGCCCTGCT GAAAGTCTCC AGCTGCGACA    2220

AGAACACCGG CGACTACTAC GAGGACAGCT ACGAGGACAT CTCCGCCTAC CTGCTGTCCA    2280

AGAACAACGC CATCGAGCCC CGCTCCTTCT CCCAAAACTC CCGCCACCCC AGCACGCGTC    2340

AGAAGCAGTT CAACGCCACC CCCCCCGTGC TGAAGCGCCA CCAGCGCGAG ATCACCCGCA    2400

CCACCCTGCA AAGCGACCAG GAGGAGATCG ACTACGACGA CACCATCAGC GTGGAGATGA    2460

AGAAGGAGGA CTTCGACATC TACGACGAGG ACGAGAACCA GAGCCCCCGC TCCTTCCAAA    2520

AGAAAACCCG CCACTACTTC ATCGCCGCCG TGGAGCGCCT GTGGGACTAC GGCATGAGCA    2580

GCAGCCCCCA CGTCCTGCGC AACCGCGCCC AGAGCGGCAG CGTGCCCCAG TTCAAGAAGG    2640

TGGTGTTCCA GGAGTTCACC GACGGCAGCT TCACCCAGCC CCTGTACCGC GGCGAGCTGA    2700

ACGAGCACCT GGGCCTGCTC GGCCCCTACA TCCGCGCCGA GGTGGAGGAC AACATCATGG    2760

TGACCTTCCG CAACCAAGCC TCCCGGCCCT ACTCCTTCTA CTCCTCCCTG ATCAGCTACG    2820

AGGAGGACCA GCGCCAGGGC GCCGAGCCCC GCAAGAACTT CGTGAAGCCC AACGAGACTA    2880

AGACCTACTT CTGGAAGGTG CAGCACCACA TGGCCCCCAC CAAGGACGAG TTCGACTGCA    2940

AGGCCTGGGC CTACTTCAGC GACGTGGACC TGGAGAAGGA CGTGCACAGC GGCCTGATCG    3000

GCCCCCTGCT GGTGTGCCAC ACCAACACCC TGAACCCCCC CCACGGGAGG CAGGTGACTG    3060

TGCAGGAATT TGCCCTGTTC TTCACCATCT TCGACGAGAC TAAGAGCTGG TACTTCACCG    3120

AGAACATGGA GCGCAACTGC CGCGCCCCCT GCAACATCCA GATGGAAGAT CCCACCTTCA    3180

AGGAGAACTA CCGCTTCCAC GCCATCAACG GCTACATCAT GGACACCCTG CCCGGCCTGG    3240

TGATGGCCCA GGACCAGCGC ATCCGCTGGT ACCTGCTGTC TATGGGCAGC AACGAGAACA    3300

TCCACAGCAT CCACTTCAGC GGCCACGTTT TCACCGTGCG CAAGAAGGAG GAGTACAAGA    3360

TGGCCCTGTA CAACCTGTAC CCCGGCGTGT TCGAGACTGT GGAGATGCTG CCCAGCAAGG    3420

CCGGGATCTG GCGCGTGGAG TGCCTGATCG GCGAGCACCT GCACGCCGGC ATGAGCACCC    3480

TGTTCCTGGT GTACAGCAAC AAGTGCCAGA CCCCCCTGGG CATGGCCAGC GGCCACATCC    3540

GCGACTTCCA GATCACCGCC AGCGGCCAGT ACGGCCAGTG GGCTCCCAAG CTGGCCCGCC    3600

TGCACTACAG CGGCAGCATC AACGCCTGGT CGACCAAGGA GCCCTTCTCC TGGATCAAGG    3660

TGGACCTGCT GGCCCCCATG ATCATCCACG GCATCAAGAC CCAGGGCGCC CGCCAGAAGT    3720

TCAGCAGCCT GTACATCAGC CAGTTCATCA TCATGTACTC TCTAGACGGC AAGAAGTGGC    3780

AGACCTACCG CGGCAACAGC ACCGGCACCC TGATGGTGTT CTTCGGCAAC GTGGACAGCA    3840

GCGGCATCAA GCACAACATC TTCAACCCCC CCATCATCGC CCGCTACATC CGCCTGCACC    3900

CCACCCACTA CAGCATCCGC AGCACCCTGC GCATGGAGCT GATGGGCTGC GACCTGAACA    3960

GCTGCAGCAT GCCCCTGGGC ATGGAGAGCA AGGCCATCAG CGACGCCCAG ATCACCGCCT    4020

CCAGCTACTT CACCAACATG TTCGCCACCT GGAGCCCCAG CAAGGCCCGC CTGCACCTGC    4080

AGGGCCGCAG CAACGCCTGG CGCCCCCAGG TGAACAACCC CAAGGAGTGG CTGCAGGTGG    4140

ACTTCCAGAA AACCATGAAG GTGACTGGCG TGACCACCCA GGGCGTCAAG AGCCTGCTGA    4200

CCAGCATGTA CGTGAAGGAG TTCCTGATCA GCAGCAGCCA GGACGGCCAC CAGTGGACCC    4260

TGTTCTTCCA AAACGGCAAG GTGAAGGTGT TCCAGGGCAA CCAGGACAGC TTCACACCGG    4320

TCGTGAACAG CCTGGACCCC CCCCTGCTGA CCCGCTACCT GCGCATCCAC CCCCAGAGCT    4380

GGGTGCACCA GATCGCCCTG CGCATGGAGG TGCTGGGCTG CGAGGCCCAG GACCTGTACT    4440

GAAGCGGCCG C                                                        4451
```

(2) INFORMATION FOR SEQ ID NO:43:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:43:

GGGGATCCTC ACGTCTCA                                        18

(2) INFORMATION FOR SEQ ID NO:44:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:44:

CTGCTTCTGA CGCGTGCTGG GGTGGCGGGA GTT                    33

(2) INFORMATION FOR SEQ ID NO:45:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:45:

CTGCTGAAAG TCTCCAGCTG C                                  21

(2) INFORMATION FOR SEQ ID NO:46:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:46:

GGCAGGTGCT TAAGGAGAAC GGCCCTATGG CCA                    33

(2) INFORMATION FOR SEQ ID NO:47:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:47:

CGCCAAGGGC TAGCCGCCAC CAGAAGATAC TACCTGGGT            39

(2) INFORMATION FOR SEQ ID NO:48:

(i) SEQUENCE CHARACTERISTICS:

```
            (A) LENGTH: 31 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:48:

CAAGACTGGT GGGGTGGCAT TAAATTGCTT T                              31

(2) INFORMATION FOR SEQ ID NO:49:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:49:

AATGCCACCC CACCAGTCTT GAAACGCCA                                 29

(2) INFORMATION FOR SEQ ID NO:50:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:50:

CATCTGGATA TTGCAGGGAG                                           20

(2) INFORMATION FOR SEQ ID NO:51:

(i) SEQUENCE CHARACTERISTICS:
            (A) LENGTH: 105 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:51:

CGCGAATTCG GAAGACCCGC TAGCCGCCAC CCGCCGCTAC TACCTGGGCG CCGTGGAGCT    60

GTCCTGGGAC TACATGCAGA GCGACCTGGG CGAGCTCCCC GTGGA                  105

(2) INFORMATION FOR SEQ ID NO:52:

(i) SEQUENCE CHARACTERISTICS:
            (A) LENGTH: 104 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:52:

GGGGATCCTC ACGTCTCAGG TTTTCTTGTA CACCACGCTG GTGTTGAAGG GGAAGCTCTT    60

GGGCACGCGG GGGGGGAAGC GGGCGTCCAC GGGGAGCTCG CCCA                   104

(2) INFORMATION FOR SEQ ID NO:53:

(i) SEQUENCE CHARACTERISTICS:
```

(A) LENGTH: 105 base pairs
           (B) TYPE: nucleic acid
           (C) STRANDEDNESS: single
           (D) TOPOLOGY: linear (ii) MOLECULE TYPE: Other (xi) SEQUENCE DESCRIPTION: SEQ ID NO:53:

CGCGAATTCG AAGACCCAA CCCTGTTCGT GGAGTTCACC GACCACCTGT TCAACATTGC      60

CAAGCCGCGC CCCCCCTGGA TGGGCCTGCT GGGCCCCACC ATCCA      105

(2) INFORMATION FOR SEQ ID NO:54:

(i) SEQUENCE CHARACTERISTICS:
           (A) LENGTH: 104 base pairs
           (B) TYPE: nucleic acid
           (C) STRANDEDNESS: single
           (D) TOPOLOGY: linear (ii) MOLECULE TYPE: Other (xi) SEQUENCE DESCRIPTION: SEQ ID NO:54:

GGGGATCCTC ACGTCTCAGT GCAGGCTGAC GGGGTGGCTG GCCATGTTCT TCAGGGTGAT      60

CACCACGGTG TCGTACACCT CGGCCTGGAT GGTGGGGCCC AGCA       104

(2) INFORMATION FOR SEQ ID NO:55:

(i) SEQUENCE CHARACTERISTICS:
           (A) LENGTH: 105 base pairs
           (B) TYPE: nucleic acid
           (C) STRANDEDNESS: single
           (D) TOPOLOGY: linear (ii) MOLECULE TYPE: Other (xi) SEQUENCE DESCRIPTION: SEQ ID NO:55:

CGCGAATTCG AAGACCCGC ACGCCGTGGG CGTGAGCTAC TGGAAGGCCA GCGAGGGCGC      60

CGAGTACGAC GACCAGACGT CCCAGCGCGA GAAGGAGGAC GACAA      105

(2) INFORMATION FOR SEQ ID NO:56:

(i) SEQUENCE CHARACTERISTICS:
           (A) LENGTH: 104 base pairs
           (B) TYPE: nucleic acid
           (C) STRANDEDNESS: single
           (D) TOPOLOGY: linear (ii) MOLECULE TYPE: Other (xi) SEQUENCE DESCRIPTION: SEQ ID NO:56:

GGGGATCCTC ACGTCTCAGC TGGCCATAGG GCCGTTCTCC TTAAGCACCT GCCACACGTA      60

GGTGTGGCTC CCCCCGGGA ACACCTTGTC GTCCTCCTTC TCGC       104

(2) INFORMATION FOR SEQ ID NO:57:

(i) SEQUENCE CHARACTERISTICS:
           (A) LENGTH: 105 base pairs
           (B) TYPE: nucleic acid
           (C) STRANDEDNESS: single
           (D) TOPOLOGY: linear (ii) MOLECULE TYPE: Other (xi) SEQUENCE DESCRIPTION: SEQ ID NO:57:

CGCGAATTCG AAGACCCCA GCGACCCCCT GTGCCTGACC TACAGCTACC TGAGCCACGT      60

```
GGACCTGGTG AAGGATCTGA ACAGCGGGCT GATCGGCGCC CTGCT            105

(2) INFORMATION FOR SEQ ID NO:58:

(i) SEQUENCE CHARACTERISTICS:
        (A) LENGTH: 104 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:58:

GGGGATCCTC ACGTCTCAGA ACAGCAGGAT GAACTTGTGC AGGGTCTGGG TTTTCTCCTT   60

GGCCAGGCTG CCCTCGCGAC ACACCAGCAG GGCGCCGATC AGCC                  104

(2) INFORMATION FOR SEQ ID NO:59:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:59:

CGCGAATTCG GAAGACCCGT TCGCCGTGTT CGACGAGGGG AAGAGCTGGC ACAGCGAGAC   60

TAAGAACAGC CTGATGCAGG ACCGCGACGC CGCCAGCGCC CGCGC                 105

(2) INFORMATION FOR SEQ ID NO:60:

(i) SEQUENCE CHARACTERISTICS:
        (A) LENGTH: 104 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:60:

GGGGATCCTC ACGTCTCAGT GGCAGCCGAT CAGGCCGGGC AGGCTGCGGT TCACGTAGCC   60

GTTAACGGTG TGCATCTTGG GCCAGGCGCG GGCGCTGGCG GCGT                  104

(2) INFORMATION FOR SEQ ID NO:61:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:61:

CGCGAATTCG GAAGACCCCC ACCGCAAGAG CGTGTACTGG CACGTCATCG GCATGGGCAC   60

CACCCCTGAG GTGCACAGCA TCTTCCTGGA GGGCCACACC TTCCT                 105

(2) INFORMATION FOR SEQ ID NO:62:

(i) SEQUENCE CHARACTERISTICS:
        (A) LENGTH: 104 base pairs
        (B) TYPE: nucleic acid
        (C) STRANDEDNESS: single
        (D) TOPOLOGY: linear
```

(ii) MOLECULE TYPE: Other (xi) SEQUENCE DESCRIPTION: SEQ ID NO:62:

GGGGATCCTC ACGTCTCACA GGGTCTGGGC AGTCAGGAAG GTGATGGGGC TGATCTCCAG  60

GCTGGCCTGG CGGTGGTTGC GCACCAGGAA GGTGTGGCCC TCCA  104

(2) INFORMATION FOR SEQ ID NO:63:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:63:

CGCGAATTCG GAAGACCCCC TGCTGATGGA CCTAGGCCAG TTCCTGCTGT TCTGCCACAT  60

CAGCAGCCAC CAGCACGACG GCATGGAGGC TTACGTGAAG GTGGA  105

(2) INFORMATION FOR SEQ ID NO:64:

(i) SEQUENCE CHARACTERISTICS:
        (A) LENGTH: 104 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:64:

GGGGATCCTC ACGTCTCAGT CGTCGTCGTA GTCCTCGGCC TCCTCGTTGT TCTTCATGCG  60

CAGCTGGGGC TCCTCGGGGC AGCTGTCCAC CTTCACGTAA GCCT  104

(2) INFORMATION FOR SEQ ID NO:65:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:65:

CGCGAATTCG GAAGACCCCG ACCTGACCGA CAGCGAGATG GATGTCGTAC GCTTCGACGA  60

CGACAACAGC CCCAGCTTCA TCCAGATCCG CAGCGTGGCC AAGAA  105

(2) INFORMATION FOR SEQ ID NO:66:

(i) SEQUENCE CHARACTERISTICS:
        (A) LENGTH: 104 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:66:

GGGGATCCTC ACGTCTCATA CTAGCGGGGC GTAGTCCCAG TCCTCCTCCT CGGCGGCGAT  60

GTAGTGCACC CAGGTCTTAG GGTGCTTCTT GGCCACGCTG CGGA  104

(2) INFORMATION FOR SEQ ID NO:67:

(i) SEQUENCE CHARACTERISTICS:
            (A) LENGTH: 105 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:67:

CGCGAATTCG GAAGACCCAG TACTGGCCCC CGACGACCGC AGCTACAAGA GCCAGTACCT      60

GAACAACGGC CCCCAGCGCA TCGGCCGCAA GTACAAGAAG GTGCG                     105

(2) INFORMATION FOR SEQ ID NO:68:

(i) SEQUENCE CHARACTERISTICS:
            (A) LENGTH: 104 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:68:

GGGGATCCTC ACGTCTCAGA GGATGCCGGA CTCGTGCTGG ATGGCCTCGC GGGTCTTGAA      60

AGTCTCGTCG GTGTAGGCCA TGAAGCGCAC CTTCTTGTAC TTGC                      104

(2) INFORMATION FOR SEQ ID NO:69:

(i) SEQUENCE CHARACTERISTICS:
            (A) LENGTH: 105 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:69:

CGCGAATTCG GAAGACCCCC TCGGCCCCCT GCTGTACGGC GAGGTGGGCG ACACCCTGCT      60

GATCATCTTC AAGAACCAGG CCAGCAGGCC CTACAACATC TACCC                     105

(2) INFORMATION FOR SEQ ID NO:70:

(i) SEQUENCE CHARACTERISTICS:
            (A) LENGTH: 104 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:70:

GGGGATCCTC ACGTCTCACT TCAGGTGCTT CACGCCCTTG GGCAGGCGGC GGCTGTACAG      60

GGGGCGCACG TCGGTGATGC CGTGGGGGTA GATGTTGTAG GGCC                      104

(2) INFORMATION FOR SEQ ID NO:71:

(i) SEQUENCE CHARACTERISTICS:
            (A) LENGTH: 105 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:71:

CGCGAATTCG GAAGACCCGA AGGACTTCCC CATCCTGCCC GGCGAGATCT TCAAGTACAA      60

```
GTGGACCGTG ACCGTGGAGG ACGGCCCCAC CAAGAGCGAC CCCCG                      105
```

(2) INFORMATION FOR SEQ ID NO:72:

(i) SEQUENCE CHARACTERISTICS:
        (A) LENGTH: 104 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:72:

```
GGGGATCCTC ACGTCTCAGC CGATCAGTCC GGAGGCCAGG TCGCGCTCCA TGTTCACGAA      60
GCTGCTGTAG TAGCGGGTCA GGCAGCGGGG GTCGCTCTTG GTGG                       104
```

(2) INFORMATION FOR SEQ ID NO:73:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:73:

```
CGCGAATTCG GAAGACCCCG GCCCCCTGCT GATCTGCTAC AAGGAGAGCG TGGACCAGCG      60
CGGCAACCAG ATCATGAGCG ACAAGCGCAA CGTGATCCTG TTCAG                      105
```

(2) INFORMATION FOR SEQ ID NO:74:

(i) SEQUENCE CHARACTERISTICS:
        (A) LENGTH: 104 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:74:

```
GGGGATCCTC ACGTCTCAAG CGGGGTTGGG CAGGAAGCGC TGGATGTTCT CGGTCAGATA      60
CCAGCTGCGG TTCTCGTCGA ACACGCTGAA CAGGATCACG TTGC                       104
```

(2) INFORMATION FOR SEQ ID NO:75:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:75:

```
CGCGAATTCG GAAGACCCCG CTGGCGTGCA GCTGGAAGAT CCCGAGTTCC AGGCCAGCAA      60
CATCATGCAC AGCATCAACG GCTACGTGTT CGACAGCCTG CAGCT                      105
```

(2) INFORMATION FOR SEQ ID NO:76:

(i) SEQUENCE CHARACTERISTICS:
        (A) LENGTH: 104 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:76:

GGGGATCCTC ACGTCTCACA GGAAGTCGGT CTGGGCGCCG ATGCTCAGGA TGTACCAGTA    60

GGCCACCTCA TGCAGGCACA CGCTCAGCTG CAGGCTGTCG AACA                   104

(2) INFORMATION FOR SEQ ID NO:77:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:77:

CGCGAATTCG GAAGACCCCC TGAGCGTGTT CTTCTCCGGG TATACCTTCA AGCACAAGAT    60

GGTGTACGAG GACACCCTGA CCCTGTTCCC CTTCTCCGGC GAGAC                  105

(2) INFORMATION FOR SEQ ID NO:78:

(i) SEQUENCE CHARACTERISTICS:
        (A) LENGTH: 104 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:78:

GGGGATCCTC ACGTCTCAGT TGCGGAAGTC GCTGTTGTGG CAGCCCAGAA TCCACAGGCC    60

GGGGTTCTCC ATAGACATGA ACACAGTCTC GCCGGAGAAG GGA                    104

(2) INFORMATION FOR SEQ ID NO:79:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:79:

CGCGAATTCG GAAGACCCCA ACCGCGGCAT GACTGCCCTG CTGAAAGTCT CCAGCTGCGA    60

CAAGAACACC GGCGACTACT ACGAGGACAG CTACGAGGAC ATCTC                  105

(2) INFORMATION FOR SEQ ID NO:80:

(i) SEQUENCE CHARACTERISTICS:
        (A) LENGTH: 104 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:80:

GGGGATCCTC ACGTCTCAGC GGTGGCGGGA GTTTTGGGAG AAGGAGCGGG GCTCGATGGC    60

GTTGTTCTTG ACAGCAGGT AGGCGGAGAT GTCCTCGTAG CTGT                    104

(2) INFORMATION FOR SEQ ID NO:81:

(i) SEQUENCE CHARACTERISTICS:
    (A) LENGTH: 105 base pairs
    (B) TYPE: nucleic acid
    (C) STRANDEDNESS: single
    (D) TOPOLOGY: linear (ii) MOLECULE TYPE: Other (xi) SEQUENCE DESCRIPTION: SEQ ID NO:81:

```
CGCGAATTCG GAAGACCCCC GCAGCACGCG TCAGAAGCAG TTCAACGCCA CCCCCCCCGT      60

GCTGAAGCGC CACCAGCGCG AGATCACCCG CACCACCCTG CAAAG                     105
```

(2) INFORMATION FOR SEQ ID NO:82:

(i) SEQUENCE CHARACTERISTICS:
        (A) LENGTH: 104 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:82:

```
GGGGATCCTC ACGTCTCAGA TGTCGAAGTC CTCCTTCTTC ATCTCCACGC TGATGGTGTC      60

GTCGTAGTCG ATCTCCTCCT GGTCGCTTTG CAGGGTGGTG CGGG                      104
```

(2) INFORMATION FOR SEQ ID NO:83:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:83:

```
CGCGAATTCG GAAGACCCCA TCTACGACGA GGACGAGAAC CAGAGCCCCC GCTCCTTCCA      60

AAAGAAAACC CGCCACTACT TCATCGCCGC CGTGGAGCGC CTGTG                     105
```

(2) INFORMATION FOR SEQ ID NO:84:

(i) SEQUENCE CHARACTERISTICS:
        (A) LENGTH: 104 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:84:

```
GGGGATCCTC ACGTCTCACT GGGGCACGCT GCCGCTCTGG GCGCGGTTGC GCAGGACGTG      60

GGGGCTGCTG CTCATGCCGT AGTCCCACAG GCGCTCCACG GCGG                      104
```

(2) INFORMATION FOR SEQ ID NO:85:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:85:

```
CGCGAATTCG GAAGACCCCC AGTTCAAGAA GGTGGTGTTC CAGGAGTTCA CCGACGGCAG        60

CTTCACCCAG CCCCTGTACC GCGGCGAGCT GAACGAGCAC CTGGG                       105
```

(2) INFORMATION FOR SEQ ID NO:86:

(i) SEQUENCE CHARACTERISTICS:
        (A) LENGTH: 104 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:86:

```
GGGGATCCTC ACGTCTCAGG CTTGGTTGCG AAGGTCACC ATGATGTTGT CCTCCACCTC         60

GGCGCGGATG TAGGGGCCGA GCAGGCCCAG GTGCTCGTTC AGCT                        104
```

(2) INFORMATION FOR SEQ ID NO:87:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:87:

```
CGCGAATTCG GAAGACCCAG CCTCCCGGCC CTACTCCTTC TACTCCTCCC TGATCAGCTA        60

CGAGGAGGAC CAGCGCCAGG GCGCCGAGCC CCGCAAGAAC TTCGT                       105
```

(2) INFORMATION FOR SEQ ID NO:88:

(i) SEQUENCE CHARACTERISTICS:
        (A) LENGTH: 104 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:88:

```
GGGGATCCTC ACGTCTCACT CGTCCTTGGT GGGGGCCATG TGGTGCTGCA CCTTCCAGAA        60

GTAGGTCTTA GTCTCGTTGG GCTTCACGAA GTTCTTGCGG GGCT                        104
```

(2) INFORMATION FOR SEQ ID NO:89:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:89:

```
CGCGAATTCG GAAGACCCCG AGTTCGACTG CAAGGCCTGG GCCTACTTCA GCGACGTGGA        60

CCTGGAGAAG GACGTGCACA GCGGCCTGAT CGGCCCCCTG CTGGT                       105
```

(2) INFORMATION FOR SEQ ID NO:90:

(i) SEQUENCE CHARACTERISTICS:
        (A) LENGTH: 104 base pairs
        (B) TYPE: nucleic acid
        (C) STRANDEDNESS: single (D) TOPOLOGY: linear (ii) MOLECULE TYPE: Other (xi) SEQUENCE DESCRIPTION: SEQ ID NO:90:

GGGGATCCTC ACGTCTCAGA ACAGGGCAAA TTCCTGCACA GTCACCTGCC TCCCGTGGGG     60

GGGGTTCAGG GTGTTGGTGT GGCACACCAG CAGGGGGCCG ATCA                    104

(2) INFORMATION FOR SEQ ID NO:91:

(i) SEQUENCE CHARACTERISTICS:
            (A) LENGTH: 105 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:91:

CGCGAATTCG GAAGACCCGT TCTTCACCAT CTTCGACGAG ACTAAGAGCT GGTACTTCAC     60

CGAGAACATG GAGCGCAACT GCCGCGCCCC CTGCAACATC CAGAT                   105

(2) INFORMATION FOR SEQ ID NO:92:

(i) SEQUENCE CHARACTERISTICS:
            (A) LENGTH: 104 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:92:

GGGGATCCTC ACGTCTCACA GGGTGTCCAT GATGTAGCCG TTGATGGCGT GGAAGCGGTA     60

GTTCTCCTTG AAGGTGGGAT CTTCCATCTG GATGTTGCAG GGGG                    104

(2) INFORMATION FOR SEQ ID NO:93:

(i) SEQUENCE CHARACTERISTICS:
            (A) LENGTH: 105 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:93:

CGCGAATTCG GAAGACCCCC TGCCCGGCCT GGTGATGGCC CAGGACCAGC GCATCCGCTG     60

GTACCTGCTG TCTATGGGCA GCAACGAGAA CATCCACAGC ATCCA                   105

(2) INFORMATION FOR SEQ ID NO:94:

(i) SEQUENCE CHARACTERISTICS:
            (A) LENGTH: 104 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:94:

GGGGATCCTC ACGTCTCAGT ACAGGTTGTA CAGGGCCATC TTGTACTCCT CCTTCTTGCG     60

CACGGTGAAA ACGTGGCCGC TGAAGTGGAT GCTGTGGATG TTCT                    104

(2) INFORMATION FOR SEQ ID NO:95:

(i) SEQUENCE CHARACTERISTICS:
        (A) LENGTH: 106 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:95:

CGCGAATTCG GAAGACCCGT ACCCCGGCGT RGTTCGAGAC TGTGGAGATG CTGCCCAGCA     60

AGGCCGGGAT CTGGCGCGTG GAGTGCCTGA TCGGCGAGCA CCTGCA                   106

(2) INFORMATION FOR SEQ ID NO:96:

(i) SEQUENCE CHARACTERISTICS:
        (A) LENGTH: 104 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:96:

GGGGATCCTC ACGTCTCAGC TGGCCATGCC CAGGGGGGTC TGGCACTTGT TGCTGTACAC     60

CAGGAACAGG GTGCTCATGC CGGCGTGCAG GTGCTCGCCG ATCA                     104

(2) INFORMATION FOR SEQ ID NO:97:

(i) SEQUENCE CHARACTERISTICS:
        (A) LENGTH: 106 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:97:

CGCGAATTCG GAAGACCCCA GCGGCCACAT RCCGCGACTT CCAGATCACC GCCAGCGGCC     60

AGTACGGCCA GTGGGCTCCC AAGCTGGCCC GCCTGCACTA CAGCGG                   106

(2) INFORMATION FOR SEQ ID NO:98:

(i) SEQUENCE CHARACTERISTICS:
        (A) LENGTH: 104 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:98:

GGGGATCCTC ACGTCTCACA TGGGGGCCAG CAGGTCCACC TTGATCCAGG AGAAGGGCTC     60

CTTGGTCGAC CAGGCGTTGA TGCTGCCGCT GTAGTGCAGG CGGG                     104

(2) INFORMATION FOR SEQ ID NO:99:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:99:

CGCGAATTCG GAAGACCCCA TGATCATCCA CGGCATCAAG ACCCAGGGCG CCCGCCAGAA    60

GTTCAGCAGC CTGTACATCA GCCAGTTCAT CATCATGTAC TCTCT    105

(2) INFORMATION FOR SEQ ID NO:100:

(i) SEQUENCE CHARACTERISTICS:
        (A) LENGTH: 104 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:100:

GGGGATCCTC ACGTCTCAGT TGCCGAAGAA CACCATCAGG GTGCCGGTGC TGTTGCCGCG    60

GTAGGTCTGC CACTTCTTGC CGTCTAGAGA GTACATGATG ATGA    104

(2) INFORMATION FOR SEQ ID NO:101:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:101:

CGCGAATTCG GAAGACCCCA ACGTGGACAG CAGCGGCATC AAGCACAACA TCTTCAACCC    60

CCCCATCATC GCCCGCTACA TCCGCCTGCA CCCCACCCAC TACAG    105

(2) INFORMATION FOR SEQ ID NO:102:

(i) SEQUENCE CHARACTERISTICS:
        (A) LENGTH: 104 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:102:

GGGGATCCTC ACGTCTCAGC CCAGGGGCAT GCTGCAGCTG TTCAGGTCGC AGCCCATCAG    60

CTCCATGCGC AGGGTGCTGC GGATGCTGTA GTGGGTGGGG TGCA    104

(2) INFORMATION FOR SEQ ID NO:103:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:103:

CGCGAATTCG GAAGACCCGG GCATGGAGAG CAAGGCCATC AGCGACGCCC AGATCACCGC    60

CTCCAGCTAC TTCACCAACA TGTTCGCCAC CTGGAGCCCC AGCAA    105

(2) INFORMATION FOR SEQ ID NO:104:

(i) SEQUENCE CHARACTERISTICS:
        (A) LENGTH: 104 base pairs
        (B) TYPE: nucleic acid (C) STRANDEDNESS: single
            (D) TOPOLOGY: linear (ii) MOLECULE TYPE: Other (xi) SEQUENCE DESCRIPTION: SEQ ID NO:104:

GGGGATCCTC ACGTCTCACC ACTCCTTGGG GTTGTTCACC TGGGGGCGCC AGGCGTTGCT      60

GCGGCCCTGC AGGTGCAGGC GGGCCTTGCT GGGGCTCCAG GTGG                      104

(2) INFORMATION FOR SEQ ID NO:105:

(i) SEQUENCE CHARACTERISTICS:
            (A) LENGTH: 105 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:105:

CGCGAATTCG GAAGACCCGT GGCTGCAGGT GGACTTCCAG AAAACCATGA AGGTGACTGG      60

CGTGACCACC CAGGGCGTCA AGAGCCTGCT GACCAGCATG TACGT                     105

(2) INFORMATION FOR SEQ ID NO:106:

(i) SEQUENCE CHARACTERISTICS:
            (A) LENGTH: 104 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:106:

GGGGATCCTC ACGTCTCACT TGCCGTTTTG GAAGAACAGG GTCCACTGGT GGCCGTCCTG      60

GCTGCTGCTG ATCAGGAACT CCTTCACGTA CATGCTGGTC AGCA                      104

(2) INFORMATION FOR SEQ ID NO:107:

(i) SEQUENCE CHARACTERISTICS:
            (A) LENGTH: 105 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:107:

CGCGAATTCG GAAGACCCCA AGGTGAAGGT GTTCCAGGGC AACCAGGACA GCTTCACACC      60

GGTCGTGAAC AGCCTGGACC CCCCCCTGCT GACCCGCTAC CTGCG                     105

(2) INFORMATION FOR SEQ ID NO:108:

(i) SEQUENCE CHARACTERISTICS:
            (A) LENGTH: 125 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:108:

GGGGATCCTC ACGTCTCAGC GGCCGCTTCA GTACAGGTCC TGGGCCTCGC AGCCCAGCAC      60

CTCCATGCGC AGGGCGATCT GGTGCACCCA GCTCTGGGGG TGGATGCGCA GGTAGCGGGT     120

```
                                   -continued
CAGCA                                                                 125

(2) INFORMATION FOR SEQ ID NO:109:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:109:

CGTTGTTCTT CATACGCGTC TGGGGCTCCT CGGGGC                                36

(2) INFORMATION FOR SEQ ID NO:110:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:110:

CGCGAATTCG GAAGACCC                                                    18
```

What is claimed is:

1. A synthetic gene encoding a protein normally expressed in an eukaryotic cell wherein at least one non-preferred or less preferred codon in a natural gene encoding said protein has been replaced by a preferred codon encoding the same amino acid, said synthetic gene expressing said protein at a level which is at least 110% of that expressed by said natural gene in an in vitro mammalian cell culture system under identical conditions.

2. The synthetic gene of claim 1 wherein said synthetic gene expresses said protein at a level which is at least 150% of that expressed by said natural gene in an in vitro cell culture system under identical conditions.

3. The synthetic gene of claim 1 wherein said synthetic gene expresses said protein at a level which is at least 200% of that expressed by said natural gene in an in vitro cell culture system under identical conditions.

4. The synthetic gene of claim 1 wherein said synthetic gene expresses said protein at a level which is at least 500% of that expressed by said natural gene in an in vitro cell culture system under identical conditions.

5. The synthetic gene of claim 1 wherein said synthetic gene comprises fewer than 5 occurrences of the sequence CG.

6. The synthetic gene of claim 1 wherein at least 10% of the codons in said natural gene are non-preferred codons.

7. The synthetic gene of claim 1 wherein at least 50% of the codons in said natural gene are non-preferred codons.

8. The synthetic gene of claim 1 wherein at least 50% of the non-preferred codons and less preferred codons present in said natural gene have been replaced by preferred codons.

9. The synthetic gene of claim 1 wherein at least 90% of the non-preferred codons and less preferred codons present in said natural gene have been replaced by preferred codons.

10. The synthetic gene of claim 1 wherein said protein is normally expressed by a mammalian cell.

11. The synthetic gene of claim 1 wherein said protein is a human protein.

12. The synthetic gene of claim 1 wherein 20% of the codons are preferred codons.

13. An expression vector comprising the synthetic gene of claim 1.

14. A mammalian cell which harbors the synthetic gene of claim 1.

15. The synthetic gene of claim 11 wherein said human protein is Factor VIII.

16. The expression vector of claim 13, said expression vector being a mammalian expression vector.

17. The synthetic gene of claim 15 wherein said gene has the coding sequence present in SEQ ID NO:42.

18. A method for preparing a synthetic gene encoding a protein normally expressed by mammalian cells, comprising identifying non-preferred and less-preferred codons in the natural gene encoding said protein and replacing one or more of said non-preferred and less-preferred codons with a preferred codon encoding the same amino acid as the replaced codon, so that a synthetic gene is prepared.

* * * * *

UNITED STATES PATENT AND TRADEMARK OFFICE
CERTIFICATE OF CORRECTION

PATENT NO. : 6,114,148
DATED : September 5, 2000
INVENTOR(S) : Brain Seed and Jurgen Haas It is certified that error appears in the above-identified patent and that said Letters Patent is hereby corrected as shown below:

Column 1,
Line 2, insert the following:
-- This invention was made with Government support under contract numbers AI27849, DK43031, and HL53694 awarded by the National Institutes of Health. The Government has certain rights in this invention. --

Column 10,
Table 2, line 35, above "TA" insert -- Tyr --.

Column 18,
Line 53, replace "200, g/ml" with -- 200 µg/ml --.

Column 19,
Line 4, replace "DATP" with -- dATP --;
Line 31, replace "DNTP" with -- dNTP --; and
Line 67, replace "[$^{32}$P]-dCTP" with -- [$\alpha^{32}$P] -dCTP --.

Column 20,
Line 3, replace "[$^{32}$P]-dCTP" with -- [$\alpha^{32}$P] -dCTP --.

Column 21,
Line 7, replace "25 82 g/ml" with -- 25 µg/ml --.

Column 30,
Line 39, replace "6.96" with -- 0.96 --.

Signed and Sealed this

Twenty-fourth Day of August, 2004

JON W. DUDAS
*Director of the United States Patent and Trademark Office*

UNITED STATES PATENT AND TRADEMARK OFFICE
CERTIFICATE OF CORRECTION

PATENT NO.        : 6,114,148 C1
APPLICATION NO.   : 90/011286
DATED             : September 5, 2000
INVENTOR(S)       : Seed et al.

Page 1 of 1

It is certified that error appears in the above-identified patent and that said Letters Patent is hereby corrected as shown below:

Title Page, in the Ex Parte Reexamination Certificate, under (75) Inventors, replace "Jurgen Haas, Schriesheim (DE)" with -- Jurgen Haas, Muenchen (DE) --.

Signed and Sealed this
Twenty-third Day of October, 2012

David J. Kappos
*Director of the United States Patent and Trademark Office*

(12) EX PARTE REEXAMINATION CERTIFICATE (8991st)
United States Patent
Seed et al.

(10) Number: US 6,114,148 C1
(45) Certificate Issued: *May 1, 2012

(54) HIGH LEVEL EXPRESSION OF PROTEINS

(75) Inventors: Brian Seed, Boston, MA (US); Jurgen Haas, Schriesheim (DE)

(73) Assignee: The General Hospital Corporation, Boston, MA (US)

Reexamination Request:
No. 90/011,286, Oct. 15, 2010

Reexamination Certificate for:
Patent No.: 6,114,148
Issued: Sep. 5, 2000
Appl. No.: 08/717,294
Filed: Sep. 20, 1996

( * ) Notice: This patent is subject to a terminal disclaimer.

Certificate of Correction issued Aug. 24, 2004.

(Under 37 CFR 1.47)

(51) Int. Cl.
*C07K 14/435* (2006.01)
*C07K 14/005* (2006.01)
*C07K 14/16* (2006.01)
*C07K 14/755* (2006.01)
*C12N 15/67* (2006.01)
*C12P 21/02* (2006.01)

(52) U.S. Cl. .................. 435/91.1; 435/69.1; 435/252.3; 435/320.1; 435/325; 435/440; 435/69.6; 435/91.4; 435/91.41

(58) Field of Classification Search .................. None
See application file for complete search history.

(56) References Cited

To view the complete listing of prior art documents cited during the proceeding for Reexamination Control Number 90/011,286, please refer to the USPTO's public Patent Application Information Retrieval (PAIR) system under the Display References tab.

*Primary Examiner* — Padmashri Ponnaluri

(57) ABSTRACT

The invention features a synthetic gene encoding a protein normally expressed in a mammalian cell wherein at least one non-preferred or less preferred codon in the natural gene encoding the protein has been replaced by a preferred codon encoding the same amino acid.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 8 is cancelled.

Claims 1 and 18 are determined to be patentable as amended.

Claims 2-14 and 16, dependent on an amended claim, are determined to be patentable.

New claims 19-23 are added and determined to be patentable.

Claims 15 and 17 were not reexamined.

1. A synthetic gene encoding a protein normally expressed in an eukaryotic cell wherein at least [one non-preferred or less preferred codon in a natural gene encoding said protein has been] *50% of the non-preferred or less preferred codons present in said natural gene have been* replaced by a preferred codon encoding the same amino acid, said synthetic gene expressing said protein at a level which is at least 110% of that expressed by said natural gene in an in vitro mammalian cell culture system under identical conditions.

18. A method for preparing a synthetic gene encoding a protein normally expressed by mammalian cells, comprising identifying non-preferred and less-preferred codons in the natural gene encoding said protein and replacing [one or more] *at least 50%* of said non-preferred and less-preferred codons with a preferred codon encoding the same amino acid as the replaced codon, so that a synthetic gene is prepared.

*19. A method for preparing a synthetic gene encoding a protein normally expressed by mammalian cells, comprising identifying non-preferred and less-preferred codons in the natural gene encoding said protein and replacing at least 30% of said non-preferred codons with a preferred or less-preferred codon encoding the same amino acid as the replaced codon, so that a synthetic gene is prepared.*

*20. A synthetic gene encoding a protein normally expressed in an eukaryotic cell wherein at least 30% of the non-preferred codons present in said natural gene have been replaced by a preferred codon or less preferred codon encoding the same amino acid, said synthetic gene expressing said protein at a level which is at least 110% of that expressed by said natural gene in an in vitro mammalian cell culture system under identical conditions.*

*21. A synthetic gene of claim 20 wherein said protein is normally expressed by a mammalian cell.*

*22. A synthetic gene of claim 20 wherein said protein is a human protein.*

*23. A synthetic gene encoding human Factor VIII, wherein at least one non-preferred or less preferred codon in a natural gene encoding said protein has been replaced by a preferred codon encoding the same amino acid, said synthetic gene expressing said protein at a level which is at least 110% of that expressed by said natural gene in an in vitro mammalian cell culture system under identical conditions and wherein at least 50% of non-preferred codons and less preferred codons present in said natural gene have been replaced by preferred codons.*

\* \* \* \* \*

(12) EX PARTE REEXAMINATION CERTIFICATE (10481st)
United States Patent
Seed et al.

(10) Number: US 6,114,148 C2
(45) Certificate Issued: *Jan. 23, 2015

(54) HIGH LEVEL EXPRESSION OF PROTEINS

(75) Inventors: Brian Seed, Boston, MA (US); Jurgen Haas, Munich (DE)

(73) Assignee: The General Hospital Corporation, Boston, MA (US)

Reexamination Request:
No. 90/012,334, Jun. 1, 2012

Reexamination Certificate for:
Patent No.: 6,114,148
Issued: Sep. 5, 2000
Appl. No.: 08/717,294
Filed: Sep. 20, 1996

Reexamination Certificate C1 6,114,148 issued May 1, 2012

Certificate of Correction issued Aug. 24, 2004
Certificate of Correction issued Oct. 23, 2012

( * ) Notice: This patent is subject to a terminal disclaimer.

(51) Int. Cl.
*C07K 14/16* (2006.01)
*C07K 14/005* (2006.01)
*C12N 15/67* (2006.01)
*C12P 21/02* (2006.01)
*C07K 14/435* (2006.01)

(52) U.S. Cl.
CPC ......... *C07K 14/005* (2013.01); *C07K 14/43595* (2013.01)
USPC .................. 435/91.1; 435/252.3; 435/320.1; 435/325; 435/440; 435/69.1; 435/69.6; 435/91.4; 435/91.41

(58) Field of Classification Search
None
See application file for complete search history.

(56) References Cited

To view the complete listing of prior art documents cited during the proceeding for Reexamination Control Number 90/012,334, please refer to the USPTO's public Patent Application Information Retrieval (PAIR) system under the Display References tab.

*Primary Examiner* — Shri Ponnaluri

(57) ABSTRACT

The invention features a synthetic gene encoding a protein normally expressed in a mammalian cell wherein at least one non-preferred or less preferred codon in the natural gene encoding the protein has been replaced by a preferred codon encoding the same amino acid.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 8 was previously cancelled.

Claims 18 and 20-22 are cancelled.

Claims 1 and 19 are determined to be patentable as amended.

Claims 2-7, 9-14 and 16, dependent on an amended claim, are determined to be patentable.

New claims 24-31 are added and determined to be patentable.

Claims 15, 17 and 23 were not reexamined.

1. A synthetic gene encoding a protein normally expressed in an eukaryotic cell wherein at least [50%] *60%* of the non-preferred [or less preferred] codons present in [said] *the* natural gene *encoding said protein* have been replaced by a preferred codon encoding the same amino acid, said synthetic gene expressing said protein at a level which is at least 110% of that expressed by said natural gene in an in vitro mammalian cell culture system under identical conditions.

19. A method for preparing a synthetic gene encoding a protein normally expressed [by] *in* mammalian cells, comprising identifying non-preferred and less-preferred codons in the natural gene encoding said protein and replacing at least [30%] *70%* of said non-preferred codons with a preferred or less-preferred codon encoding the same amino acid as the replaced codon, so that a synthetic gene is prepared.

*24. A synthetic gene encoding a protein normally expressed in an eukaryotic cell by a natural gene having at least 60% non-preferred codons, wherein at least 50% of the non-preferred codons present in the natural gene encoding said protein have been replaced by a preferred codon encoding the same amino acid, said synthetic gene expressing said protein at a level which is at least 110% of that expressed by said natural gene in an in vitro mammalian cell culture system under identical conditions.*

*25. The synthetic gene of claim 24 wherein said protein is normally expressed by a mammalian cell.*

*26. The synthetic gene of claim 24 wherein said protein is a human protein.*

*27. A synthetic gene encoding a protein normally expressed in an eukaryotic cell by a natural gene having at least 60% non-preferred codons, wherein at least 40% of the non-preferred codons present in said natural gene have been replaced by a preferred codon or less preferred codon encoding the same amino acid, said synthetic gene expressing said protein at a level which is at least 110% of that expressed by said natural gene in an in vitro mammalian cell culture system under identical conditions.*

*28. The synthetic gene of claim 27 wherein at least 50% of the non-preferred codons present in the natural gene encoding said protein have been replaced by a preferred codon or less preferred codon encoding the same amino acid.*

*29. The synthetic gene of claim 28 wherein at least 60% of the non-preferred codons present in the natural gene encoding said protein have been replaced by a preferred codon or less preferred codon encoding the same amino acid.*

*30. A synthetic gene encoding a protein normally expressed in an eukaryotic cell by a natural gene, wherein at least 40% of the non-preferred codons present in said natural gene have been replaced by a preferred codon or less preferred codon encoding the same amino acid, said synthetic gene expressing said protein at a level which is at least 500% of that expressed by said natural gene in an in vitro mammalian cell culture system under identical conditions.*

*31. The synthetic gene of claim 30 wherein at least 40% of the non-preferred codons present in the natural gene encoding said protein have been replaced by a preferred codon or less preferred codon encoding the same amino acid, said synthetic gene expressing said protein at a level which is at least 1000% of that expressed by said natural gene in an in vitro mammalian cell culture system under identical conditions.*

* * * * *